United States Patent
Gessner et al.

(10) Patent No.: US 10,522,767 B2
(45) Date of Patent: Dec. 31, 2019

(54) 4-OXOQUINOLINE COMPOUNDS

(71) Applicants: BASF SE, Ludwigshafen (DE); Max-Planck-Gesellschaft zur Foerderung der Wissenschaften e.V., Munich (DE)

(72) Inventors: Thomas Gessner, Heidelberg (DE); Helmut Reichelt, Neustadt (DE); Hans Reichert, Rheinfelden (DE); Daniel Jaensch, Mainz (DE); Long Chen, Mainz (DE); Klaus Muellen, Cologne (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 238 days.

(21) Appl. No.: 15/526,866

(22) PCT Filed: Sep. 29, 2015

(86) PCT No.: PCT/IB2015/057443
§ 371 (c)(1),
(2) Date: May 15, 2017

(87) PCT Pub. No.: WO2016/083914
PCT Pub. Date: Jun. 2, 2016

(65) Prior Publication Data
US 2017/0331049 A1    Nov. 16, 2017

(30) Foreign Application Priority Data
Nov. 26, 2014   (EP) ..................... 14194979

(51) Int. Cl.
*H01L 51/50* (2006.01)
*H01L 51/00* (2006.01)
(Continued)

(52) U.S. Cl.
CPC ........ *H01L 51/0072* (2013.01); *C07D 471/06* (2013.01); *C07D 471/22* (2013.01);
(Continued)

(58) Field of Classification Search
None
See application file for complete search history.

(56) References Cited

U.S. PATENT DOCUMENTS 4,461,922 A    7/1984   Gay et al.
4,539,507 A    9/1985   Vanslyke et al.
(Continued)

FOREIGN PATENT DOCUMENTS

DE   10 2004 014 046 A1   9/2004
DE   10 2010 014 933 A1   10/2011
(Continued)

OTHER PUBLICATIONS

Mullen et al., Versatile Colorant Syntheses by Multiple Condensations of Acetyl Anilines with Perylene Anhydrides, 2015, Angew. Chem. Int. Ed 54, 2285-2289 (Year: 2015).*
(Continued)

*Primary Examiner* — Gregory D Clark
(74) *Attorney, Agent, or Firm* — Oblon, McClelland, Maier & Neustadt, L.L.P.

(57) ABSTRACT

Provided is a 4-oxoquinoline compounds of the formula (I) (I) wherein A is selected from diradicals of the formulae (A.1), (A.2), (A.3), (A.4), (A.5) and (A.6), (A.1) (A.2) (A.3) (A.4) (A.5) (A.6) wherein $R^1$, $R^{2a}$, $R^{2b}$, $R^3$, $R^{3a}$, if present $R^{4a}$, $R^{4b}$, $R^{5a}$, $R^{5b}$, $R^{6a}$, $R^{6b}$, $R^{6c}$, $R^{6d}$, $R^{n1}$, $R^{n2}$, $R^{n3}$, $R^{n4}$, $R^{m5}$, $R^{m6}$, $R^{m7}$, $R^{m8}$, $R^7$, $R^{8a}$, $R^9$ and $R^{9a}$ are as defined in the claims and in the description. Also provided is a method for their preparation and their use.

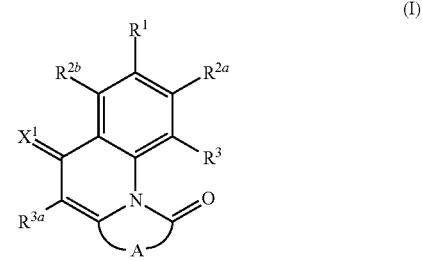

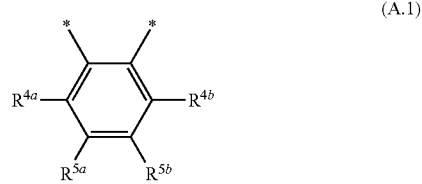

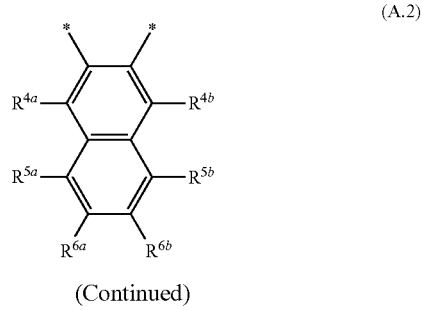

(Continued)

-continued (A.3)

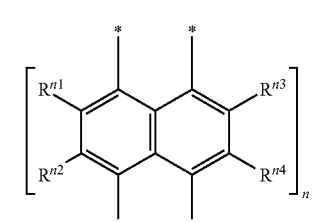

(A.4)

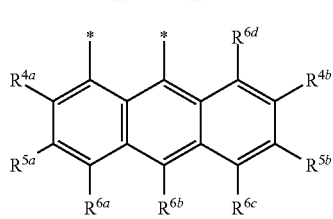

(A.5)

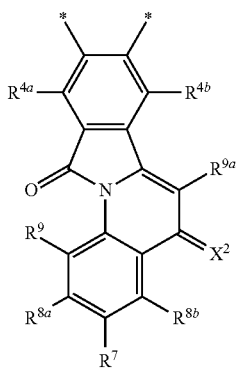

(A.6)

26 Claims, No Drawings

(51) Int. Cl.
| | |
|---|---|
| C09K 11/06 | (2006.01) |
| C07D 471/06 | (2006.01) |
| C07D 471/22 | (2006.01) |
| C09B 5/62 | (2006.01) |
| C09B 57/08 | (2006.01) |
| C09D 11/037 | (2014.01) |
| C09D 11/32 | (2014.01) |
| C09D 11/50 | (2014.01) |
| C08K 5/3437 | (2006.01) |
| C09B 57/00 | (2006.01) |
| H01L 51/52 | (2006.01) |
| H01L 51/05 | (2006.01) |
| H01L 51/42 | (2006.01) |

(52) U.S. Cl.
CPC .............. *C08K 5/3437* (2013.01); *C09B 5/62* (2013.01); *C09B 57/00* (2013.01); *C09B 57/08* (2013.01); *C09D 11/037* (2013.01); *C09D 11/32* (2013.01); *C09D 11/50* (2013.01); *C09K 11/06* (2013.01); *H01L 51/0053* (2013.01); *H01L 51/5206* (2013.01); *H01L 51/5234* (2013.01); *C09K 2211/1007* (2013.01); *C09K 2211/1018* (2013.01); *C09K 2211/1029* (2013.01); *H01L 51/0558* (2013.01); *H01L 51/42* (2013.01); *H01L 51/5056* (2013.01); *H01L 51/5088* (2013.01); *Y02E 10/549* (2013.01); *Y02P 70/521* (2015.11)

(56) References Cited

U.S. PATENT DOCUMENTS

| | | | |
|---|---|---|---|
| 4,720,432 | A | 1/1988 | Vanslyke et al. |
| 4,769,292 | A | 9/1988 | Tang et al. |
| 6,198,091 | B1 | 3/2001 | Forrest et al. |
| 6,198,092 | B1 | 3/2001 | Bulovic et al. |
| 6,451,415 | B1 | 9/2002 | Forrest et al. |
| 7,795,145 | B2 | 9/2010 | Gomez et al. |
| 2004/0046182 | A1 | 3/2004 | Chen et al. |
| 2004/0130776 | A1 | 7/2004 | Ho et al. |
| 2005/0098726 | A1 | 5/2005 | Peumans et al. |
| 2005/0224905 | A1 | 10/2005 | Forrest et al. |
| 2005/0227406 | A1 | 10/2005 | Shtein et al. |
| 2006/0202195 | A1 | 9/2006 | Marks et al. |
| 2009/0295275 | A1 | 12/2009 | Parham et al. |
| 2013/0026422 | A1 | 1/2013 | Parham et al. |
| 2014/0091265 | A1 | 4/2014 | Stoessel et al. |

FOREIGN PATENT DOCUMENTS

| | | |
|---|---|---|
| EP | 0 387 715 A2 | 9/1990 |
| EP | 0 532 798 A1 | 3/1993 |
| EP | 3 110 817 | 1/2017 |
| GB | 1 329 623 | 9/1973 |
| WO | 98/28946 A1 | 7/1998 |
| WO | 00/70655 A2 | 11/2000 |
| WO | 2005/019373 A2 | 3/2005 |
| WO | 2006/092124 A1 | 9/2006 |
| WO | 2007/031165 A2 | 3/2007 |
| WO | 2007/074137 A1 | 7/2007 |
| WO | 2007/093643 A1 | 8/2007 |
| WO | 2007/116001 A2 | 10/2007 |
| WO | 2010/049512 A1 | 5/2010 |
| WO | 2011/158211 A1 | 12/2011 |
| WO | 2012/163471 A1 | 12/2012 |
| WO | 2015/125125 A1 | 8/2015 |
| WO | WO 2015/125125 A1 * | 8/2015 ........... C07D 471/22 |

OTHER PUBLICATIONS

International Search Report dated Jan. 27, 2016 in PCT/162015/057443 filed Sep. 29, 2015.
Kerstin Schmoltner et al., "A heterotriangulene polymer for air-stable organic field-effect transistors", Polymer Chemistry, 2013, vol. 4, pp. 5337-5344.
H. Z. Alkhathlan et al., "Synthesis, spectroscopic studies, and X-ray crystal structure of N-Heteryliminophosphoranes", Phosphorus, Sulfur, and Silicon, 2004, vol. 179, pp. 373-388.
Daniel Jänsch et al., "Versatile Colorant Syntheses by Multiple Condensations of Acetyl Anilines with Perylene Anhydrides", Angewandte Chemie International Edition, 2015, vol. 54, pp. 2285-2289.

(56) References Cited

OTHER PUBLICATIONS

International Preliminary Report on Patentability and Written Opinion dated Jun. 8, 2017 in PCT/IB2015/057443.
"RN 753457-77-1; RN 143583-69-1; RN 127935-57-3; RN 127935-48-2; RN 132894-37-2; RN 127935-62-0; RN 127935-619; RN 127935-60-8; RN 127935-59-5; RN 127935-58-4; RN 127935-26-6; RN 127935-25-5; RN 127935-24-4; RN 127935- 23-3; RN 132868-89-4; RN 132868-88-3; RN 132868-87-2; RN 132868-86-1; RN 132868-85-0; RN 132868-84-9; RN 127935-30-2; RN 127935-29-9; RN 127935-28-8; RN 127935-27-7; RN 132868-90-7; RN 127935-53-9; RN 127935-52-8; RN 127935-51-7; RN 127935-50-6; RN 127935-49-3; RN 127935-35-7; RN 127935-34-6; RN 127935-33-5; RN 127935-324; RN 127935-31-3", STN Registry, Sep. 29, 2004, 206 total pages.
Jungian Feng et al., "Novel Fluorescent Dyes with Fused Perylene Tetracarboxlic Diimide and BODIPY Analogue Structures", Organic Letters, 2008, vol. 10, No. pp. 4437-4440.

\* cited by examiner

4-OXOQUINOLINE COMPOUNDS

FIELD OF THE INVENTION

The present invention relates to a new class of 4-oxoquinoline compounds, a method for their preparation and to their use.

Rylenes (or poly(peri-naphthalene)s) and rylene derivatives are a class of chromophores that is characterized by at least two naphthalene units bound to each other in the peri-positions. Naphtalene-tetracarboxylic dianhydrides, rylene-tetracarboxylic dianhydrides and their corresponding diimides have become of outstanding importance as classical colorants, both, as dyes and pigments, as well as active components of electronic and optoelectronic devices.

WO 2007/031165 A2 describes compounds of the formulae (1) and (2)

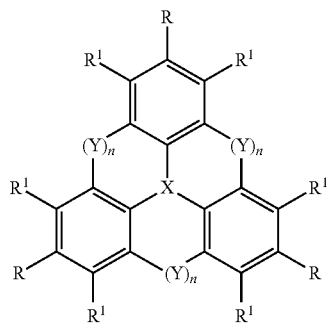

Formula (1)

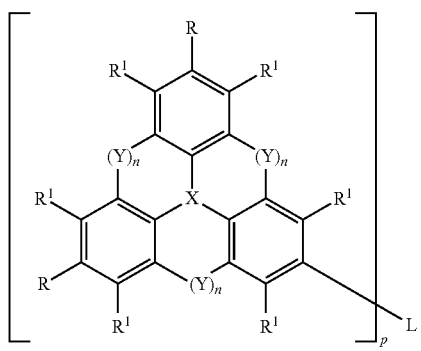

Formula (2)

where p is 2 to 6 depending on the valence of the L group, and the use of those compounds in electroluminescent devices, such as OLED and OFET. The concrete compounds contain only one (hetero)triangulene moiety as central core.

Kerstin Schmoltner, Florian Schlütter, Milan Kivala, Martin Baumgarten, Stefanie Winkler, Roman Trattnig, Norbert Koch, Andreas Klug, Emil J. W. List and Klaus Müllen describe in Polym. Chem., 2013, 4, 5337 a heterotriangulene polymer for air-stable organic field-effect transistors.

DE 10 2010 014 933 A1 describes heteroaromatic compounds of the general formula (A) and their use in organic electronics

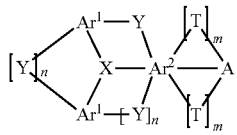

(A)

wherein

X is N, P, or P=O;

Y is, identically or differently on each occurrence, $C(R^1)_2$, C=O, C=$NR^1$, O, S, SO, $SO_2$, $PR^1$, $POR^1$, NAr, $NR^1$, or a single bond;

T is, identically or differently on each occurrence $C(R^1)_2$, C=O, C=$NR^1$, O, S, SO, $SO_2$, $PR^1$, $POR^1$, NAr, $NR^1$, or a single bond;

A is $Ar^3$ or $X(Ar^4)_2$, wherein the bond to a group T starts from the aromatic or heteroaromatic ring of the group $Ar^3$ or $Ar^4$, and the two groups $Ar^4$ of a group $X(Ar^4)_2$ are optionally connected to one another via a group T;

Ar, $Ar^1$, $Ar^2$, $Ar^3$, and $Ar^4$ are, identically or differently on each occurrence, an aryl or heteroaryl group having 5 to 30 aromatic ring atoms optionally substituted by one or more radicals $R^2$.

WO 2012163471 relates to metal complexes of the general formula

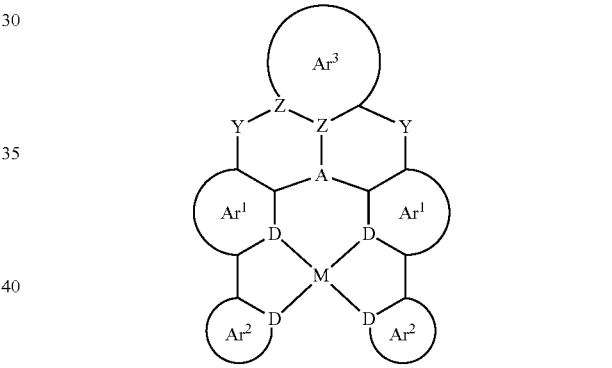

wherein

M is a transition metal

A is N, P, B, $C^-$ or CR;

Y can have in each case the same or different meanings and is $CR_2$, NR, O, S or a single bond;

Z can have in each case the same or different meanings and is C or N;

$Ar^1$, $Ar^2$ and $Ar^3$ are aryl or heteroaryl group;

and also to electronic devices, more particularly organic electroluminescent devices, which comprise these metal complexes.

The unpublished European patent application EP 14156298.3 relates to a new class of cycl[3.3.3]azines and to their use as semiconductor material.

H. Z. Alkhathlan, M. A. Al-Jaradah, K. A. Al-Farhan and A. A. Mousa. describe in Phosphorous, Sulfur and Silicon, 179: 373-388, 2004, the preparation of N-heteryliminophosphoranes starting from 2-acetylaniline and phthalic anhydride, 3-nitrophthalic anhydride, 4-nitrophthalic anhydride or 3, 4,5,6-tetrachlorophthalic anhydride. Merely the reaction of 3-nitrophthalic anhydride and 3,4,5,6-tetrachlorophthalic anhydride, respectively, leads to the formation of an isoindolo[2,3-a]quinoline-5,11-dione compound, namely 7-nitroisoindolo[2,3-a]quinoline-5,11-dione and 7,8,9,10-tetrachloroisoindolo[2,3-a]quinoline-5,11-dione, respectively, as byproduct. No mention is made to any use of 7-nitroisoindolo[2,3-a]quinoline-5,11-dione or 7,8,9,10-tetrachloroisoindolo[2,3-a]quinoline-5,11-dione.

Angew. Chem. Int. Ed 2015, 54, 2285-2289 (DOI: 10.1002/anie.201409634) which was published online after the priority date of this application describes 4-oxoquinoline and 4-hydoxyquinoline rylene compounds.

It has been found that some of these compounds have application properties that are still worth of improvement. Generally, there is still a need for new colorants that can be easily incorporated into a great variety of polymer compositions. Preferably, these compositions should be processable under the conventional temperatures for thermoplastics, without the color or other optical properties changing significantly during processing. Thus, there remains a need for improved colorants.

Thus, it is an object of the present invention to provide novel colorants having advantageous application properties. The colorants should have at least one of the following properties:
suitability for extrusion or molding applications;
suitability for security printing;
suitability as semiconductor material in organic electronics and organic photovoltaics;
high photostability;
high thermal stability;
high light fastness;
high molar extinction coefficient.

It has now been found that, surprisingly, 4-oxoquinoline compounds are particularly advantageous as colorants. In addition, they are advantageous as semiconductor materials in organic electronics and organic photovoltaics.

SUMMARY OF THE INVENTION

According to a first aspect of the present invention there is provided a compound of the general formula (I)

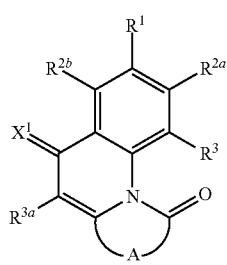

(I)

wherein
$R^1$, $R^{2a}$ and $R^{2b}$ are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^3$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^{3a}$ is hydrogen, in each case unsubstituted or substituted alkyl or aryl;

$X^1$ is O or $C(CN)_2$;

A is a diradical selected from diradicals of the general formulae (A.1), (A.2), (A.3), (A.4), (A.5), and (A.6)

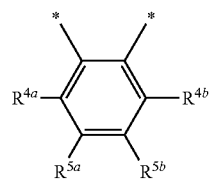

(A.1)

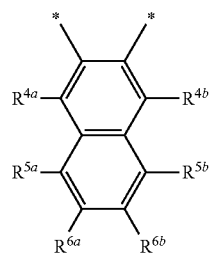

(A.2)

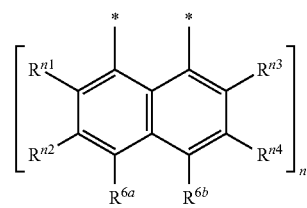

(A.3)

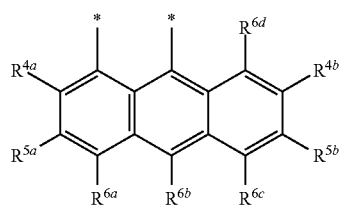

(A.4)

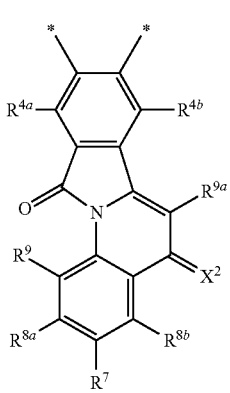

(A.5)

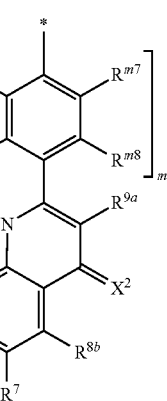

(A.6)

wherein

* in each case denotes the point of attachments to the quinoline skeleton and the carbonyl carbon atom;

n is 1, 2, 3 or 4;

m is 1, 2, 3 or 4;

$R^{4a}$, $R^{4b}$, $R^{5a}$, $R^{5b}$, $R^{6a}$, $R^{6b}$, $R^{6c}$, $R^{6d}$, at each occurrence, $R^{n1}$, $R^{n2}$, $R^{n3}$, $R^{n4}$, $R^{m5}$, $R^{m6}$, $R^{m7}$ and $R^{m8}$, are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^7$, $R^{8a}$, $R^{8b}$ are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^9$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^{9a}$ is hydrogen, in each case unsubstituted or substituted alkyl or aryl; and $X^2$ is O or $C(CN)_2$;

wherein $E^1$ and $E^2$, at each occurrence, are each independently selected from hydrogen, alkyl, cycloalkyl, heterocycloalkyl, aryl and hetaryl.

except for the following compounds:

7-nitroisoindolo[2,3-a]quinoline-5,11-dione; and 7,8,9,10-tetrachloroisoindolo[2,3-a]quinoline-5,11-dione.

According to a further aspect of the present invention there are provided processes for preparing a compound of the formula (I).

According to a further aspect of the present invention there is provided the use of a compound of the general formula (I), as defined above and in the following as fluorescent colorant, in particular as fluorescent colorant in a display based on fluorescence conversion, for data storage, as a UV absorber, for optical labels, as a fluorescent label for biomolecules, in the laser welding of polymer materials, in inks, preferably in ink jet inks and printing inks, in surface coatings, preferably as or in the colored layer of a coating composition, in particular in a coating composition for the automotive industry, and for coloring polymer compositions.

According to a further aspect of the present invention there is provided a composition comprising at least one compound of the formula (I) as defined above and in the following and at least polymer, preferably at least one thermoplastic polymer.

According to a further aspect of the present invention there is provided an organic field-effect transistor comprising a substrate having at least one gate structure, a source electrode and a drain electrode and at least one compound of the formula (I) as defined above and in the following as a semiconductor material.

The compounds of the formula (I) can be in principle used as n-type semiconductors or as p-type semiconductors. If a compound of the formula (I) acts as n-type semiconductor or as p-type semiconductors depends inter alia on the employed gate dielectric. Gate dielectrics are usually employed in the form of a self-assembled monolayer (SAM) of suitable compounds, e.g. silanes with more or less electronegative substituents, alkyl phosphonic acid, fluoroalkyl phosphonic acid, etc. By choosing a certain SAM gate dielectric or a certain mixture of different SAM gate dielectrics, it is possible to control the properties of the semiconductor material. In electronic devices that employ a combination of two different semiconductors, e.g. organic solar cells, it depends on the corresponding semiconductor material if a compound of the formula (I) acts as n-type semiconductor or as p-type semiconductor.

According to a further aspect of the present invention there is provided a substrate comprising a plurality of organic field-effect transistors, at least some of the field-effect transistors comprising at least one compound of the formula (I) as defined above and in the following.

According to a further aspect of the present invention there is provided a semiconductor unit comprising at least one substrate comprising a plurality of organic field-effect transistors, at least some of the field-effect transistors comprising at least one compound of the formula (I) as defined above and in the following.

According to a further aspect of the present invention there is provided an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I) as defined above and in the following.

In a preferred embodiment, the electroluminescent arrangement is in form of an organic light-emitting diode (OLED).

According to a further aspect of the present invention there is provided an organic solar cell comprising at least one compound of the formula (I) as defined above and in the following.

According to a further aspect of the present invention there is provided the use of a compound of the general formula (I), as defined above and in the following, as a semiconductor material.

In a preferred embodiment, the compound of the general formula (I) are used as a semiconductor material in organic electronics or in organic photovoltaics.

Further embodiments will be apparent from the claims, the description and the examples.

DETAILED DESCRIPTION OF THE INVENTION

The novel compounds of the formula (I), where A is a radical of the formulae (A.3) or (A.6) are characterized in that the 4-oxoquinoline motif is bound with its 2-position to one of the peri-positions of the naphthalene or rylene core and a carbonyl bridge binds the nitrogen atom of the 4-oxoquinoline unit to the other peri-position of the naphthalene or rylene core.

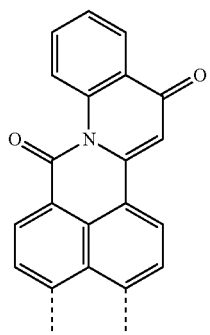

In the compounds of the formula (I), wherein A is a group of the formula (A.3), n is the number of naphthalene units which for n=2, 3 or 4 are bonded in the peri-position and form the basic skeleton of the rylene compounds. In the individual $R^{n1}$ to $R^{n4}$ radicals, n is the particular naphthalene group of the rylene skeleton to which the radicals are bonded. $R^{n1}$ to $R^{n4}$ radicals which are bonded to different naphthalene groups may each have the same or different definitions. Accordingly, the compounds of the formula (I) wherein A is a group of the formula (A.3) may have the following formulae:

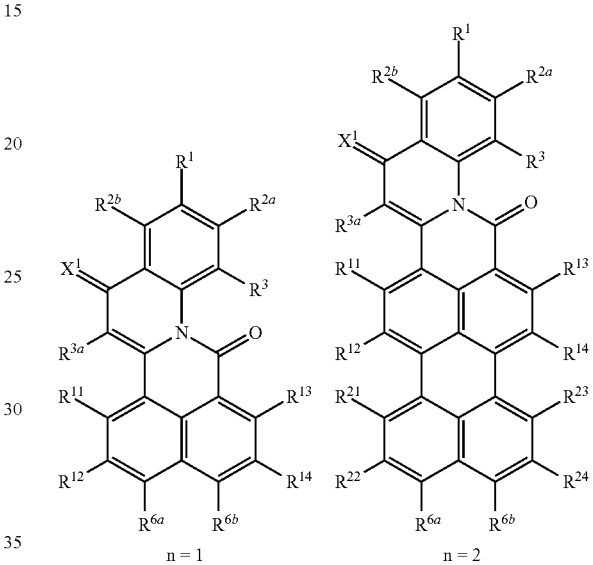

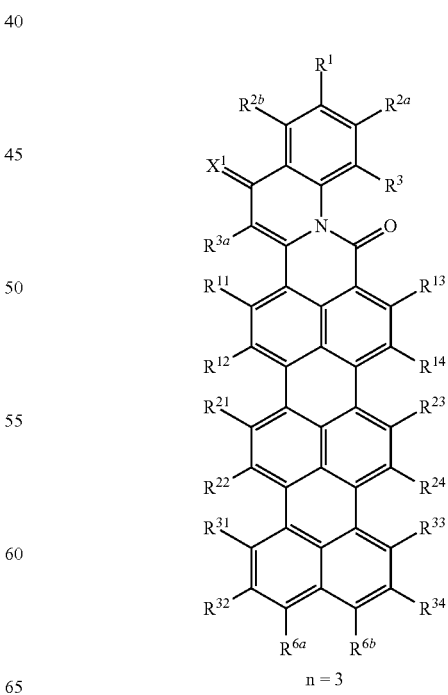

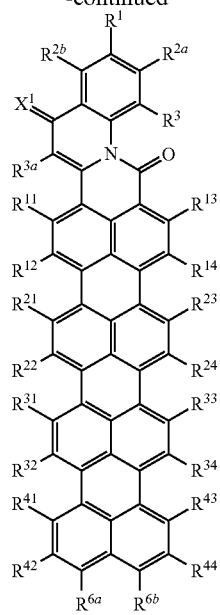

n = 4

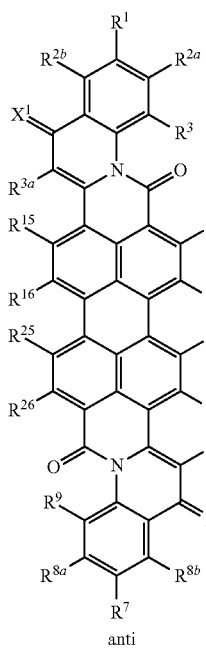

anti

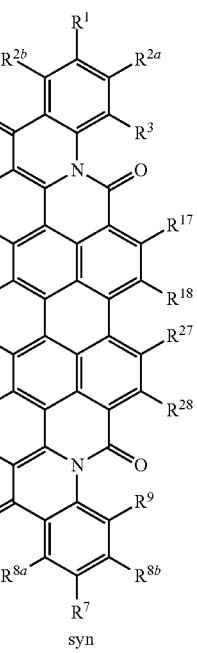

syn m = 2

In the compounds of the formula (I), wherein A is a group of the formula (A.6), m is the number of naphthalene units which for m=2, 3 or 4 are bonded in the peri-position and form the basic skeleton of the rylene compounds. In the individual $R^{m5}$ to $R^{m8}$ radicals, m is the particular naphthalene group of the rylene skeleton to which the radicals are bonded. $R^{m5}$ to $R^{m8}$ radicals which are bonded to different naphthalene groups may each have the same or different definitions. The group of the formula (A.6) can be bound either syn or anti with regard to the quinoline skeleton. Accordingly, the compounds of the formula (I) wherein A is a group of the formula (A.6) may have the following formulae:

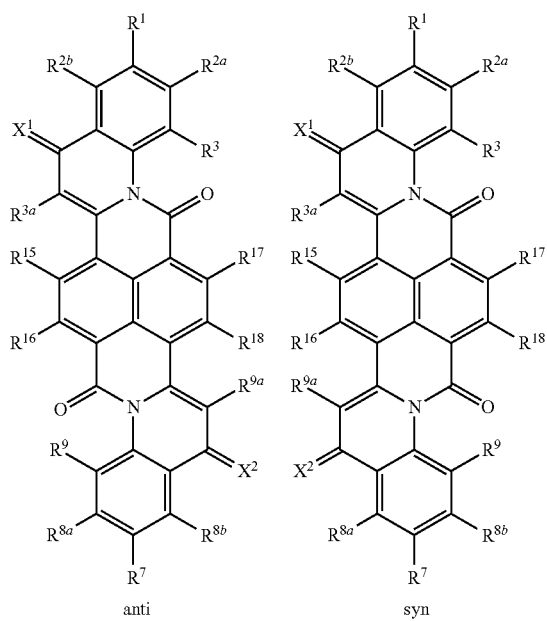

anti        syn m = 1

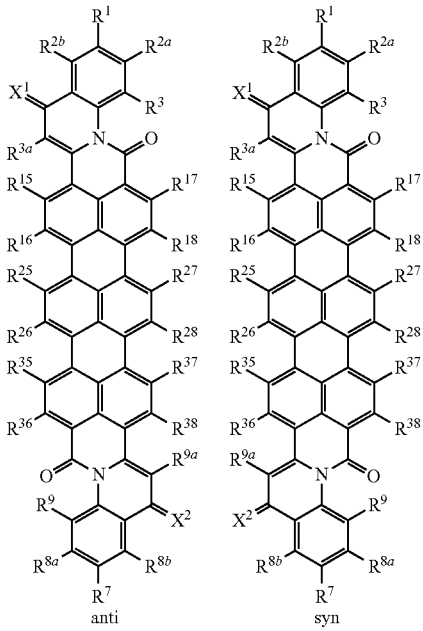

anti     syn m = 3

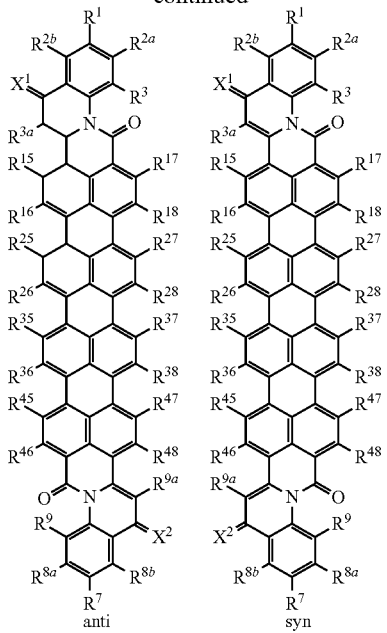

m = 4

In the context of the invention, the expression "halogen" denotes in each case fluorine, bromine, chlorine or iodine, particularly chlorine, bromine or iodine.

In the context of the invention, the term "sulfo" means —$SO_3H$.

In the context of the invention, the expression "unsubstituted or substituted alkyl, cycloalkyl, heterocycloalkyl, aryl and hetaryl" represents unsubstituted or substituted alkyl, unsubstituted or substituted cycloalkyl, unsubstituted or substituted heterocycloalkyl, unsubstituted or substituted aryl and unsubstituted or substituted hetaryl.

In the context of the invention, the expression "unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino" represents unsubstituted or substituted alkyl, unsubstituted or substituted alkoxy, unsubstituted or substituted alkylthio, unsubstituted or substituted (monoalkyl)amino, unsubstituted or substituted (dialkyl)amino, unsubstituted or substituted cycloalkyl, unsubstituted or substituted cycloalkoxy, unsubstituted or substituted cycloalkylthio, unsubstituted or substituted (monocycloalkyl)amino, unsubstituted or substituted (dicycloalkyl)amino, unsubstituted or substituted heterocycloalkyl, unsubstituted or substituted heterocycloalkoxy, unsubstituted or substituted heterocycloalkylthio, unsubstituted or substituted (monoheterocycloalkyl)amino, unsubstituted or substituted (diheterocycloalkyl)amino, unsubstituted or substituted aryl, unsubstituted or substituted aryloxy, unsubstituted or substituted arylthio, unsubstituted or substituted (monoaryl)amino, unsubstituted or substituted (diaryl)amino, unsubstituted or substituted hetaryl, unsubstituted or substituted hetaryloxy, unsubstituted or substituted hetarylthio, unsubstituted or substituted (monohetaryl)amino and unsubstituted or substituted (dihetaryl)amino.

In the context of the present invention, the expression "alkyl" comprises straight-chain or branched alkyl groups. Alkyl is preferably $C_1$-$C_{30}$-alkyl, more preferably $C_1$-$C_{20}$-alkyl and most preferably $C_1$-$C_{10}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, n-eicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

The expression alkyl also comprises alkyl radicals whose carbon chains may be interrupted by one or more nonadjacent groups which are selected from —O—, —S—, —NR$^a$—, —C(=O)—, —S(=O)— and/or —S(=O)$_2$—. R$^a$ is preferably hydrogen, alkyl, cycloalkyl, heterocycloalkyl, aryl or hetaryl.

Examples of alkyl groups whose carbon chains are interrupted by one or more, e.g. 1, 2, 3, 4, 5, 6, 7, 8 or more than 8, nonadjacent groups are especially 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl; 2-methylthioethyl, 2-ethylthioethyl, 2-propylthioethyl, 2-isopropylthio-ethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-tri-thiadecyl, 3,6,9-trithiaundecyl, 3,6,9-trithiadodecyl, 3,6,9,12-tetrathiatridecyl and 3,6,9,12-tetrathiatetradecyl; 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl; (1-ethylethylidene)aminoethylene, (1-ethylethylidene)-aminopropylene, (1-ethylethylidene)aminobutylene, (1-ethylethylidene)aminodecylene and (1-ethylethylidene)aminododecylene; propan-2-on-1-yl, butan-3-on-1-yl, butan-3-on-2-yl and 2-ethylpentan-3-on-1-yl; 2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl; 2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^5$E$^6$ where E$^5$ and E$^6$ are each independently hydrogen, alkyl, cycloalkyl, heterocycloalkyl, aryl or hetaryl. Cycloalkyl, heterocycloalkyl, aryl and hetaryl substituents of the alkyl groups may in turn be unsubstituted or substituted; suitable substituents are the substituents mentioned below for these groups. Special embodiments of substituted alkyl groups are perfluoro-C$_1$-C$_{30}$-alkyl, 1H, 1H-perfluoro-C$_2$-C$_{30}$-alkyl and 1H, 1H, 2H, 2H-perfluoro-C$_3$-C$_{30}$-alkyl. Examples for those fluorinated alkyl groups are mentioned in the following.

Examples of substituted alkyl groups are especially carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxy-tetradecyl; sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl; 2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl; 2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl; 2-chloroethyl, 2- and 3-chloropropyl, 2-, 3- and 4-chlorobutyl, 2-bromoethyl, 2- and 3-bromopropyl and 2-, 3- and 4-bromobutyl; 2-nitroethyl, 2- and 3-nitropropyl and 2-, 3- and 4-nitrobutyl.

Carboxylate and sulfonate respectively represent a derivative of a carboxylic acid function and a sulfonic acid function, especially a metal carboxylate or sulfonate, a carboxylic ester or sulfonic ester function or a carboxamide or sulfonamide function. Such derivatives include, for example, esters with C$_1$-C$_4$-alkanols, such as methanol, ethanol, n-propanol, isopropanol, n-butanol, sec-butanol and tert-butanol.

The above remarks regarding alkyl also apply to the alkyl moiety in alkoxy, alkylthio (=alkylsulfanyl), monoalkylamino and dialkylamino.

Examples of alkoxy groups are especially methoxy, ethoxy, propoxy, isopropoxy, butoxy, isobutoxy, sec-butoxy, tert-butoxy, pentoxy, isopentoxy, neopentoxy, tert-pentoxy and hexoxy.

Alkylthio is also referred to as alkylsulfanyl. Examples of alkylthio groups are especially methylthio, ethylthio, propylthio, isopropylthio, butylthio, isobutylthio, sec-butylthio, tert-butylthio, pentylthio, isopentylthio, neopentylthio, tert-pentylthio and hexylthio.

Examples of monoalkylamino groups and dialkylamino groups are especially methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

Alkylene represents a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

In the context of the present invention, the term "cycloalkyl" denotes a mono-, bi- or tricyclic hydrocarbon radical having usually from 3 to 20, preferably 3 to 12, more preferably 5 to 12, carbon atoms such as cyclopropyl, cyclobutyl, cyclopentyl, cyclohexyl, cycloheptyl, cyclooctyl, cyclododecyl, cyclopentadecyl, norbornyl, bicyclo[2.2.2]octyl or adamantyl.

Substituted cycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, SO$_3$H, sulfonate, sulfamino, sulfamide, amidino, NE$^7$E$^8$ where E$^7$ and E$^8$ are each independently hydrogen, alkyl, cycloalkyl, heterocycloalkyl, aryl or hetaryl. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methyl-cyclooctyl, 2-, 3-, 4- and 5-ethylcyclooctyl, 2-, 3-, 4- and 5-propylcyclooctyl, 3- and 4-hydroxycyclohexyl, 3- and 4-nitrocyclohexyl and 3- and 4-chlorocyclohexyl.

The above remarks regarding cycloalkyl also apply to the cycloalkyl moiety in cycloalkoxy, cycloalkylthio (=cycloalkylsulfanyl), monocycloalkylamino and dicycloalkylamino.

In the context of the present invention, the term "aryl" refers to mono- or polycyclic aromatic hydrocarbon radicals. Aryl usually is an aromatic radical having 6 to 24 carbon atoms, preferably 6 to 20 carbon atoms, especially 6 to 14 carbon atoms as ring members. Aryl is preferably phenyl, naphthyl, indenyl, fluorenyl, anthracenyl, phenanthrenyl, naphthacenyl, chrysenyl, pyrenyl, coronenyl, perylenyl, etc., and more preferably phenyl or naphthyl.

Substituted aryls may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^9E^{10}$ where $E^9$ and $E^{10}$ are each independently hydrogen, alkyl, cycloalkyl, heterocycloalkyl, aryl or hetaryl. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, (2-chloro-6-methyl)phenyl, (2-chloro-6-ethyl)phenyl, (4-chloro-6-methyl)phenyl, (4-chloro-6-ethyl)phenyl.

The above remarks regarding aryl also apply to the aryl moiety in aryloxy, arylthio (=arylsulfanyl), monoarylamino and diarylamino.

In the context of the present invention, the expression "heterocycloalkyl" comprises nonaromatic, unsaturated or fully saturated, cycloaliphatic groups having generally 5 to 8 ring atoms, preferably 5 or 6 ring atoms. In the heterocycloalkyl groups, compared to the corresponding cycloalkyl groups, 1, 2, 3, 4 or more than 4 of the ring carbon atoms are replaced by heteroatoms or heteroatom-containing groups. The heteroatoms or heteroatom-containing groups are preferably selected from —O—, —S—, —$NR^b$—, —C(=O)—, —S(=O)— and/or —S(=O)$_2$—. $R^b$ is preferably hydrogen, alkyl, cycloalkyl, heterocycloalkyl, aryl or hetaryl. Examples of heterocycloalkyl groups are especially pyrrolidinyl, piperidinyl, 2,2,6,6-tetramethylpiperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl.

Substituted heterocycloalkyl groups may, depending on the ring size, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{11}E^{12}$ where $E^{11}$ and $E^{12}$ are each independently hydrogen, alkyl, cycloalkyl, heterocycloalkyl, aryl or hetaryl. In the case of substitution, the heterocycloalkyl groups preferably bear one or more, for example one, two, three, four or five, $C_1$-$C_6$-alkyl groups.

The above remarks regarding heterocycloalkyl also apply to the heterocycloalkyl moiety in heterocycloalkoxy, heterocycloalkylthio (=heterocycloalkylsulfanyl), monoheterocycloalkylamino and diheterocycloalkylamino.

In the context of the present invention, the expression "hetaryl" (also referred to as heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently selected from alkyl, alkoxy, alkylthio, cycloalkyl, heterocycloalkyl, aryl, hetaryl, fluorine, chlorine, bromine, hydroxyl, mercapto, cyano, nitro, nitroso, formyl, acyl, COOH, carboxylate, alkylcarbonyloxy, carbamoyl, $SO_3H$, sulfonate, sulfamino, sulfamide, amidino, $NE^{13}E^{14}$ where $E^{13}$ and $E^{14}$ are each independently hydrogen, alkyl, cycloalkyl, heterocycloalkyl, aryl or hetaryl. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding hetaryl also apply to the hetaryl moiety in hetaryloxy, hetarylthio, monohetarylamino and dihetarylamino.

For the purposes of the present invention, the expression "acyl" refers to alkanoyl or aroyl groups which generally have from 2 to 11, preferably from 2 to 8, carbon atoms, for example the acetyl, propanoyl, butanoyl, pentanoyl, hexanoyl, heptanoyl-, 2-ethyl-hexanoyl, 2-propylheptanoyl, pivaloyl, benzoyl or naphthoyl group.

The groups $NE^1E^2$, $NE^3E^4$, $NE^5E^6$, $NE^7E^8$, $NE^9E^{10}$, $NE^{11}E^{12}$ and $NE^{13}E^{14}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

Embodiments of the present invention as well as preferred compounds of the present invention are outlined in the following paragraphs. The remarks made below concerning preferred embodiments of the variables of the compounds of formula (I), especially with respect to their substituents $X^1$, $X^2$, $R^1$, $R^{2a}$, $R^{2b}$, $R^3$, $R^{3a}$, $R^{4a}$, $R^{4b}$, $R^{5a}$, $R^{5b}$, $R^{6a}$, $R^{6b}$, $R^{6c}$, $R^{6d}$, $R^{n1}$, $R^{n2}$, $R^{n3}$, $R^{n4}$, $R^{m5}$, $R^{m6}$, $R^{m7}$, $R^{m8}$, $R^7$, $R^{8a}$, $R^{8b}$, $R^9$, $R^{9a}$ and their variables n and m are valid both on their own and, in particular, in every possible combination with each other.

When * or # appears in a formula showing a preferred substructure of a compound of the present invention, it denotes the attachment bond in the remainder molecule.

Preferably, the radicals $R^1$, $R^{2a}$, $R^{2b}$, are independently of one another selected from hydrogen, chlorine, bromine, linear $C_1$-$C_{30}$-alkyl, branched $C_3$-$C_{30}$-alkyl, $C_1$-$C_{30}$-haloalkyl, a radical of the formula (G.1), a radical of the formula (G.2) and a radical of the formula (G.3)

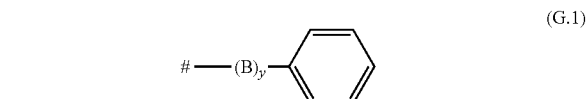

(G.1)

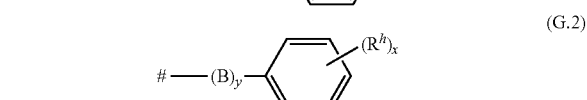

(G.2)

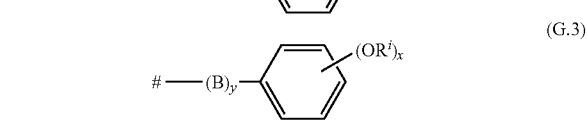

(G.3)

where
# represents the bonding side to the remainder of the molecule;
B if present, is selected from O, S and a $C_1$-$C_{10}$-alkylene group which may be interrupted by one or more nonadjacent groups which are selected from O and S;
y is 0 or 1;
$R^h$ is independently of one another selected from $C_1$-$C_{30}$-alkyl, $C_1$-$C_{30}$-fluoroalkyl, fluorine, chlorine, bromine, $NE^3E^4$, nitro, $SO_3H$ and cyano, where $E^3$ and $E^4$, independently of one another, are hydrogen, alkyl, cycloalkyl, heterocycloalkyl, aryl or hetaryl;
$R^i$ is independently of one another selected from $C_1$-$C_{30}$-alkyl;
x in formulae G.2 and G.3 is 1, 2, 3, 4 or 5.

If B is present, i.e. if y is 1, the variable B is preferably O or a $C_1$-$C_{10}$-alkylene group.

Irrespectively of its occurrence, $R^h$ is preferably selected from $C_1$-$C_{30}$-alkyl. Irrespectively of its occurrence, $R^1$ is preferably selected from $C_1$-$C_{30}$-alkyl.

In the compounds of the formula (I), the $R^{2a}$ and $R^{2b}$ radicals may have identical or different definitions. In a preferred embodiment, the $R^{2a}$ and $R^{2b}$ radicals have identical definitions.

The radical $R^1$ is preferably selected from hydrogen, chlorine, bromine, $C_1$-$C_{30}$-alkyl and $C_1$-$C_{30}$-haloalkyl. More preferably, $R^1$ is selected from hydrogen, chlorine, bromine, linear $C_1$-$C_{30}$-alkyl, branched $C_3$-$C_{30}$-alkyl, perfluoro-$C_1$-$C_{30}$-alkyl, 1H, 1H-perfluoro-$C_2$-$C_{30}$-alkyl, and 1H, 1H, 2H, 2H-perfluoro-$C_3$-$C_{30}$-alkyl.

In particular, $R^1$ is selected from
hydrogen;
chlorine, bromine;
methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl, n-eicosyl;
branched $C_3$-$C_{30}$-alkyl, selected from a radical of the general formulae (III.1) and (III.2)

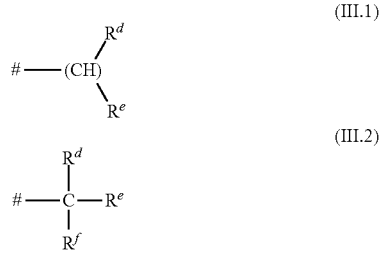

in which # is a bonding site to the remainder of the molecule, and in the formula (III.1) $R^d$ and $R^e$ are independently selected from $C_1$— to $C_{28}$-alkyl, where the sum of the carbon atoms of the $R^d$ and $R^e$ radicals is an integer from 2 to 29;

in the formula (III.2) $R^d$, $R^e$ and $R^f$ are independently selected from $C_1$- to $C_{27}$-alkyl, where the sum of the carbon atoms of the $R^d$, $R^e$ and $R^f$ radicals is an integer from 3 to 29;

$CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$;

$CH_2$—$CF_3$, $CH_2$—$C_2F_5$, $CH_2$-(n-$C_3F_7$), $CH_2$-(n-$C_4F_9$), $CH_2$-(n-$C_5F_{11}$), $CH_2$-(n-$C_6F_{13}$), $CH_2$—$CF(CF_3)_2$, $CH_2$—$C(CF_3)_3$, $CH_2$—$CF_2CF(CF_3)_2$, $CH_2$—$CF(CF_3)(C_2F_5)$;

$CH_2$—$CH_2$—$CF_3$, $CH_2$—$CH_2$—$C_2F_5$, $CH_2$—$CH_2$-(n-$C_3F_7$), $CH_2$—$CH_2$-(n-$C_4F_9$), $CH_2$—$CH_2$-(n-$C_5F_{11}$), $CH_2$—$CH_2$-(n-$C_6F_{13}$), $CH_2$—$CH_2$—$CF(CF_3)_2$, $CH_2$—$CH_2$—$C(CF_3)_3$, $CH_2$—$CH_2$—$CF_2CF(CF_3)_2$ and $CH_2$—$CH_2$—$CF(CF_3)(C_2F_5)$.

In the context of the formulae (III.1) and (III.2), preferably, the $R^d$, $R^e$ and $R^f$ radicals are independently selected from $C_1$- to $C_{12}$-alkyl, especially $C_1$- to $C_8$-alkyl.

Examples of preferred radicals of the formula (III.1) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

A suitable radical of the formula (III.2) is tert.-butyl.

In a specially preferred embodiment, the radical $R^1$ is selected from hydrogen, chlorine, linear $C_1$-$C_{10}$-alkyl, a radical of the formulae (III.1) or (III.2).

Even more preferably, $R^1$ is selected from hydrogen, chlorine, bromine and branched $C_3$-$C_{10}$-alkyl. Preferably, branched $C_3$-$C_{10}$-alkyl is a radical of the formulae (III.1) or (III.2).

Preferred are compounds of formula (I), wherein $R^3$ is hydrogen.

Preferred are compounds of formula (I), wherein $R^{2a}$, $R^{2b}$ and $R^3$ are each hydrogen.

Preferred are compounds of formula (I), wherein $R^{3a}$ is hydrogen.

$X^1$ is preferably O. Likewise, preference is given to compounds of formula (I), where $X^1$ is $C(CN)_2$.

Embodiments (a)

According to a first group of embodiments, compounds of formula (I) are preferred, wherein A is selected from radicals of the formulae (A.1), (A.2) and (A.4), wherein $R^{4a}$, $R^{4b}$, $R^{5a}$, $R^{5b}$, and, if present, $R^{6a}$, $R^{6b}$, $R^{6c}$ and $R^{6d}$, are as defined above. The compounds of the general formula (I), wherein group A is selected from radicals of the formulae (A.1), (A.2) and (A.4), are denoted in the following also as "group of embodiments (a) or embodiments (a)". All definitions of substituents and variables regarding the group of embodiments (a), where applicable, refer to the compounds of the general formula (I), wherein group A is selected from radicals of the formulae (A.1), (A.2) and (A.4).

In the compounds of the formula (I) according to the group of embodiments (a), $R^1$, $R^{2a}$, $R^{2b}$ and $R^3$ are as defined above and preferably have one of the preferred meanings. In particular, $R^1$ is selected from hydrogen, chlorine, bromine and branched $C_3$-$C_{10}$-alkyl. In particular, $R^{2a}$, $R^{2b}$, $R^3$ and $R^{3a}$ are each hydrogen.

In the compounds of the formula (I) according to the group of embodiments (a), the $R^{4a}$ and $R^{4b}$ radicals may have identical or different definitions. In a preferred embodiment, the $R^{4a}$ and $R^{4b}$ radicals have identical definitions. In the compounds of the formula (I), the $R^{5a}$ and $R^{5b}$ radicals may have identical or different definitions. In a preferred embodiment, the $R^{5a}$ and $R^{5b}$ radicals have identical definitions. In the compounds of the formula (I), the $R^{6a}$ and $R^{6b}$ radicals may have identical or different definitions. In a preferred embodiment, the $R^{6a}$ and $R^{6b}$ radicals have identical definitions. In the compounds of the formula (I), the $R^{6c}$ and $R^{6d}$ radicals may have identical or different definitions. In a preferred embodiment, the $R^{6c}$ and $R^{6d}$ radicals have identical definitions. In this group of embodiments (a), $R^{4a}$, $R^{4b}$, $R^{5a}$, $R^{5b}$ and, if present, $R^{6a}$, $R^{6b}$, $R^{6c}$ and $R^{6d}$ are in particular selected from hydrogen, linear $C_1$-$C_{30}$-alkyl, branched $C_3$-$C_{30}$-alkyl, perfluoro-$C_1$-$C_{30}$-alkyl, 1H, 1H-perfluoro-$C_2$-$C_{30}$-alkyl, 1H, 1H, 2H, 2H-perfluoro-$C_3$-$C_{30}$-alkyl, $C_1$-$C_{30}$-alkoxy, $C_1$-$C_{30}$-alkylsulfanyl, a radical of the formula (G.1), a radical of the formula (G.2) and a radical of the formula (G.3).

Embodiments (b)

According to a second group of embodiments, compounds of formula (I) are preferred, wherein A is a radical of the formula (A.3) and $R^{3a}$ is hydrogen. Compounds of the formula (I), where A is a radical of the formula A.3 and $R^{3a}$ is hydrogen are also referred to as compounds of formula (I-A),

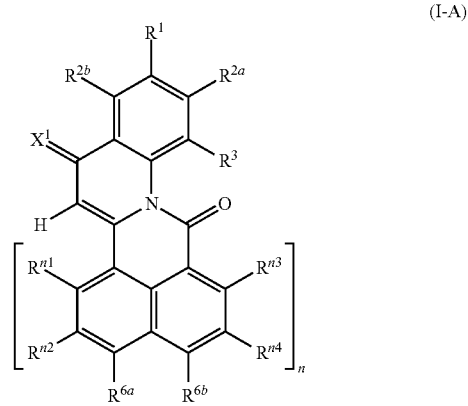

wherein $X^1$, $R^1$, $R^{2a}$, $R^{2b}$, $R^3$, $R^{n1}$, $R^{n2}$, $R^{n3}$, $R^{n4}$, $R^{6a}$, $R^{6b}$ and n are as defined above.

Compounds of the formula (I-A), where $X^1$ is O, are also referred to as compounds of formula (I-Aa).

Compounds of the formula (I-A), where $X^1$ is $C(CN)_2$, are also referred to as compounds of formula (I-Ab).

The compounds of the general formula (I), wherein group A is a radical of formula (A.3) and $R^{3a}$ is hydrogen are denoted in the following also as "group of embodiments (b) or embodiments (b)". All definitions of substituents and variables regarding the group of embodiments (b), where applicable, refer to the compounds of the general formula (I), wherein group A is a radical A.3 and $R^{3a}$ is hydrogen, the compounds of the formulae (I-A), (I-Aa) and (I-Ab).

In the compounds of the formula (I-A) according to the group of embodiments (b), $R^1$, $R^{2a}$, $R^{2b}$ and $R^3$ are as defined above and preferably have one of the preferred meanings. In particular, $R^1$ is selected from hydrogen, chlorine, bromine and branched $C_3$-$C_{10}$-alkyl. In particular $R^{2a}$, $R^{2b}$ and $R^3$ are each hydrogen. Preferably, $X^1$ is O. Likewise preferred are compounds, wherein $X^1$ is $C(CN)_2$.

Preferably, $R^{n1}$, $R^{n2}$, $R^{n3}$, $R^{n4}$, $R^{6a}$, $R^{6b}$, are independently of one another, selected from hydrogen, chlorine, bromine, iodine, $C_1$-$C_{30}$-alkoxy, $C_1$-$C_{30}$-alkylsulfanyl, aryloxy and arylthio where the two last mentioned radicals are unsubstituted or carry 1, 2 or 3 substituents selected from $SO_3H$, $C_1$-$C_{10}$-alkoxy and $C_1$-$C_{10}$-alkyl which is unsubstituted or substituted by COOH. More preferably, $R^{n1}$, $R^{n2}$, $R^{n3}$, $R^{n4}$, $R^{6a}$, $R^{6b}$, are independently of one another, selected from hydrogen, $C_1$-$C_{30}$-alkoxy, $C_1$-$C_{30}$-alkylsulfanyl, aryloxy and arylthio where the two last mentioned radicals are unsubstituted or carry 1, 2 or 3 substituents selected from $SO_3H$, $C_1$-$C_{10}$-alkoxy and $C_1$-$C_{10}$-alkyl which is unsubstituted or substituted by COOH. Most preferably, $R^{n1}$, $R^{n2}$, $R^{n3}$, $R^{n4}$, $R^{6a}$ and $R^{6b}$, are independently of one another, selected from hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. Especially, $R^{n1}$, $R^{n2}$, $R^{n3}$, $R^{n4}$, $R^{6a}$ and $R^{6b}$, are independently of one another, selected from hydrogen, phenoxy, 2,6-diisopropylphenoxy, 2,4-di-tert-butylphenoxy, 4-tert-octylphenoxy, 4-sulfophenoxy and 4-(carboxymethyl)phenoxy.

In the compounds of the formula (I-A) according to the group of embodiments (b), the $R^{6a}$ and $R^{6b}$ radicals may have identical or different definitions. In a preferred embodiment, the $R^{6a}$ and $R^{6b}$ radicals have identical definitions.

Preference is given to compounds of formula (I), wherein $R^{6a}$ and $R^{6b}$ are each hydrogen, while $R^{n1}$, $R^{n2}$, $R^{n3}$ and $R^{n4}$ are independently of one another, selected from hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH.

The variable n is preferably 1, 2 or 3, and especially 1 or 2.

According to a particular embodiment, wherein n is 1, $R^{6a}$ and $R^{6b}$ are each hydrogen and $R^{11}$, $R^{12}$, $R^{13}$ and $R^{14}$ are as defined above and in particular selected from the group consisting of hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. Especially, all of $R^{6a}$, $R^{6b}$, $R^{11}$, $R^{12}$, $R^{13}$ and $R^{14}$ are hydrogen.

According to a further particular embodiment, wherein n is 2, $R^{6a}$, $R^{6b}$, $R^{11}$, $R^{12}$, $R^{13}$, $R^{14}$, $R^{21}$, $R^{22}$, $R^{23}$ and $R^{24}$ are as defined above. In particular, $R^{6a}$, $R^{6b}$, $R^{11}$, $R^{12}$, $R^{13}$, $R^{14}$, $R^{21}$, $R^{22}$ and $R^{24}$ are selected from the group consisting of hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. More preference is given to compounds (I-A), where n=2 and $R^{6a}$, $R^{6b}$, $R^{11}$, $R^{12}$, $R^{13}$, $R^{14}$, $R^{21}$, $R^{22}$, $R^{23}$ and $R^{24}$ are each hydrogen. Likewise, more preference is given to compounds (I-A), where n=2, and 2 or 4 of the radicals $R^{11}$, $R^{12}$, $R^{13}$, $R^{14}$, $R^{21}$, $R^{22}$, $R^{23}$ and $R^{24}$ are each phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{6a}$, $R^{6b}$, $R^{11}$, $R^{12}$, $R^{13}$, $R^{14}$, $R^{21}$, $R^{22}$, $R^{23}$ and $R^{24}$ are each hydrogen. Among these compounds of formula (I-A), more preference is given to those compounds (I-A), wherein 2 or 4 of the $R^{12}$, $R^{14}$, $R^{21}$ and $R^{23}$ radicals are each phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{6a}$, $R^{6b}$, $R^{11}$, $R^{12}$, $R^{13}$, $R^{14}$, $R^{21}$, $R^{22}$, $R^{23}$ and $R^{24}$ are each hydrogen.

Some particularly preferred compounds of formula (I-A) are specified below:

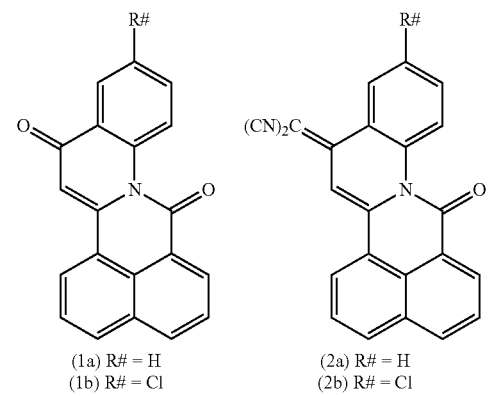

(1a) R# = H
(1b) R# = Cl (2a) R# = H
(2b) R# = Cl

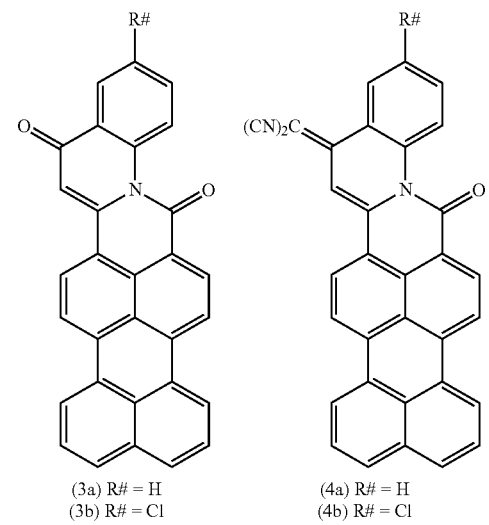

(3a) R# = H
(3b) R# = Cl (4a) R# = H
(4b) R# = Cl

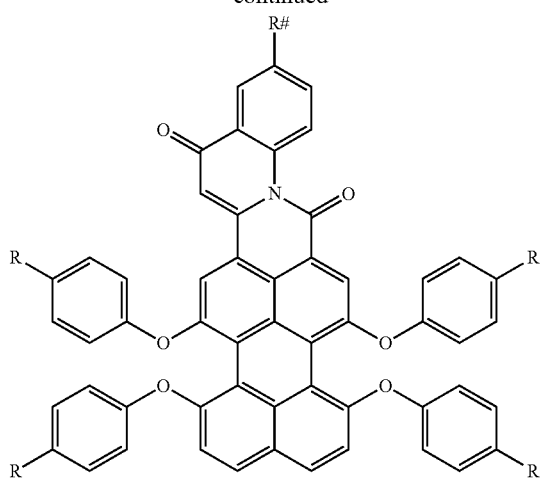

(5a) R = H; R# = H
(5b) R = SO₃H; R# = H
(5c) R = —C(CH₃)₂—CH₂—COOH; R# = H
(5d) R = CH₂COOH; R# = H
(5e) R = H; R# = Cl
(5f) R = SO₃H; R# = Cl
(5g) R = —C(CH₃)₂—CH₂—COOH; R# = Cl
(5h) R = CH₂COOH; R# = Cl
(5i) R = —C(CH₃)₂CH₂—C(CH₃)₃; R# = H
(5k) R = —C(CH₃)₂CH₂—C(CH₃)₃; R# = Cl

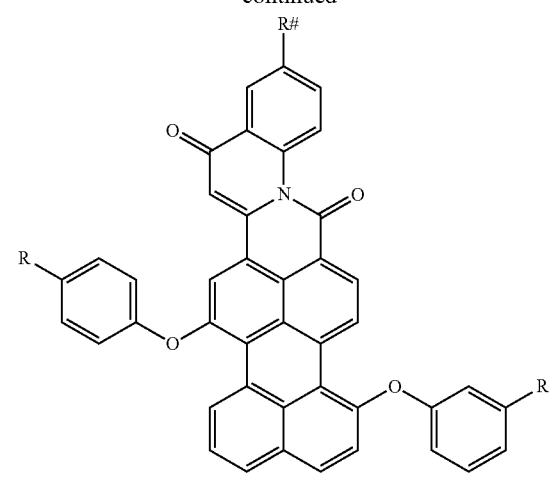

(7a) R = H; R# = H
(7b) R = SO₃H; R# = H
(7c) R = —C(CH₃)₂—CH₂—COOH; R# = H
(7d) R = CH₂COOH; R# = H
(7e) R = H; R# = Cl
(7f) R = SO₃H; R# = Cl
(7g) R = —C(CH₃)₂—CH₂—COOH; R# = Cl
(7h) R = CH₂COOH; R# = Cl
(7ii) R = —C(CH₃)₂CH₂—C(CH₃)₃; R# = H
(7k) R = —C(CH₃)₂CH₂—C(CH₃)₃; R# = Cl

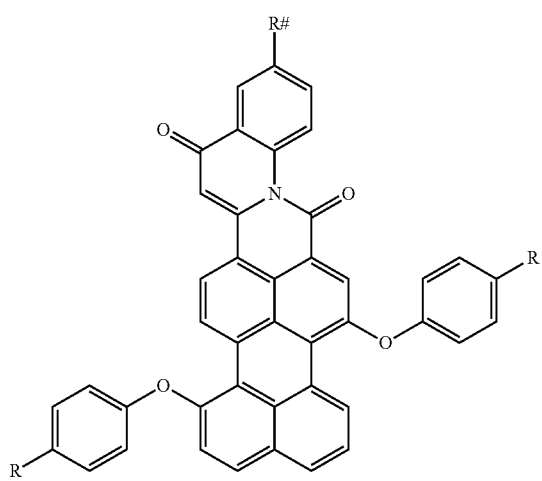

(6a) R = H; R# = H
(6b) R = SO₃H; R# = H
(6c) R = —C(CH₃)₂—CH₂—COOH; R# = H
(6d) R = CH₂COOH; R# = H
(6e) R = H; R# = Cl
(6f) R = SO₃H; R# = Cl
(6g) R = —C(CH₃)₂—CH₂—COOH; R# = Cl
(6h) R = CH₂COOH; R# = Cl
(6i) R = —C(CH₃)₂CH₂—C(CH₃)₃; R# = H
(6k) R = —C(CH₃)₂CH₂—C(CH₃)₃; R# = Cl

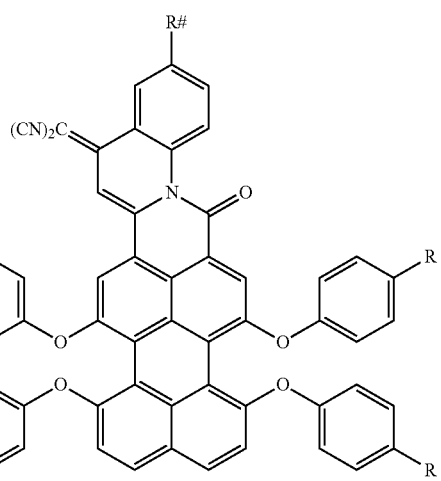

(8a) R = H; R# = H
(8b) R = SO₃H; R# = H
(8c) R = —C(CH₃)₂—CH₂—COOH; R# = H
(8d) R = CH₂COOH; R# = H
(8e) R = H; R# = Cl
(8f) R = SO₃H; R# = Cl
(8g) R = —C(CH₃)₂—CH₂—COOH; R# = Cl
(8h) R = CH₂COOH; R# = Cl
(8i) R = —C(CH₃)₂CH₂—C(CH₃)₃; R# = H
(8k) R = —C(CH₃)₂CH₂—C(CH₃)₃; R# = Cl

-continued

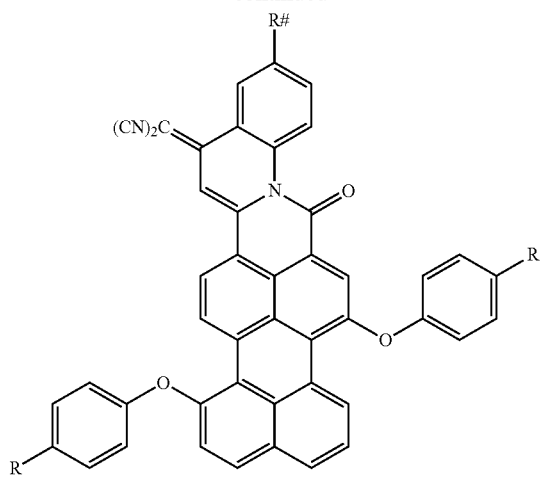

(9a) R = H; R# = H
(9b) R = SO₃H; R# = H
(9c) R = —C(CH₃)₂—CH₂—COOH; R# = H
(9d) R = CH₂COOH; R# = H
(9e) R = H; R# = Cl
(9f) R = SO₃H; R# = Cl
(9g) R = —C(CH₃)₂—CH₂—COOH; R# = Cl
(9h) R = CH₂COOH; R# = Cl
(9i) R = —C(CH₃)₂CH₂—C(CH₃)₃; R# = H
(9k) R = —C(CH₃)₂CH₂—C(CH₃)₃; R# = Cl

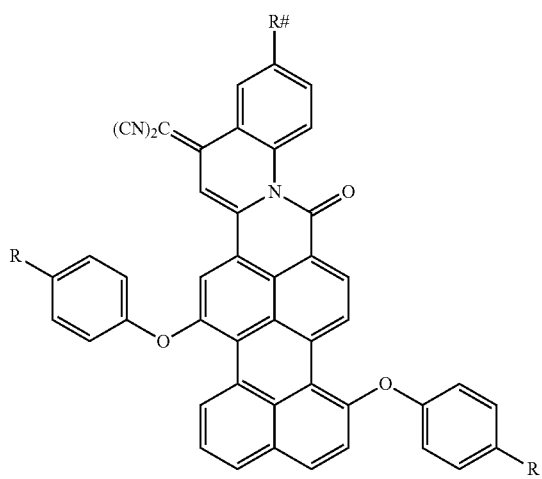

(10a) R = H; R# = H
(10b) R = SO₃H; R# = H
(10c) R = —C(CH₃)₂—CH₂—COOH; R# = H
(10d) R = CH₂COOH; R# = H
(10e) R = H; R# = Cl
(10f) R = SO₃H; R# = Cl
(10g) R = —C(CH₃)₂—CH₂—COOH; R# = Cl
(10h) R = CH₂COOH; R# = Cl
(10i) R = —C(CH₃)₂CH₂—C(CH₃)₃; R# = H
(10k) R = —C(CH₃)₂CH₂—C(CH₃)₃; R# = Cl

-continued

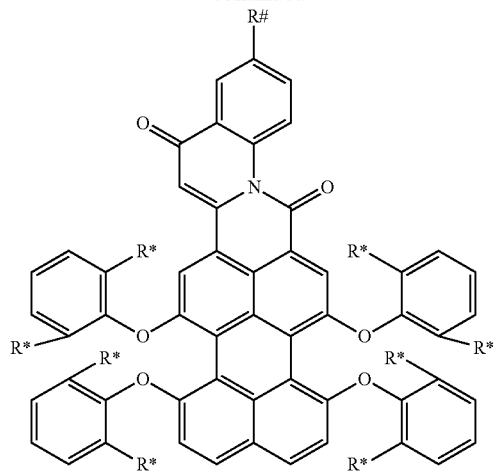

(11a) R* = CH(CH₃)₂; R# = H
(11b) R* = CH(CH₃)₂; R# = Cl

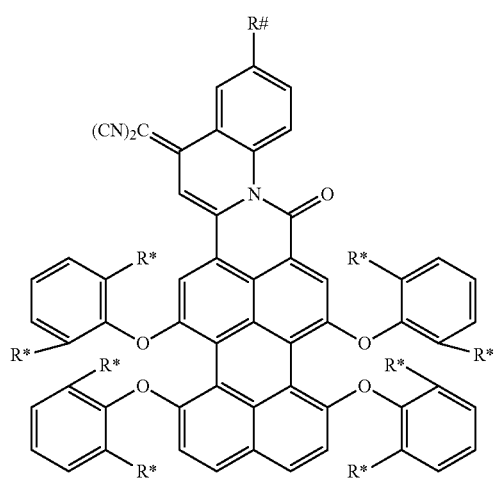

(12a) R* = CH(CH₃)₂; R# = H
(12b) R* = CH(CH₃)₂; R# = Cl

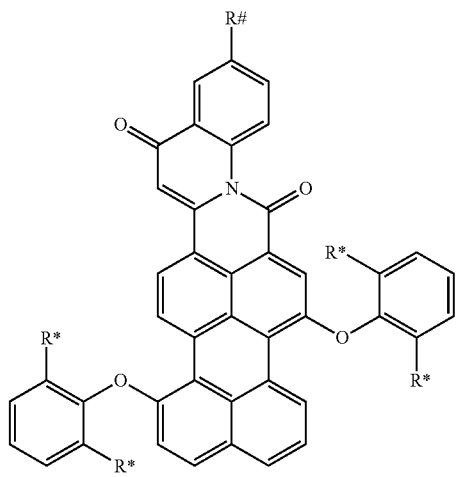

(13a) R* = CH(CH₃)₂; R# = H
(13b) R* = CH(CH₃)₂; R# = Cl

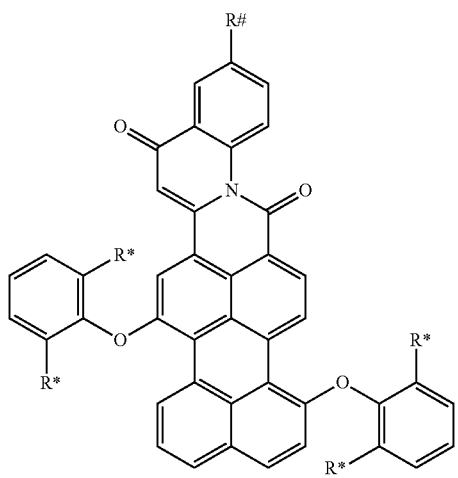
(14a) R* = CH(CH₃)₂; R# = H
(14b) R* = CH(CH₃)₂; R# = Cl
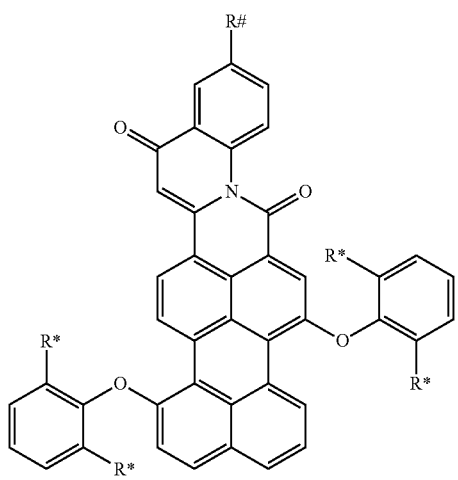
(15a) R* = CH(CH₃)₂; R# = H
(15b) R* = CH(CH₃)₂; R# = Cl
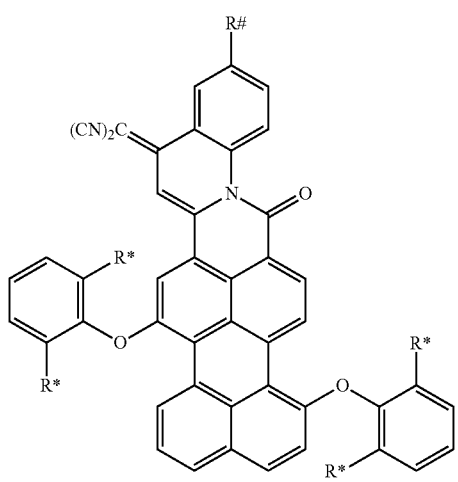
(16a) R* = CH(CH₃)₂; R# = H
(16b) R* = CH(CH₃)₂; R# = Cl
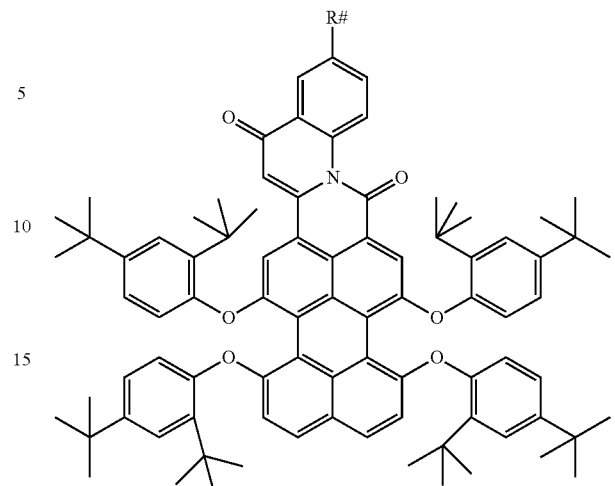
(17a) R# = H
(17b) R# = Cl
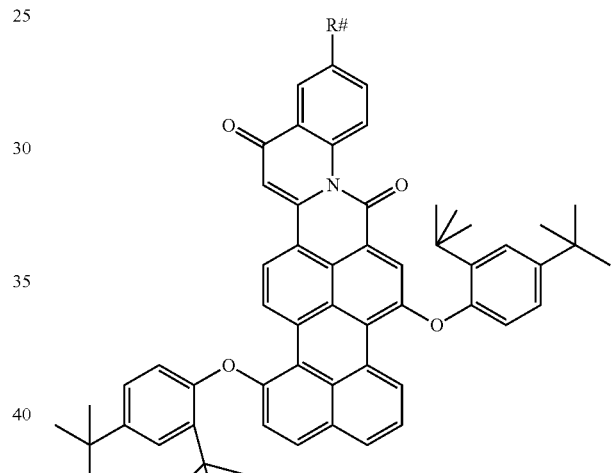
(18a) R# = H
(18b) R# = Cl
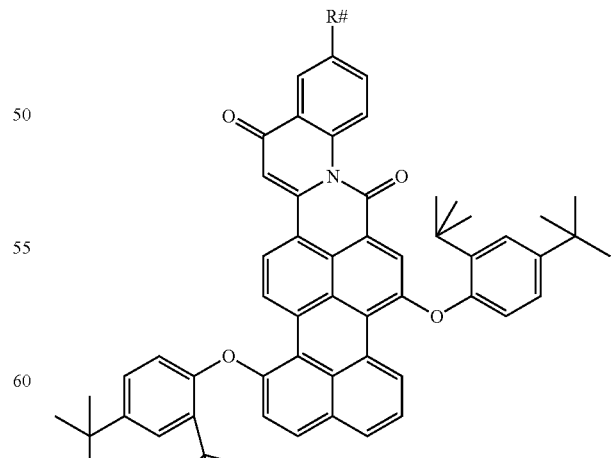
(19a) R# = H
(19b) R# = Cl -continued

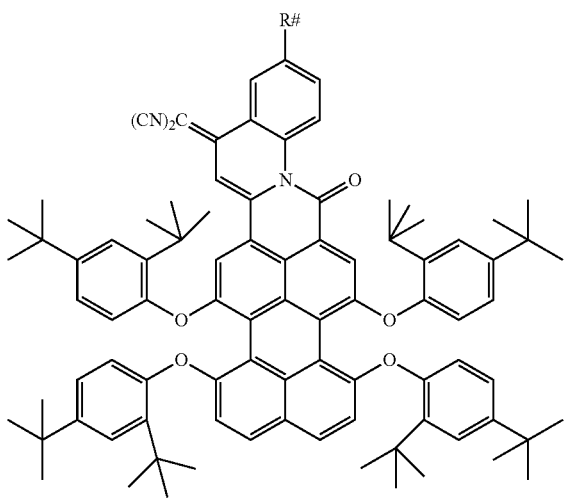

(20a) R# = H
(20b) R# = Cl

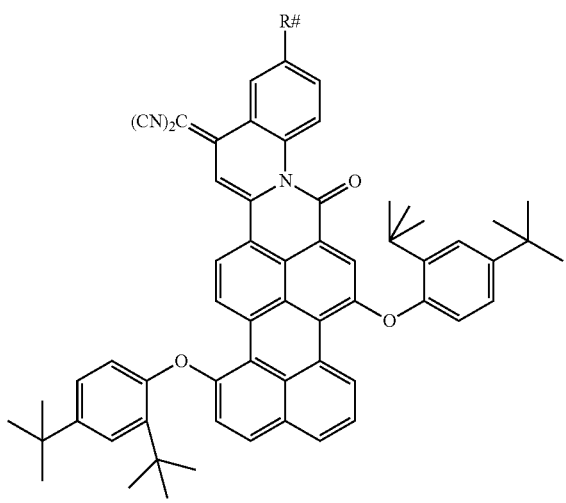

(21a) R# = H
(21b) R# = Cl

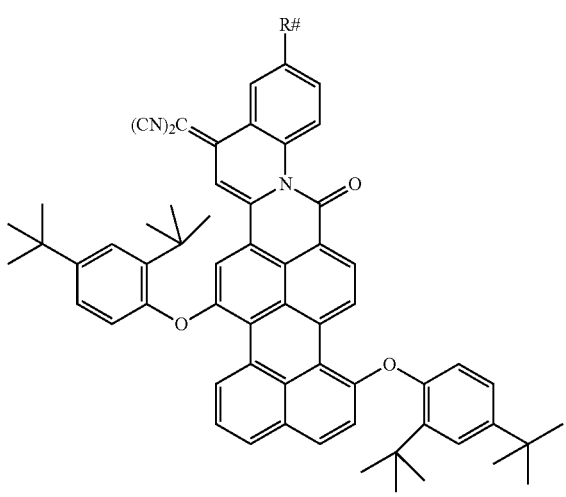

(22a) R# = H
(22b) R# = Cl

In a particularly preferred embodiment, the compounds of the general formula (I) are selected from compounds of the formula (I-A).

The enlargement of the conjugated system of the compound of formula (I-A) results in a bathochrome shift towards the respective naphthalene monoimide and rylene monoimide, respectively.

Embodiments (c)

According to a third group of embodiments, compounds of formula (I) are preferred, wherein A is a radical of the formula (A.6), $R^{3a}$ is hydrogen and $R^{9a}$ is hydrogen. A skilled person will readily appreciate that the compounds of this embodiment (c) may be present in form of the syn-isomer or in the form of the anti-isomer or as a mixture of syn- and anti-isomers with regard to the carbonyl group of the imide unit. A compound of the formula (I), where A is a radical of the formula (A.6), $R^{3a}$ is hydrogen and $R^{9a}$ is hydrogen and where the carbonyl groups of the imide units are on the opposite side of the ring system, is called the anti-isomer and, in the following, is referred to as a compound of formula (I-B). A compound of the formula (I), where A is a radical of the formula (A.6), $R^{3a}$ is hydrogen and $R^{9a}$ is hydrogen and where the carbonyl groups of the imide unit are on the same side of the ring system, is called the syn-isomer and, in the following, is referred to as a compound of formula (I-C). The embodiment (c) includes the pure anti-isomer of the formula (I-B), the pure syn-isomer of the formula (I-C) as well as mixtures of these isomers

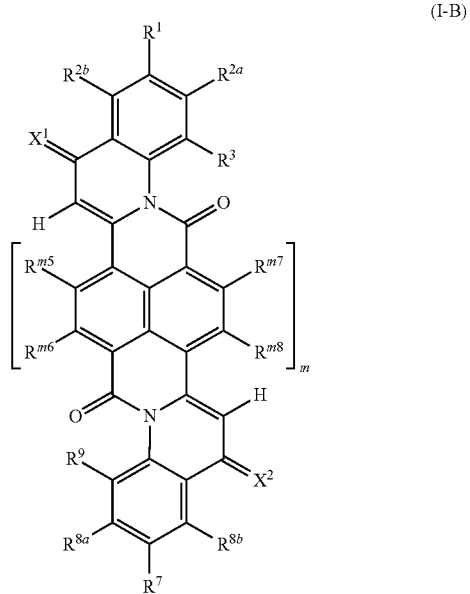

(I-B)

-continued (I-C)

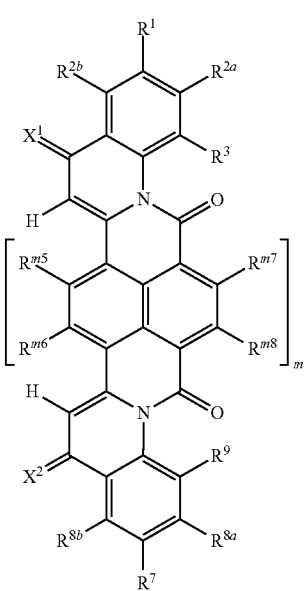

wherein $X^1$, $X^2$, $R^1$, $R^{2a}$, $R^{2b}$, $R^3$, $R^{m5}$, $R^{m6}$, $R^{m7}$, $R^{m8}$, $R^7$, $R^{8a}$, $R^{8b}$, $R^9$ and m are as defined above.

Compounds of the formula (I-B), wherein $X^1$ and $X^2$ are both O, are also referred to as compounds (I-Ba). Compounds of the formula (I-B), wherein $X^1$ and $X^2$ are both $C(CN)_2$, are also referred to as compounds (I-Bb).

Compounds of the formula (I-C), wherein $X^1$ and $X^2$ are both O, are also referred to as compounds (I-Ca). Compounds of the formula (I-C), wherein $X^1$ and $X^2$ are both $C(CN)_2$, are also referred to as compounds (I-Cb).

The compounds of the general formula (I), wherein group A is a radical of formula (A.6), $R^{3a}$ is hydrogen and $R^{9a}$ is hydrogen, are denoted in the following also as "group of embodiments (c) or embodiments (c)". All definitions of substituents and variables regarding the group of embodiments (c), where applicable, refer to the compounds of the general formula (I), wherein group A is a radical (A.6), $R^{3a}$ is hydrogen and $R^{9a}$ is hydrogen, the compounds of the formulae (I-B), (I-Ba), (I-Bb) and the compounds of the formulae (I-C), (I-Ca), (I-Cb).

In the compounds of the formulae (I-B) and (I-C) according to the group of embodiments (c), $R^1$, $R^{2a}$, $R^{2b}$ and $R^3$ are as defined above and preferably have one of the preferred meanings. In particular, $R^1$ is selected from hydrogen, chlorine, bromine and branched $C_3$-$C_{10}$-alkyl. In particular $R^{2a}$, $R^{2b}$ and $R^3$ are each hydrogen.

In the compounds of the formulae (I-B) and (I-C) according to the group of embodiments (c), preferably, the radicals $R^7$, $R^{8a}$, $R^{8b}$ are, independently of one another, selected from hydrogen, chlorine, bromine, linear $C_1$-$C_{30}$-alkyl, branched $C_3$-$C_{30}$-alkyl, $C_1$-$C_{30}$-haloalkyl, a radical of the formula (G.1), a radical of the formula (G.2) and a radical of the formula (G.3)

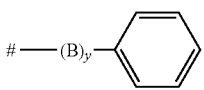
(G.1)

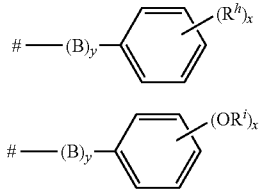
(G.2)

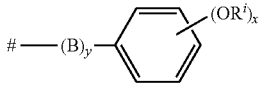
(G.3)

where
\# represents the bonding side to the remainder of the molecule;
B if present, is selected from O, S and a $C_1$-$C_{10}$-alkylene group which may be interrupted by one or more nonadjacent groups which are selected from O and S;
y is 0 or 1;
$R^h$ is independently of one another selected from $C_1$-$C_{30}$-alkyl, $C_1$-$C_{30}$-fluoroalkyl, fluorine, chlorine, bromine, $NE^3E^4$, nitro, $SO_3H$ and cyano, where $E^3$ and $E^4$, independently of one another, are hydrogen, alkyl, cycloalkyl, heterocycloalkyl, aryl or hetaryl;
$R^i$ is independently of one another selected from $C_1$-$C_{30}$-alkyl;
x in formulae G.2 and G.3 is 1, 2, 3, 4 or 5.

If B is present, i.e. if y is 1, the variable B is preferably O or a $C_1$-$C_{10}$-alkylene group.

Irrespectively of its occurrence, $R^h$ is preferably selected from $C_1$-$C_{30}$-alkyl. Irrespectively of its occurrence, $R^i$ is preferably selected from $C_1$-$C_{30}$-alkyl.

The $R^{8a}$ and $R^{8b}$ radicals may have identical or different definitions. In a preferred embodiment, the $R^{8a}$ and $R^{8b}$ radicals have identical definitions. Especially, $R^9$ is hydrogen.

The radical $R^7$ is preferably selected from hydrogen, chlorine, bromine, $C_1$-$C_{30}$-alkyl and $C_1$-$C_{30}$-haloalkyl. More preferably, $R^7$ is selected from hydrogen, chlorine, bromine, linear $C_1$-$C_{30}$-alkyl, branched $C_3$-$C_{30}$-alkyl, perfluoro-$C_1$-$C_{30}$-alkyl, 1H, 1H-perfluoro-$C_2$-$C_{30}$-alkyl; and 1H, 1H, 2H, 2H-perfluoro-$C_3$-$C_{30}$-alkyl.

In particular, $R^7$ is selected from
hydrogen;
chlorine, bromine;
methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl;
branched $C_3$-$C_{30}$-alkyl, selected from a radical of the general formulae (III.1) and (III.2)

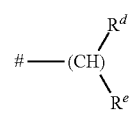
(III.1)

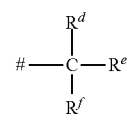
(III.2)

in which \# is a bonding site to the remainder of the molecule, and
in the formula (III.1) $R^d$ and $R^e$ are independently selected from $C_1$- to $C_{28}$-alkyl, where the sum of the carbon atoms of the $R^d$ and $R^e$ radicals is an integer from 2 to 29, in the formula (III.2) $R^d$, $R^e$ and $R^f$ are independently selected from $C_1$- to $C_{27}$-alkyl, where the sum of the carbon atoms of the $R^d$, $R^e$ and $R^f$ radicals is an integer from 3 to 29;

$CF_3$, $C_2F_5$, n-$C_3F_7$, n-$C_4F_9$, n-$C_5F_{11}$, n-$C_6F_{13}$, $CF(CF_3)_2$, $C(CF_3)_3$, $CF_2CF(CF_3)_2$, $CF(CF_3)(C_2F_5)$;

$CH_2$—$CF_3$, $CH_2$—$C_2F_5$, $CH_2$-(n-$C_3F_7$), $CH_2$-(n-$C_4F_9$), $CH_2$-(n-$C_5F_{11}$), $CH_2$-(n-$C_6F_{13}$), $CH_2$—$CF(CF_3)_2$, $CH_2$—$C(CF_3)_3$, $CH_2$—$CF_2CF(CF_3)_2$, $CH_2$—$CF(CF_3)(C_2F_5)$; and $CH_2$—$CH_2$—$CF_3$, $CH_2$—$CH_2$—$C_2F_5$, $CH_2$—$CH_2$-(n-$C_3F_7$), $CH_2$—$CH_2$-(n-$C_4F_9$), $CH_2$—$CH_2$-(n-$C_5F_{11}$), $CH_2$—$CH_2$-(n-$C_6F_{13}$), $CH_2$—$CH_2$—$CF(CF_3)_2$, $CH_2$—$CH_2$—$C(CF_3)_3$, $CH_2$—$CH_2$—$CF_2CF(CF_3)_2$ and $CH_2$—$CH_2$—$CF(CF_3)(C_2F_5)$.

In the context of the formulae (III.1) and (III.2), preferably, the $R^d$, $R^e$ and $R^f$ radicals are independently selected from $C_1$- to $C_{12}$-alkyl, especially $C_1$- to $C_8$-alkyl.

Examples of preferred radicals of the formula (III.1) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

A suitable radical of the formula (III.2) is tert.-butyl.

In a specially preferred embodiment, the radical $R^7$ is selected from hydrogen, chlorine, linear $C_1$-$C_{10}$-alkyl, a radical of the formulae (III.1) or (III.2).

Even more preferably, $R^7$ is selected from hydrogen, chlorine, bromine and branched $C_3$-$C_{10}$-alkyl. Preferably, branched $C_3$-$C_{10}$-alkyl is a radical of the formulae (III.1) or (III.2).

In this group of embodiments (c), $R^{8a}$, $R^{8b}$ and $R^9$ are preferably each hydrogen.

Preferably, $X^1$ and $X^2$ are both O or both $C(CN)_2$.

In the compounds of the formulae (I-B) and (I-C) according to the group of embodiments (c), the radicals $R^1$ and $R^7$ may have identical or different definitions. Preferably, $R^1$ and $R^7$ are, independently of one another, selected from hydrogen, chlorine, bromine, $C_1$-$C_{30}$-alkyl and $C_1$-$C_{30}$-haloalkyl. More preferably, the $R^1$ and $R^7$ radicals have identical definitions. In particular, $R^1$ and $R^7$ are selected from hydrogen, chlorine, bromine and branched $C_3$-$C_{10}$-alkyl.

In the compounds of the formulae (I-B) and (I-C) according to the group of embodiments (c), the radicals $R^{8a}$, $R^{8b}$, $R^{2a}$ and $R^{2b}$ may have identical or different definitions. Preferably, the radicals $R^{8a}$, $R^{8b}$, $R^{2a}$ and $R^{2b}$ have identical definitions. In the compounds of the formulae (I-B) and (I-C) according to the group of embodiments (c), $R^3$ and $R^9$ may have identical or different definitions. Preferably, $R^3$ and $R^9$ have identical definitions. In particular, $R^{2a}$, $R^{2b}$, $R^3$, $R^{8a}$, $R^{8b}$ and $R^9$ are each hydrogen.

Preferably, $R^{m5}$, $R^{m6}$, $R^{m7}$ and $R^{m8}$ are, independently of one another, selected from hydrogen, $C_1$-$C_{30}$-alkoxy, $C_1$-$C_{30}$-alkylsulfanyl, aryloxy and arylthio where the two last mentioned radicals are unsubstituted or carry 1, 2 or 3 substituents selected from $SO_3H$, $C_1$-$C_{10}$-alkoxy and $C_1$-$C_{10}$-alkyl which is unsubstituted or substituted by COOH. More preferably, $R^{m5}$, $R^{m6}$, $R^{m7}$ and $R^{m8}$ are, independently of one another, selected from hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. Most preferably, $R^{m5}$, $R^{m6}$, $R^{m7}$ and $R^{m8}$ are independently of one another, selected from hydrogen, phenoxy, 2,6-diisopropylphenoxy, 2,4-di-tert-butylphenoxy, 4-tert-octylphenoxy, 4-sulfophenoxy and 4-(carboxymethyl)phenoxy.

The variable m is preferably 1, 2 or 3, and especially 1 or 2. In particular, m is 2.

According to a particular embodiment, m is 1 and $R^{15}$, $R^{16}$, $R^{17}$ and $R^{18}$ are as defined above and in particular selected from the group consisting of hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH.

According to a further particular embodiment, m is 2, and $R^{15}$, $R^{16}$, $R^{17}$, $R^{18}$, $R^{25}$, $R^{26}$, $R^{27}$ and $R^{28}$ are as defined above and in particular selected from the group consisting of hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. More preferably, m=2 and $R^{15}$, $R^{16}$, $R^{17}$, $R^{18}$, $R^{25}$, $R^{26}$, $R^{27}$ and $R^{28}$ are each hydrogen. Likewise, more preferably where m=2, and 2 or 4 of the radicals $R^{15}$, $R^{16}$, $R^{17}$, $R^{18}$, $R^{25}$, $R^{26}$, $R^{27}$ and $R^{28}$ are selected from phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{15}$, $R^{16}$, $R^{17}$, $R^{18}$, $R^{25}$, $R^{26}$, $R^{27}$ and $R^{28}$ are each hydrogen. In particular, 2 or 4 of the $R^{16}$, $R^{18}$, $R^{25}$ and $R^{27}$ radicals are phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{15}$, $R^{16}$, $R^{17}$, $R^{18}$, $R^{25}$, $R^{26}$, $R^{27}$ and $R^{28}$ are each hydrogen.

According to a further particular embodiment, m is 3, and $R^{15}$, $R^{16}$, $R^{17}$, $R^{18}$, $R^{25}$, $R^{26}$, $R^{27}$ $R^{28}$, $R^{35}$, $R^{36}$, $R^{37}$ and $R^{38}$ are as defined above and in particular selected from the group consisting of hydrogen, $C_1$-$C_{30}$-alkoxy, $C_1$-$C_{30}$-alkylsulfanyl, phenyloxy and phenylthio, where the two last mentioned radicals are unsubstituted or carry 1, 2 or 3 substituents selected from $SO_3H$, $C_1$-$C_{10}$-alkoxy, $C_1$-$C_{10}$-alkyl and $C_1$-$C_{10}$-alkyl substituted by COOH. More preferably, $R^{15}$, $R^{16}$, $R^{17}$, $R^{18}$, $R^{25}$, $R^{26}$, $R^{27}$, $R^{28}$, $R^{35}$, $R^{36}$, $R^{37}$ and $R^{38}$ are each hydrogen. Likewise, more preferably $R^{25}$, $R^{26}$, $R^{27}$ and $R^{28}$ are each hydrogen and 2 or 4 of the radicals $R^{15}$, $R^{16}$, $R^{17}$, $R^{18}$, $R^{35}$, $R^{36}$, $R^{37}$ and $R^{38}$ are selected from phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{15}$, $R^{16}$, $R^{17}$, $R^{18}$, $R^{35}$, $R^{36}$, $R^{37}$ and $R^{38}$ are each hydrogen. In particular, 2 or 4 of the $R^{16}$, $R^{18}$, $R^{35}$ and $R^{37}$ radicals are phenyloxy which is unsubstituted or substituted by 1, 2 or 3 substituents selected from $SO_3H$, $C_1$-$C_{10}$-alkoxy and $C_1$-$C_{10}$-alkyl which is unsubstituted or substituted by COOH and the remaining radicals $R^{15}$, $R^{16}$, $R^{17}$, $R^{18}$, $R^{35}$, $R^{36}$, $R^{37}$ and $R^{38}$ are each hydrogen and $R^{25}$, $R^{26}$, $R^{27}$ and $R^{28}$ are each hydrogen.

Some particularly preferred compounds of formulae (I-B) and (I-C) are specified below:
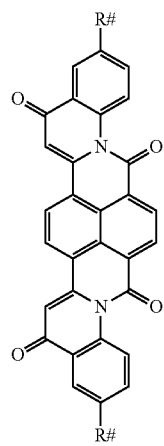 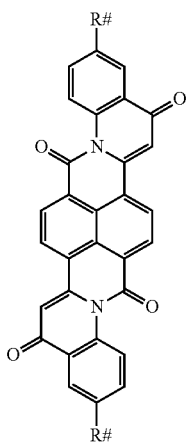 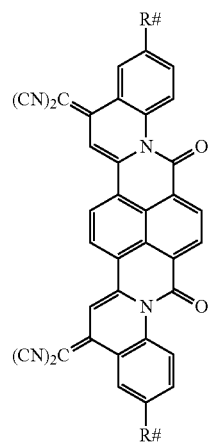 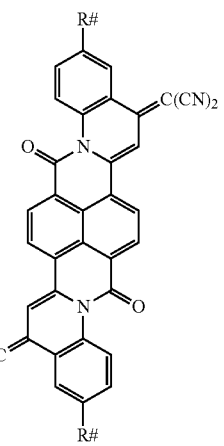
(23a) R# = H
(23b) R# = Cl
(24a) R# = H
(24b) R# = Cl
(25a) R# = H
(25b) R# = Cl
(26a) R# = H
(26b) R# = Cl
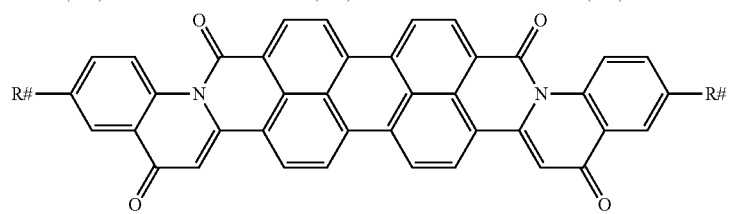
(27a) R# = H
(27b) R# = Cl
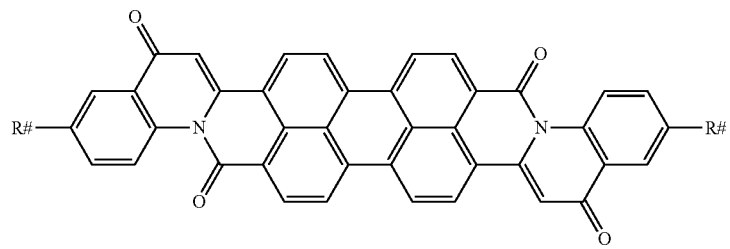
(28a) R# = H
(28b) R# = Cl
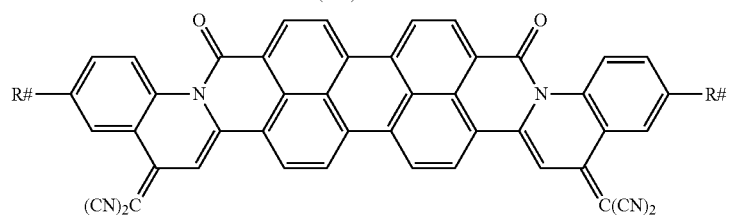
(29a) R# = H
(29b) R# = Cl
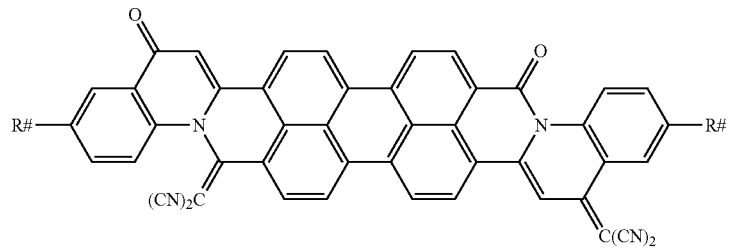
(30a) R# = H
(30b) R# = Cl -continued

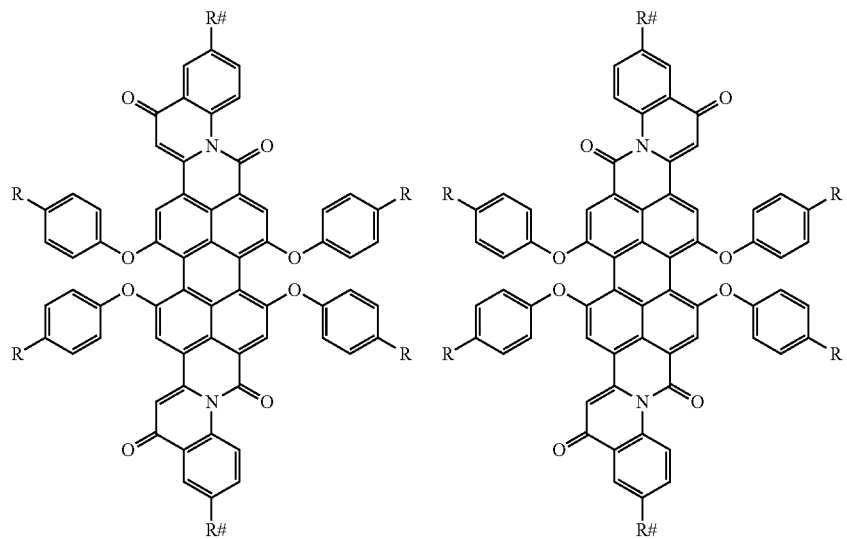

(31a) R = H; R# = H
(31b) R = SO₃H; R# = H
(31c) R = —C(CH₃)₂—CH₂—COOH; R# = H
(31d) R = CH₂COOH; R# = H
(31e) R = H; R# = Cl
(31f) R = SO₃H; R# = Cl
(31g) R = —C(CH₃)₂—CH₂—COOH; R# = Cl
(31h) R = CH₂COOH; R# = Cl
(31i) R = —C(CH₃)₂CH₂—C(CH₃)₃; R# = H
(31k) R = —C(CH₃)₂CH₂—C(CH₃)₃; R# = Cl (32a) R = H; R# = H
(32b) R = SO₃H; R# = H
(32c) R = —C(CH₃)₂—CH₂—COOH; R# = H
(32d) R = CH₂COOH; R# = H
(32e) R = H; R# = Cl
(32f) R = SO₃H; R# = Cl
(32g) R = —C(CH₃)₂—CH₂—COOH; R# = Cl
(32h) R = CH₂COOH; R# = Cl
(32i) R = —C(CH₃)₂CH₂—C(CH₃)₃; R# = H
(32k) R = —C(CH₃)₂CH₂—C(CH₃)₃; R# = Cl

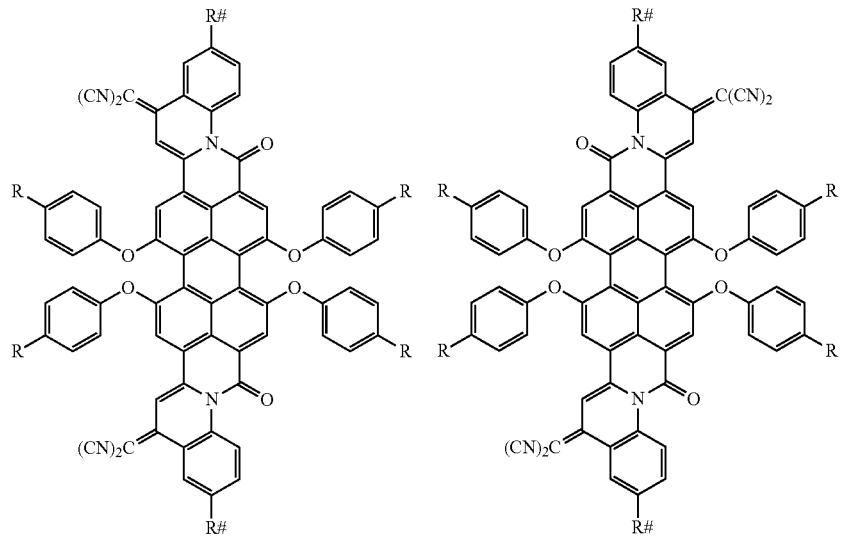

(33a) R = H; R# = H
(33b) R = SO₃H; R# = H
(33c) R = —C(CH₃)₂—CH₂—COOH; R# = H
(33d) R = CH₂COOH; R# = H
(33e) R = H; R# = Cl
(33f) R = SO₃H; R# = Cl
(33g) R = —C(CH₃)₂—CH₂—COOH; R# = Cl
(33h) R = CH₂COOH; R# = Cl
(33i) R = —C(CH₃)₂CH₂—C(CH₃)₃; R# = H
(33k) R = —C(CH₃)₂CH₂—C(CH₃)₃; R# = Cl (34a) R = H; R# = H
(34b) R = SO₃H; R# = H
(34c) R = —C(CH₃)₂—CH₂—COOH; R# = H
(34d) R = CH₂COOH; R# = H
(34e) R = H; R# = Cl
(34f) R = SO₃H; R# = Cl
(34g) R = —C(CH₃)₂—CH₂—COOH; R# = Cl
(34h) R = CH₂COOH; R# = Cl
(34i) R = —C(CH₃)₂CH₂—C(CH₃)₃; R# = H
(34k) R = —C(CH₃)₂CH₂—C(CH₃)₃; R# = Cl

-continued

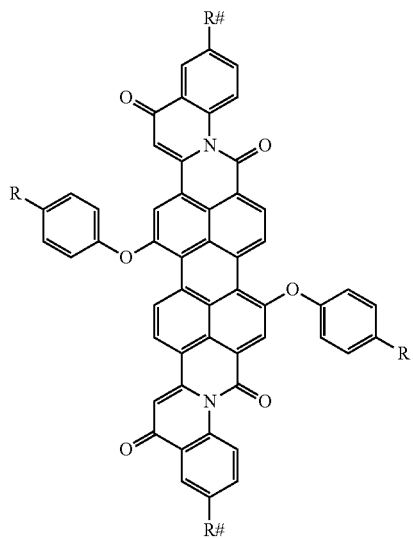

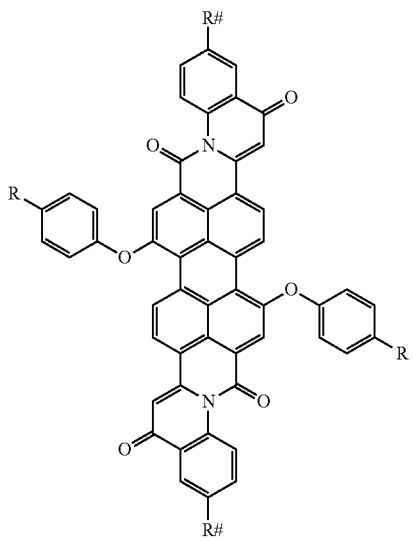

(35a) R = H; R# = H
(35b) R = SO$_3$H; R# = H
(35c) R = —C(CH$_3$)$_2$—CH$_2$—COOH; R# = H
(35d) R = CH$_2$COOH; R# = H
(35e) R = H; R# = Cl
(35f) R = SO$_3$H; R# = Cl
(35g) R = —C(CH$_3$)$_2$—CH$_2$—COOH; R# = Cl
(35h) R = CH$_2$COOH; R# = Cl
(35i) R = —C(CH$_3$)$_2$CH$_2$—C(CH$_3$)$_3$; R# = H
(35k) R = —C(CH$_3$)$_2$CH$_2$—C(CH$_3$)$_3$; R# = Cl (36a) R = H; R# = H
(36b) R = SO$_3$H; R# = H
(36c) R = —C(CH$_3$)$_2$—CH$_2$—COOH; R# = H
(36d) R = CH$_2$COOH; R# = H
(36e) R = H; R# = Cl
(36f) R = SO$_3$H; R# = Cl
(36g) R = —C(CH$_3$)$_2$—CH$_2$—COOH; R# = Cl
(36h) R = CH$_2$COOH; R# = Cl
(36i) R = —C(CH$_3$)$_2$CH$_2$—C(CH$_3$)$_3$; R# = H
(36k) R = —C(CH$_3$)$_2$CH$_2$—C(CH$_3$)$_3$; R# = Cl

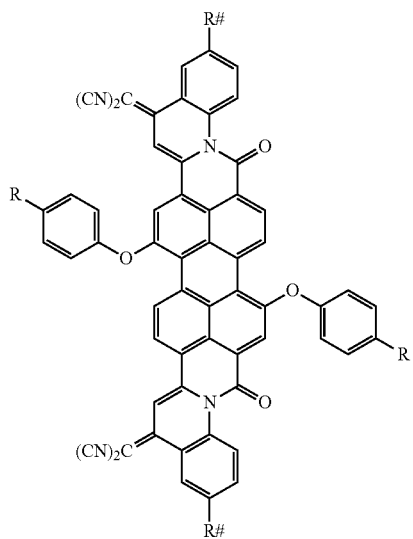

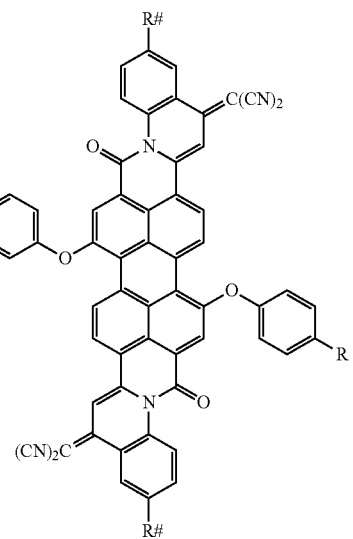

(37a) R = H; R# = H
(37b) R = SO$_3$H; R# = H
(37c) R = —C(CH$_3$)$_2$—CH$_2$—COOH; R# = H
(37d) R = CH$_2$COOH; R# = H
(37e) R = H; R# = Cl
(37f) R = SO$_3$H; R# = Cl
(37g) R = —C(CH$_3$)$_2$—CH$_2$—COOH; R# = Cl
(37h) R = CH$_2$COOH; R# = Cl
(37i) R = —C(CH$_3$)$_2$CH$_2$—C(CH$_3$)$_3$; R# = H
(37k) R = —C(CH$_3$)$_2$CH$_2$—C(CH$_3$)$_3$; R# = Cl (38a) R = H; R# = H
(38b) R = SO$_3$H; R# = H
(38c) R = —C(CH$_3$)$_2$—CH$_2$—COOH; R# = H
(38d) R = CH$_2$COOH; R# = H
(38e) R = H; R# = Cl
(38f) R = SO$_3$H; R# = Cl
(38g) R = —C(CH$_3$)$_2$—CH$_2$—COOH; R# = Cl
(38h) R = CH$_2$COOH; R# = Cl
(38i) R = —C(CH$_3$)$_2$CH$_2$—C(CH$_3$)$_3$; R# = H
(38k) R = —C(CH$_3$)$_2$CH$_2$—C(CH$_3$)$_3$; R# = Cl

-continued

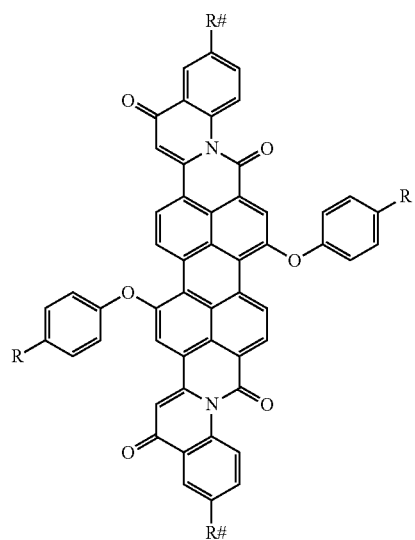
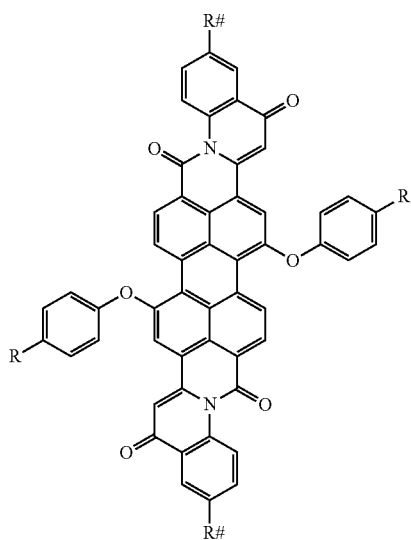

(39a) R = H; R# = H
(39b) R = SO₃H; R# = H
(39c) R = —C(CH₃)₂—CH₂—COOH; R# = H
(39d) R = CH₂COOH; R# = H
(39e) R = H; R# = Cl
(39f) R = SO₃H; R# = Cl
(39g) R = —C(CH₃)₂—CH₂—COOH; R# = Cl
(39h) R = CH₂COOH; R# = Cl
(39i) R = —C(CH₃)₂CH₂—C(CH₃)₃; R# = H
(39k) R = —C(CH₃)₂CH₂—C(CH₃)₃; R# = Cl (40a) R = H; R# = H
(40b) R = SO₃H; R# = H
(40c) R = —C(CH₃)₂—CH₂—COOH; R# = H
(40d) R = CH₂COOH; R# = H
(40e) R = H; R# = Cl
(40f) R = SO₃H; R# = Cl
(40g) R = —C(CH₃)₂—CH₂—COOH; R# = Cl
(40h) R = CH₂COOH; R# = Cl
(40i) R = —C(CH₃)₂CH₂—C(CH₃)₃; R# = H
(40k) R = —C(CH₃)₂CH₂—C(CH₃)₃; R# = Cl

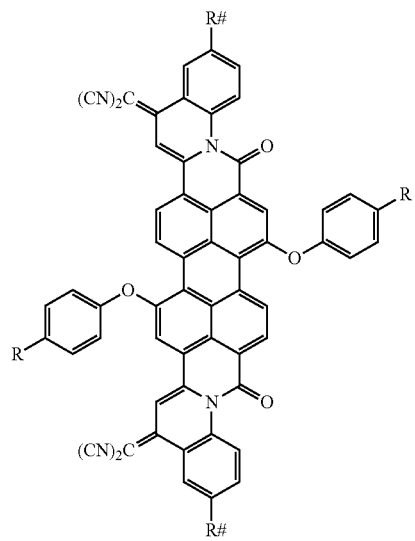
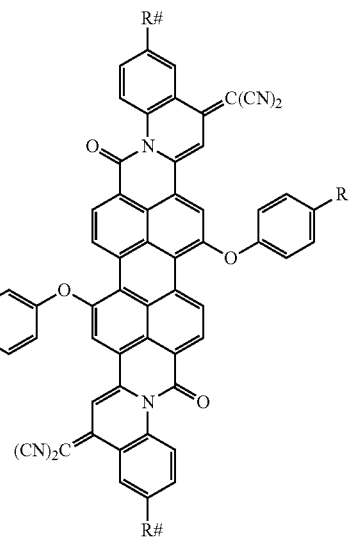

(41a) R = H; R# = H
(41b) R = SO₃H; R# = H
(41c) R = —C(CH₃)₂—CH₂—COOH; R# = H
(41d) R = CH₂COOH; R# = H
(41e) R = H; R# = Cl
(41f) R = SO₃H; R# = Cl
(41g) R = —C(CH₃)₂—CH₂—COOH; R# = Cl
(41h) R = CH₂COOH; R# = Cl
(41i) R = —C(CH₃)₂CH₂—C(CH₃)₃; R# = H
(41k) R = —C(CH₃)₂CH₂—C(CH₃)₃; R# = Cl (42a) R = H; R# = H
(42b) R = SO₃H; R# = H
(42c) R = —C(CH₃)₂—CH₂—COOH; R# = H
(42d) R = CH₂COOH; R# = H
(42e) R = H; R# = Cl
(42f) R = SO₃H; R# = Cl
(42g) R = —C(CH₃)₂—CH₂—COOH; R# = Cl
(42h) R = CH₂COOH; R# = Cl
(42i) R = —C(CH₃)₂CH₂—C(CH₃)₃; R# = H
(42k) R = —C(CH₃)₂CH₂—C(CH₃)₃; R# = Cl

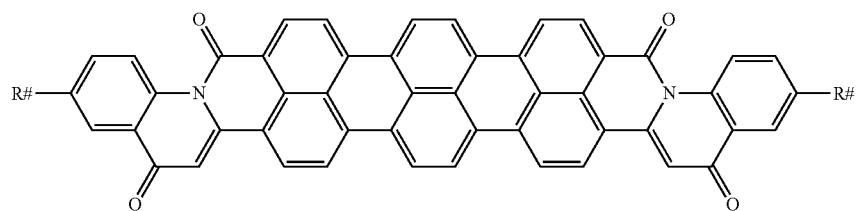
(43a) R# = H
(43b) R# = Cl
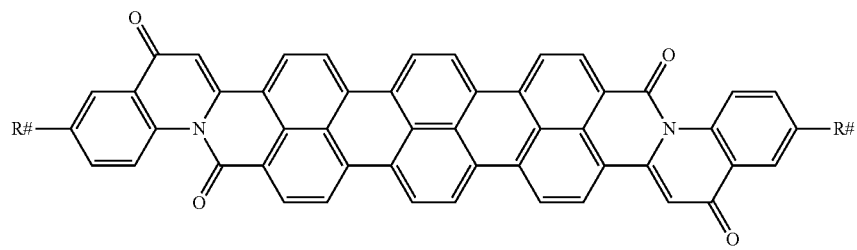
(44a) R# = H
(44b) R# = Cl
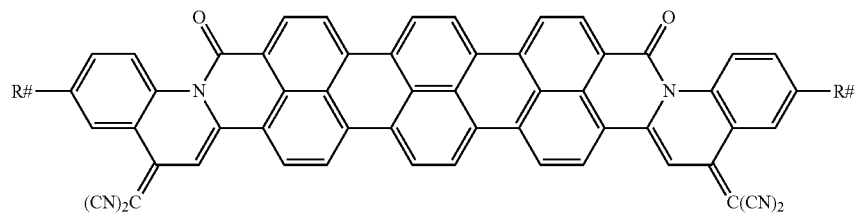
(45a) R# = H
(45b) R# = Cl
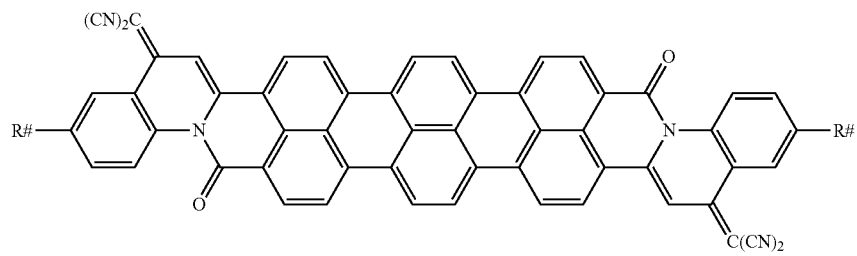
(46a) R# = H
(46b) R# = Cl
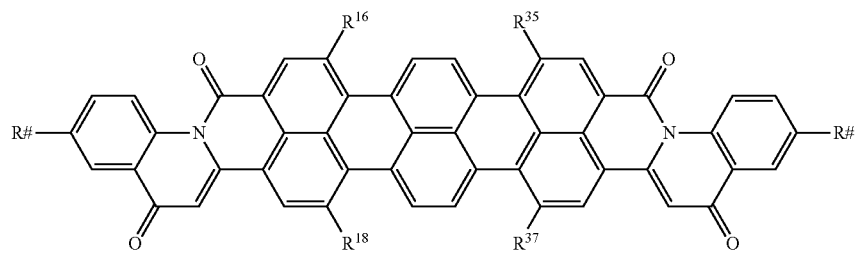
(47a) $R^{16} = R^{18} = R^{37}$ = phenoxy; R# = H;
(47b) $R^{16} = R^{18} = R^{35} = R^{37}$ = 4-sulfophenoxy; R# = H;
(47c) $R^{16} = R^{18} = R^{35} = R^{37}$ = 4-(—C(CH$_3$)$_2$—CH$_2$—COOH)-phenoxy; R# = H
(47d) $R^{16} = R^{18} = R^{35} = R^{37}$ = 4-(—CH$_2$—COOH)-phenoxy; R# = H
(47e) $R^{16} = R^{18} = R^{35} = R^{37}$ = phenoxy; R# = Cl;
(47f) $R^{16} = R^{18} = R^{35} = R^{37}$ = 4-sulfophenoxy; R# = Cl;
(47g) $R^{16} = R^{18} = R^{35} = R^{37}$ = 4-(C(CH$_3$)$_2$—CH$_2$—COOH)-phenoxy; R# = Cl
(47h) $R^{16} = R^{18} = R^{35} = R^{37}$ = 4-(CH$_2$—COOH)-phenoxy; R# = Cl (47i) $R^{16} = R^{37}$ = phenoxy; $R^{18} = R^{35} = R\# = H$;
(47k) $R^{16} = R^{37}$ = 4-sulfophenoxy; $R^{18} = R^{35} = R\# = H$;
(47l) $R^{16} = R^{37}$ = 4-(C(CH$_3$)$_2$—CH$_2$—COOH)-phenoxy; $R^{18} = R^{35} = R\# = H$;
(47m) $R^{16} = R^{37}$ = 4-(CH$_2$—COOH)-phenoxy; $R^{18} = R^{35} = R\# = H$;
(47n) $R^{16} = R^{37}$ = phenoxy; $R^{18} = R^{35} = H$; $R\# = Cl$
(47o) $R^{16} = R^{37}$ = 4-sulfophenoxy; $R^{18} = R^{35}$ H; $R\# = Cl$
(47p) $R^{16} = R^{37}$ = 4-(C(CH$_3$)$_2$—CH$_2$—COOH)-phenoxy; $R^{18} = R^{35} = H$; $R\# = Cl$;
(47q) $R^{16} = R^{37}$ = 4-(CH$_2$—COOH)-phenoxy; $R^{18} = R^{35} = H$; $R\# = Cl$;
(47r) $R^{18} = R^{35}$ = phenoxy; $R^{16} = R^{37}$ $R\# = H$;

(47s) $R^{18} = R^{35}$ = 4-sulfophenoxy; $R^{16} = R^{37} = R\# = H$;
(47t) $R^{18} = R^{35}$ = 4-(C(CH$_3$)$_2$—CH$_2$—COOH)-phenoxy; $R^{16} = R^{37} = R\# = H$;
(47u) $R^{18} = R^{35}$ = 4-(CH$_2$—COOH)-phenoxy; $R^{16} = R^{37} = R\# = H$;
(47v) $R^{18} = R^{35}$ = phenoxy; $R^{16} = R^{37} = H$; $R\# = Cl$
(47w) $R^{18} = R^{35}$ = 4-sulfophenoxy; $R^{16} = R^{37} = H$; $R\# = Cl$
(47x) $R^{18} = R^{35}$ = 4-(—C(CH$_3$)$_2$—CH$_2$—COOH)-phenoxy; $R^{16} = R^{37} = H$; $R\# = Cl$;
(47y) $R^{18} = R^{35}$ = 4-(CH$_2$—COOH)-phenoxy; $R^{16} = R^{37} = H$; $R\# = Cl$;

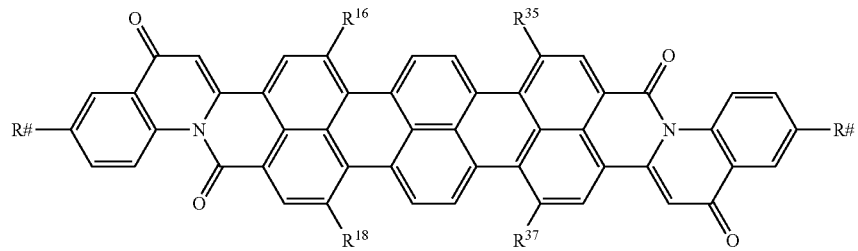

(48a) $R^{16} = R^{18} = R^{37}$ = phenoxy; $R\# = H$;
(48b) $R^{16} = R^{18} = R^{35} = R^{37}$ = 4-sulfophenoxy; $R\# = H$;
(48c) $R^{16} = R^{18} = R^{35} = R^{37}$ = 4-(—C(CH$_3$)$_2$—CH$_2$—COOH)-phenoxy; $R\# = H$
(48d) $R^{16} = R^{18} = R^{35} = R^{37}$ = 4-(—CH$_2$—COOH)-phenoxy; $R\# = H$
(48e) $R^{16} = R^{18} = R^{35} = R^{37}$ = phenoxy; $R\# = Cl$;
(48f) $R^{16} = R^{18} = R^{35} = R^{37}$ = 4-sulfophenoxy; $R\# = Cl$;
(48g) $R^{16} = R^{18} = R^{35} = R^{37}$ = 4-(C(CH$_3$)$_2$—CH$_2$—COOH)-phenoxy; $R\# = Cl$ (48h) $R^{16} = R^{18} = R^{35} = R^{37}$ = 4-(CH$_2$—COOH)-phenoxy; $R\# = Cl$
(48i) $R^{16} = R^{37}$ = phenoxy; $R^{18} = R^{35} = R\# = H$;
(48k) $R^{16} = R^{37}$ = 4-sulfophenoxy; $R^{18} = R^{35} = R\# = H$;
(48l) $R^{16} = R^{37}$ = 4-(C(CH$_3$)$_2$—CH$_2$—COOH)-phenoxy; $R^{18} = R^{35} = R\# = H$;
(48m) $R^{16} = R^{37}$ = 4-(CH$_2$—COOH)-phenoxy; $R^{18} = R^{35} = R\# = H$;
(48n) $R^{16} = R^{37}$ = phenoxy; $R^{18} = R^{35} = H$; $R\# = Cl$
(48o) $R^{16} = R^{37}$ = 4-sulfophenoxy; $R^{18} = R^{35}$ H; $R\# = Cl$
(48p) $R^{16} = R^{37}$ = 4-(C(CH$_3$)$_2$—CH$_2$—COOH)-phenoxy; $R^{18} = R^{35} = H$; $R\# = Cl$;
(48q) $R^{16} = R^{37}$ = 4-(CH$_2$—COOH)-phenoxy; $R^{18} = R^{35} = H$; $R\# = Cl$;

(48r) $R^{18} = R^{35}$ = phenoxy; $R^{16} = R^{37}$ $R\# = H$;
(48s) $R^{18} = R^{35}$ = 4-sulfophenoxy; $R^{16} = R^{37} = R\# = H$;
(48t) $R^{18} = R^{35}$ = 4-(C(CH$_3$)$_2$—CH$_2$—COOH)-phenoxy; $R^{16} = R^{37} = R\# = H$;
(48u) $R^{18} = R^{35}$ = 4-(CH$_2$—COOH)-phenoxy; $R^{16} = R^{37} = R\# = H$;
(48v) $R^{18} = R^{35}$ = phenoxy; $R^{16} = R^{37} = H$; $R\# = Cl$
(48w) $R^{18} = R^{35}$ = 4-sulfophenoxy; $R^{16} = R^{37} = H$; $R\# = Cl$
(48x) $R^{18} = R^{35}$ = 4-(—C(CH$_3$)$_2$—CH$_2$—COOH)-phenoxy; $R^{16} = R^{37} = H$; $R\# = Cl$;
(48y) $R^{18} = R^{35}$ = 4-(CH$_2$—COOH)-phenoxy; $R^{16} = R^{37} = H$; $R\# = Cl$;

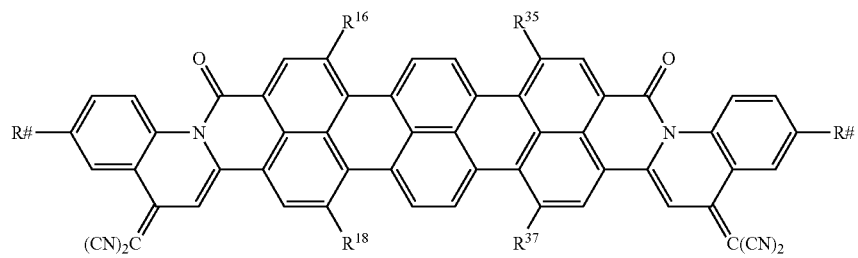

-continued (49a) $R^{16} = R^{18} = R^{37}$ = phenoxy; R# = H;
(49b) $R^{16} = R^{18} = R^{35} = R^{37}$ = 4-sulfophenoxy; R# = H;
(49c) $R^{16} = R^{18} = R^{35} = R^{37}$ = 4-(—C(CH$_3$)$_2$—CH$_2$—COOH)-phenoxy; R# = H
(49d) $R^{16} = R^{18} = R^{35} = R^{37}$ = 4-(CH$_2$—COOH)-phenoxy; R# = H
(49e) $R^{16} = R^{18} = R^{35} = R^{37}$ = phenoxy; R# = Cl;
(49f) $R^{16} = R^{18} = R^{35} = R^{37}$ = 4-sulfophenoxy; R# = Cl;

(49g) $R^{16} = R^{18} = R^{35} = R^{37}$ = 4-(C(CH$_3$)$_2$—CH$_2$—COOH)-phenoxy; R# = Cl
(49h) $R^{16} = R^{18} = R^{35} = R^{37}$ = 4-(CH$_2$—COOH)-phenoxy; R# = Cl
(49i) $R^{16} = R^{37}$ = phenoxy; $R^{18} = R^{35}$ = R# = H;
(49k) $R^{16} = R^{37}$ = 4-sulfophenoxy; $R^{18} = R^{35}$ = R# = H;
(49l) $R^{16} = R^{37}$ = 4-(C(CH$_3$)$_2$—CH$_2$—COOH)-phenoxy; $R^{18} = R^{35}$ = R# = H;
(49m) $R^{16} = R^{37}$ = 4-(CH$_2$—COOH)-phenoxy; $R^{18} = R^{35}$ = R# = H;
(49n) $R^{16} = R^{37}$ = phenoxy; $R^{18} = R^{35}$ = H; R# = Cl (49o) $R^{16} = R^{37}$ = 4-sulfophenoxy; $R^{18} = R^{35}$ H; R# = Cl
(49p) $R^{16} = R^{37}$ = 4-(C(CH$_3$)$_2$—CH$_2$—COOH)-phenoxy; $R^{18} = R^{35}$ = H; R# = Cl;
(49q) $R^{16} = R^{37}$ = 4-(CH$_2$—COOH)-phenoxy; $R^{18} = R^{35}$ = H; R# = Cl;
(49r) $R^{18} = R^{35}$ = phenoxy; $R^{16} = R^{37}$ R# = H;
(49s) $R^{18} = R^{35}$ = 4-sulfophenoxy; $R^{16} = R^{37}$ = R# = H;
(49t) $R^{18} = R^{35}$ = 4-(C(CH$_3$)$_2$—CH$_2$—COOH)-phenoxy; $R^{16} = R^{37}$ = R# = H;
(49u) $R^{18} = R^{35}$ = 4-(CH$_2$—COOH)-phenoxy; $R^{16} = R^{37}$ = R# = H;
(49v) $R^{18} = R^{35}$ = phenoxy; $R^{16} = R^{37}$ = H; R# = Cl
(49w) $R^{18} = R^{35}$ = 4-sulfophenoxy; $R^{16} = R^{37}$ = H; R# = Cl
(49x) $R^{18} = R^{35}$ = 4-(—C(CH$_3$)$_2$—CH$_2$—COOH)-phenoxy; $R^{16} = R^{37}$ = H; R# = Cl;
(49y) $R^{18} = R^{35}$ = 4-(CH$_2$—COOH)-phenoxy; $R^{16} = R^{37}$ = H; R# = Cl;

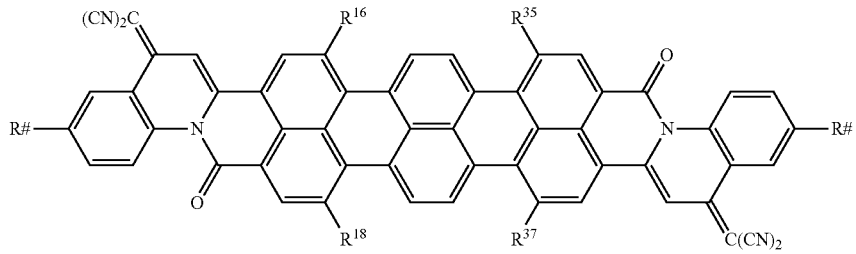

(50a) $R^{16} = R^{18} = R^{37}$ = phenoxy; R# = H;
(50b) $R^{16} = R^{18} = R^{35} = R^{37}$ = 4-sulfophenoxy; R# = H;
(50c) $R^{16} = R^{18} = R^{35} = R^{37}$ = 4-(—C(CH$_3$)$_2$—CH$_2$—COOH)-phenoxy; R# = H
(50d) $R^{16} = R^{18} = R^{35} = R^{37}$ = 4-(CH$_2$—COOH)-phenoxy; R# = H
(50e) $R^{16} = R^{18} = R^{35} = R^{37}$ = phenoxy; R# = Cl;
(50f) $R^{16} = R^{18} = R^{35} = R^{37}$ = 4-sulfophenoxy; R# = Cl;

(50g) $R^{16} = R^{18} = R^{35} = R^{37}$ = 4-(C(CH$_3$)$_2$—CH$_2$—COOH)-phenoxy; R# = Cl
(50h) $R^{16} = R^{18} = R^{35} = R^{37}$ = 4-(CH$_2$—COOH)-phenoxy; R# = Cl
(50i) $R^{16} = R^{37}$ = phenoxy; $R^{18} = R^{35}$ = R# = H;
(50k) $R^{16} = R^{37}$ = 4-sulfophenoxy; $R^{18} = R^{35}$ = R# = H;
(50l) $R^{16} = R^{37}$ = 4-(C(CH$_3$)$_2$—CH$_2$—COOH)-phenoxy; $R^{18} = R^{35}$ = R# = H;
(50m) $R^{16} = R^{37}$ = 4-(CH$_2$—COOH)-phenoxy; $R^{18} = R^{35}$ = R# = H;
(50n) $R^{16} = R^{37}$ = phenoxy; $R^{18} = R^{35}$ = H; R# = Cl (50o) $R^{16} = R^{37}$ = 4-sulfophenoxy; $R^{18} = R^{35}$ H; R# = Cl
(50p) $R^{16} = R^{37}$ = 4-(C(CH$_3$)$_2$—CH$_2$—COOH)-phenoxy; $R^{18} = R^{35}$ = H; R# = Cl;
(50q) $R^{16} = R^{37}$ = 4-(CH$_2$—COOH)-phenoxy; $R^{18} = R^{35}$ = H; R# = Cl;
(50r) $R^{18} = R^{35}$ = phenoxy; $R^{16} = R^{37}$ R# = H;
(50s) $R^{18} = R^{35}$ = 4-sulfophenoxy; $R^{16} = R^{37}$ = R# = H;
(50t) $R^{18} = R^{35}$ = 4-(C(CH$_3$)$_2$—CH$_2$—COOH)-phenoxy; $R^{16} = R^{37}$ = R# = H;

(50u) $R^{18} = R^{35}$ = 4-(CH$_2$—COOH)-phenoxy; $R^{16} = R^{37}$ = R# = H;
(50v) $R^{18} = R^{35}$ = phenoxy; $R^{16} = R^{37}$ = H; R# = Cl
(50w) $R^{18} = R^{35}$ = 4-sulfophenoxy; $R^{16} = R^{37}$ = H; R# = Cl
(50x) $R^{18} = R^{35}$ = 4-(—C(CH$_3$)$_2$—CH$_2$—COOH)-phenoxy; $R^{16} = R^{37}$ = H; R# = Cl;
(50y) $R^{18} = R^{35}$ = 4-(CH$_2$—COOH)-phenoxy; $R^{16} = R^{37}$ = H; R# = Cl;

In a particularly preferred embodiment the compounds of the general formula (I) are selected from compounds of the formulae (I-B) and (I-C).

The enlargement of the conjugated system of the compounds of formulae (I-B) and (I-C) results in a bathochrome shift towards the respective naphthalene diimide and rylene diimide, respectively.

Compounds of formula (I) according to the present invention can be prepared e.g. according to the preparation methods and preparation scheme as described below and in the experimental part of this application.

A further object of the present invention is a process for preparing a compound of the formula (I-A)

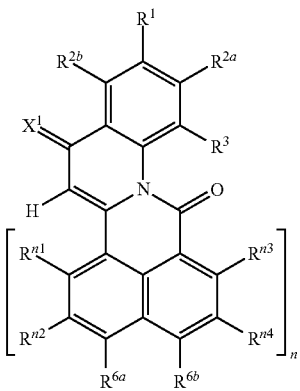

(I-A)

in which n, $X^1$, $R^1$, $R^{2a}$, $R^{2b}$, $R^3$, $R^{n1}$, $R^{n2}$, $R^{n3}$, $R^{n4}$, $R^{6a}$, $R^{6b}$ are as defined above, Compounds of formula (I-A) can be prepared by a process comprising the following steps:

(i) reacting a monoanhydride of the formula (II)

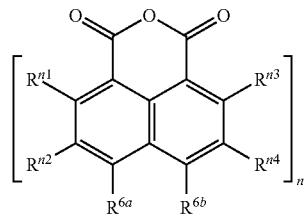

(II)

with a 2-acetyl aniline compound of the formula (III)

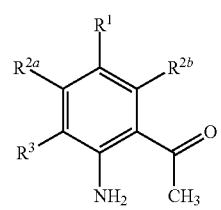

(III)

to obtain a compound of formula (I-Aa)

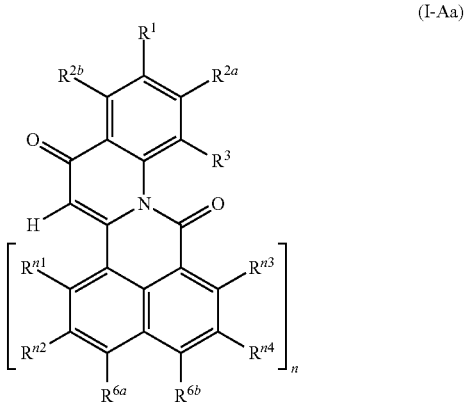

(I-Aa)

and (ii) optionally reacting the compound of the formula (I-Aa) with malononitrile to obtain a compound of formula (I-Ab)

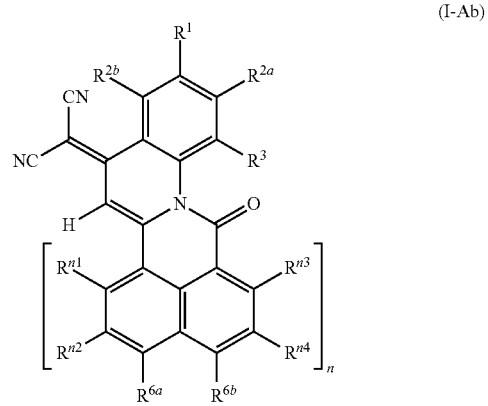

(I-Ab)

Step (i)

Step (i) is a one-pot reaction in which the monoanhydride of the formula (II) is subjected to an imidization with a 2-acetylaniline compound of the formula (III) followed by a subsequent intramolecular aldol condensation to give a compound of formula (I-Aa).

The reaction of the monoanhydride of the formula (II) with the compound of the formula (III) is preferably performed at a temperature in the range of from 100 to 250° C., preferably 140 to 240° C.

The reaction is preferably performed in the presence of catalytic amounts of zinc acetate and a base. Suitable bases are e.g. nitrogen containing heterocycles, which may also serve as solvent for the reaction. A preferred base is quinoline.

Step (ii)

The compound of formula (I-Aa) obtained in step (i) is optionally treated with malononitrile to give the compound of formula (I-Ab). The reaction in step (ii) can be regarded as a Knoevenagel condensation reaction.

In one embodiment, the reaction is performed in the presence of an acid as catalyst. A preferred acid is a mixture of glacial acetic acid and acetic anhydride.

A further process for preparing compounds of the formula (I-A)

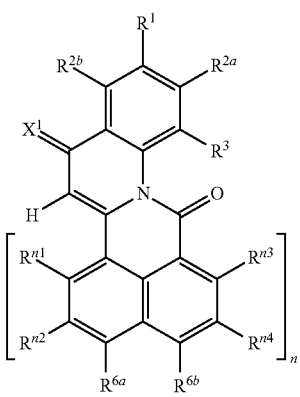
(I-A)

wherein
n, $X^1$, $R^1$, $R^{2a}$, $R^{2b}$, $R^3$, $R^{n1}$, $R^{n2}$, $R^{n3}$, $R^{n4}$, $R^{6a}$ and $R^{6b}$ are as defined above
comprises the following steps:

(iii) reacting a monoanhydride of the formula (II)

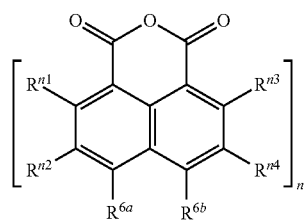
(II)

with a 2-bromoaniline compound of the formula (IV)

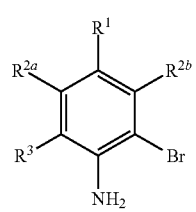
(IV)

to obtain a compound of formula (V)

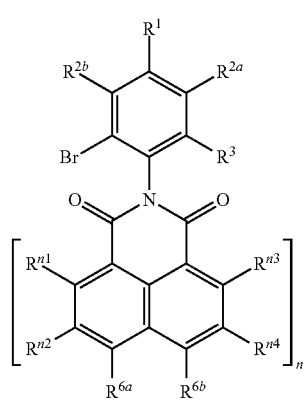
(V)

(iv) reacting the compound of formula (V) with tributyl(1-ethoxy-1-ethenyl)stannane in the presence of a Pd catalyst to obtain a compound of formula (VI)

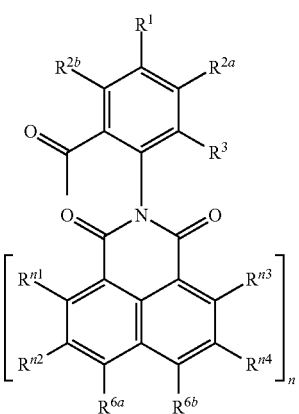
(VI)

(v) subjecting the compound of the formula (VI) to a condensation reaction to obtain a compound of the formula (I-Aa)

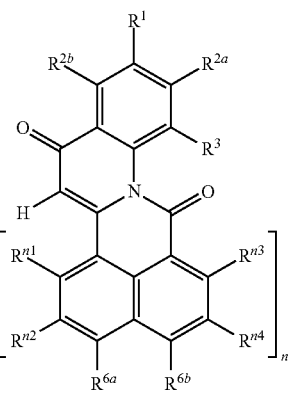
(I-Aa)

(vi) optionally reacting the compound of the formula (I-Aa) with malononitrile to obtain a compound (I-Ab)

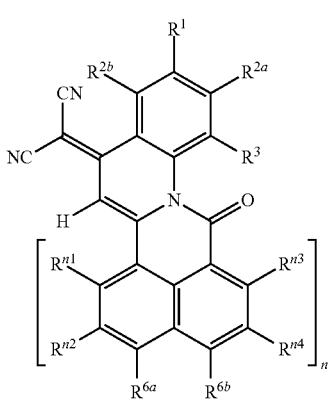
(I-Ab)

Step (iii)

In step (iii), the monoanhydride of the formula (II) is treated with a 2-bromoaniline compound of the formula (IV) to give the imide compound of the formula (V). The reaction temperature is generally in a range of from 100 to 250° C., preferably 1200 to 200° C. The reaction is usually carried out in a solvent. In a preferred embodiment the reaction is performed in quinoline under inert atmosphere such as argon or nitrogen.

Step (iv)

In step (iv) the compound of the formula (V) is reacted with tributyl(1-ethoxy-1-ethenyl)stannane in the presence of a Pd catalyst in a Stille type coupling reaction to give the compound of formula (VI).

Tributyl(1-ethoxy-1-ethenyl)stannane (=tributyl(1-ethoxyvinyl)tin) is commercially available, e.g. from Sigma Aldrich.

The coupling reaction is preferably effected in the presence of a palladium catalyst under reaction conditions known per se for Stille type coupling reactions. Suitable catalysts are especially palladium-catalysts, for example tetrakis(triphenylphosphine)-palladium, $Pd_2(dba)_3$/BINAP, $Pd_2(dba)_3$/Tol-BINAP, $Pd(OAc)_2$, $Pd_2(dba)_3$, $Pd_2(dba)_3$/2-(dicyclohexylphosphino)-biphenyl, $Pd(OAc)_2$/2-(dicyclohexylphosphino)-biphenyl, $Pd(OAc)_2$/2-(di-t-butylphosphino)-2'-methylbiphenyl, $Pd(dba)_2$/DTPE, $Pd(dba)_2$/DPPF, $Pd(OAc)_2$/Xantphos, $Pd(OAc)_2$/n-butylbis(1-adamantyl)-phosphine, $Pd(dba)_2$/n-butylbis(1-adamantyl)-phosphine, $Pd(OAc)_2$/$PPh_3$, $Pd(OAc)_2$/$(4-XC_6H_4)_3P$, $Pd_2(dba)_3$/Xantphos, $Pd(OAc)_2$/2-(Dicyclohexylphosphino)-2'-methylbiphenyl, $Pd(OAc)_2$/DPPP, $PdCl_2(Ph_3P)_2$, $PdCl_2$-[(o-Tol)$_3$]$_2$, $Pd(Ph_3P)_4$, $Pd(OAc)_2$/P(t-Bu)$_3$, $Pd_2(dba)_3$/$CHCl_3$/BINAP, and combinations thereof. The amount of catalyst is typically 1 to 20 mol %, especially 1.5 to 5 mol %, based on the tributyl(1-ethoxy-1-ethenyl)-stannane used.

The process in step (iv) can be carried out in a suitable solvent which is inert under the respective reaction conditions. Solvents which are generally suitable are, for example, aromatics such as toluene and xylenes, hydrocarbons or mixtures of hydrocarbons such as cyclohexane, ethers such as tert-butyl methyl ether, 1,4-dioxane and tetrahydrofuran, dimethylformamide, dimethylsulfoxide, ionic liquids, etc. A particularly preferred solvent is dioxane.

The reaction temperature is generally 20 to 180° C., preferably 50 to 140° C.

The reaction in step (iv) can be carried out in the presence of an inert gas, e.g. nitrogen, argon, etc.

Step (v)

In step (v), the compound of formula (VI) is subjected to an aldol condensation to give the compound of formula (I-Aa). The aldol condensation is preferably performed in the presence of a base. A suitable base is quinoline. The base can also serve as solvent.

The reaction temperature is generally from 50 to 250° C., preferably from 100 to 200° C.

Step (vi)

Step (vi) is optional. The reaction in step (vi) can be regarded as a Knoevenagel condensation reaction of the compound of the formula (I-Aa) with malononitrile to give the compound (I-Ab).

In one embodiment the reaction is performed in the presence of an acid as catalyst. A preferred acid is a mixture of glacial acetic acid and acetic anhydride.

A further object of the invention is a process of preparing compounds of the formulae (I-B) and (I-C)

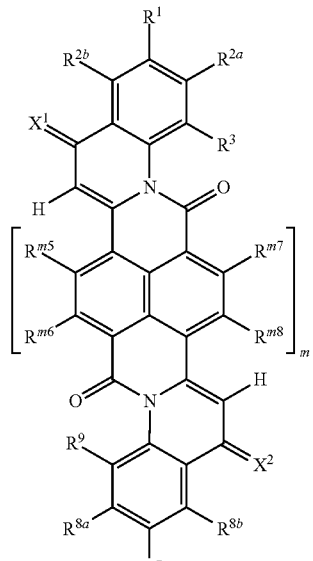

(I-B)

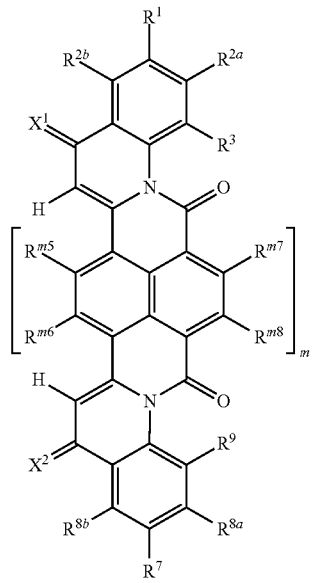

(I-C)

in which m, $X^1$, $X^2$, $R^1$, $R^{2a}$, $R^{2b}$, $R^3$, $R^{m5}$, $R^{m6}$, $R^{m7}$, $R^{m8}$, $R^7$, $R^{8a}$, $R^{8b}$ and $R^9$ are as defined above, and mixtures thereof, comprising (vii) reacting a dianhydride compound of the formula (VII)

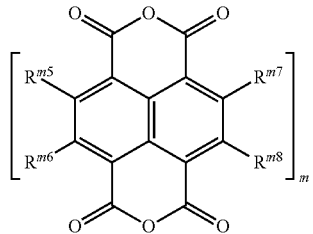

(VII)

with a 2-acetyl aniline compound of the formula (III) and optionally a different 2-acetyl aniline compound of the formula (IIIa)

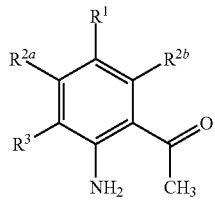
(III)

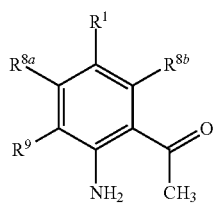
(IIIa)

to give a mixture of compounds of formulae (I-Ba) and (I-Ca)

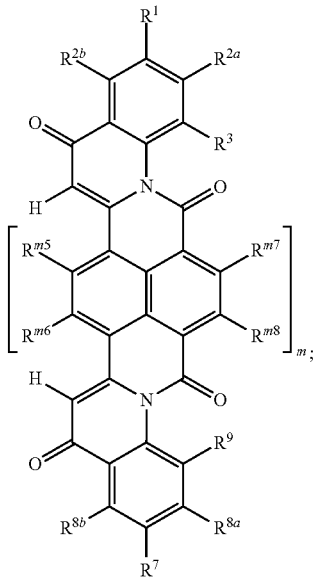
(I-Ca)

(viia) optionally separating the mixtures of compounds of formulae (I-Ba) and (I-Ca);

(viii) optionally reacting the compound(s) obtained in step (vii) or (viia) with malononitrile to obtain the compound of formulae (I-Bb) or (I-Cb)

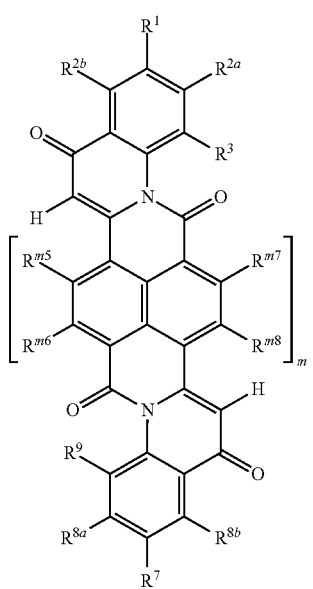
(I-Ba)

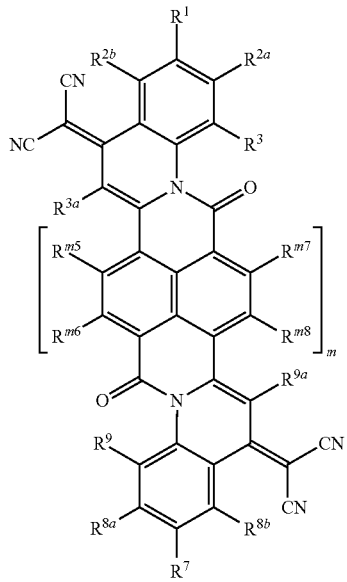
(I-Bb)

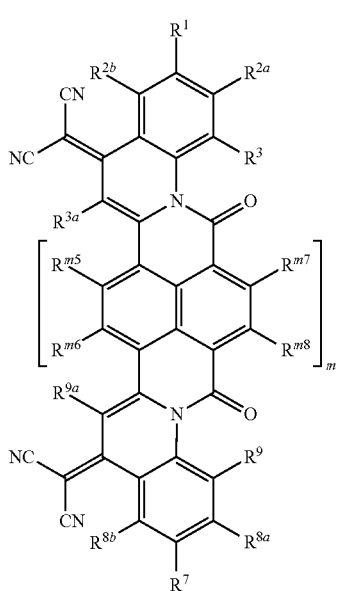

(I-Cb)

or mixtures thereof; and (viiia) optionally separating the mixtures of compounds of formulae (I-Bb) and (I-Cb).

Step (vii)

Step (vii) is a one-pot reaction in which the dianhydride of the formula (VII) is subjected to an imidization with a 2-acetylaniline compound of the formula (III) and optionally a different 2-acetylaniline compound of the formula (IIIb) followed by a subsequent intramolecular aldol condensation to give a mixture of compounds of formulae (I-Ba) and (I-Ca).

The reaction of the dianhydride of the formula (VII) with a compound of the formula (III) and optionally with a compound of the formula (IIIa) is preferably performed at a temperature in the range of from 100 to 250° C., preferably 140 to 240° C.

The reaction is preferably performed in the presence of catalytic amounts of zinc acetate and a base. Suitable bases are e.g. basic nitrogen containing heterocycles, which may also serve as solvent for the reaction. A preferred base is quinoline.

Step (viia)

The mixtures of compounds of formulae (I-Ba) and (I-Ca) can be optionally separated, e.g. by chromatography Step (viii)

The compound(s) obtained in step (vii) or (viia) is(are) optionally treated with malononitrile to give the compound of formulae (I-Bb) and (I-Cb). The reaction in step (viii) can be regarded as a Knoevenagel condensation reaction.

In one embodiment the reaction is performed in the presence of an acid as catalyst. A preferred acid is a mixture of glacial acetic acid and acetic anhydride.

Step (viiia)

The mixtures of compounds of formulae (I-Bb) and (I-Cb) can be optionally separated, e.g. by chromatography.

Compounds of the formula (I), where A is a radical of the formulae (A.1), (A.2), or (A.4) can be prepared in analogy to the processes described above for the preparation of compounds of formula (I-A).

Compounds of the formula (I), where A is a radical of the formula (A.5) can be prepared in analogy to the processes described above for the preparation of compounds of formulae (I-B) and (I-C).

As a rule, the compounds of formula (I) including their isomers, and their precursors in the synthesis process, can be prepared by the methods described above. If individual compounds can not be prepared via the above-described routes, they can be prepared by derivatization of other compounds (I) or the respective precursor or by customary modifications of the synthesis routes described.

Monoanhydrides of formula (II) are commercially available or can be synthesized by processes known in the art. 2-acetyl aniline compounds of formula (III) and (IIIa) are commercially available or can be synthesized by processes known in the art.

Phthalic anhydrides are commercially available or can be synthesized by processes known in the art.

2,3-Naphthalic anhydrides, anthracene anhydrides are also commercially available or can be synthesized by processes known in the art.

The compounds of formula (I) are valuable far-red emitters. The compounds of formula (I) have metal binding capability.

The compounds of formula (I), especially the compounds of the formulae (I-A), (I-Aa), (I-Ab), (I-B), (I-Ba), (I-Bb), (I-C), (I-Ca) and (I-Cb), are suitable for use
  as fluorescent colorant, in particular as fluorescent colorant in a display based on fluorescence conversion,
  for data storage,
  as a UV absorber,
  for optical labels,
  as a fluorescent label for biomolecules,
  in the laser welding of polymer materials,
  in inks, preferably in ink jet inks and printing inks,
  in surface coatings, preferably as or in the colored layer of a coating composition, in particular in a coating composition for the automotive industry, and
  for coloring polymer compositions.

A further object of the invention is a composition comprising at least one compound of the formula (I) as defined above and at least polymer, preferably at least one thermoplastic polymer. With regard to suitable and preferred compounds of the formula (I) reference is made to the suitable and preferred compounds of the formula (I) as mentioned before.

It has been surprising found that the compounds of the general formula (I) have advantageous properties as colorants for use in polymer compositions.

Advantageously, the compounds of the general formula (I) are compatible with a wide range of different polymers. In particular, they are characterized by a good solubility in different classes of polymers. They have excellent processing behaviour, fastness properties, good light fastness and thermal stability. Further, the compounds of the general formula (I) are capable of forming transparent colored polymer compositions.

In a special embodiment, the compounds of the general formula (I) are used in a polymer composition comprising at least on thermoplastic polymer.

Preferably, the thermoplastic polymer is selected from
  homo- and copolymers which comprise at least one copolymerized monomer selected from $C_2$-$C_{10}$-monoolefins, 1,3-butadiene, 2-chloro-1,3-butadiene, vinyl alcohol and its $C_2$-$C_{10}$-alkyl esters, vinyl chloride, vinylidene chloride, vinylidene fluoride, tetrafluoroethylene, glycidyl acrylate, glycidyl methacrylate, acrylates and methacrylates of $C_1$-$C_{10}$-alcohols, vinylaromatics, (meth)acrylonitrile, maleic anhydride, and α,β-ethylenically unsaturated mono- and dicarboxylic acids, homo- and copolymers of vinyl acetals,
polyvinyl esters,
polycarbonates,
polyesters,
polyethers,
polyether ketones,
thermoplastic polyurethanes,
polysulfides,
polysulfones,
polyether sulfones,
cellulose alkyl esters,
and mixtures thereof.

Mention may be made by way of example of polyacrylates having identical or different alcohol moieties from the group of the $C_4$-$C_8$-alcohols, particularly of butanol, hexanol, octanol, and 2-ethylhexanol, polymethyl methacrylate (PMMA), methyl methacrylate-butyl acrylate copolymers, acrylonitrile-butadiene-styrene copolymers (ABSs), ethylene-propylene copolymers, ethylene-propylene-diene copolymers (EPDMs), polystyrene (PS), styrene-acrylonitrile copolymers (SANs), acrylonitrile-styrene-acrylate (ASA), styrene-butadiene-methyl methacrylate copolymers (SBMMAs), styrene-maleic anhydride copolymers, styrene-methacrylic acid copolymers (SMAs), polyoxymethylene (POM), polyvinyl alcohol (PVAL), polyvinyl acetate (PVA), polyvinyl butyral (PVB), polycaprolactone (PCL), polyhydroxybutyric acid (PHB), polyhydroxyvaleric acid (PHV), polylactic acid (PLA), ethylcellulose (EC), cellulose acetate (CA), cellulose propionate (CP), and cellulose acetate/butyrate (CAB).

The thermoplastic polymer useful for coloration according to this invention are especially polyester, polycarbonate (PC), polystyrene (PS), polymethyl methacrylate (PMMA), polyvinylchloride, polyamide, polyethylene, polypropylene, styrene/acrylonitrile (SAN) or acrylonitrile/butadiene/styrene (ABS). Particular preference is given to polyester, polycarbonate, polystyrene, polyvinylchloride and PMMA.

The compound of the formula (I) is especially used in a molding composition comprising at least one elastomer and at least one compound of the general formula (I). The elastomer comprised in the molding compositions of the invention is preferably at least one natural rubber (NR), at least one rubber produced by a synthetic route, or a mixture thereof. Examples of preferred rubbers produced by a synthetic route are polyisoprene rubber (IR), styrene-butadiene rubber (SBR), butadiene rubber (BR), nitrile-butadiene rubber (NBR), and chloroprene rubber (CR).

For the purposes of the invention, the polymer composition can comprise at least one further additive in addition to the above constituents. Suitable additives are plastizisers, stabilizers, lubricants, fillers, pigments, flame retardants, light stabilizers, blowing agents, polymeric processing aids, impact modifiers, optical brighteners, antistatic agents, biostabilizers, etc.

The polymer composition of the invention can be used in a wide variety of products. These are e.g. packaging for food or drink, products for the interior sector, toys and child-care items, sports and leisure products, apparel, fibers for textiles, medical products, hygiene products, and the like.

The packaging that can be produced from the polymer composition of the invention for food or drink are for example freshness-retention foils, food-or-drink hoses, drinking-water hoses, containers for storing or freezing food or drink, lid gaskets, closure caps, crown corks, or synthetic corks for wine.

The products which can be produced from the polymer composition of the invention for the interior sector are for example floorcoverings, which can have homogeneous structure or a structure composed of a plurality of layers, composed of at least one foamed layer, examples being sports floors and other floorcoverings, luxury vinyl tiles (LVT), synthetic leather, wallcoverings, or foamed or unfoamed wallpapers in buildings, or are cladding or console covers in vehicles.

The toys and child-care items which can be produced from the polymer composition of the invention are for example dolls, inflatable toys, such as balls, toy figures, modeling clays, swimming aids, stroller covers, baby-changing mats, bedwarmers, teething rings, or bottles.

The sports and leisure products that can be produced from the polymer composition of the invention are for example gymnastics balls, exercise mats, seat cushions, massage balls and massage rolls, shoes and shoe soles, balls, air mattresses, and drinking bottles.

The medical products which can be produced from the polymer composition of the invention are for example tubes for enteral nutrition and hemodialysis, breathing tubes, infusion tubes, infusion bags, blood bags, catheters, tracheal tubes, gloves, breathing masks, or disposal syringes.

In a further special embodiment, the compounds of the general formula (I) are employed in surface coatings. They are in particular suitable as or in the colored layer of a coating composition. The compounds of the general formula (I) are suitable for producing multicoat color systems that are used e.g. in the automotive industry for the finishing of automobiles.

A typical coating composition comprises one or more of the following components:
(A) at least one primer,
(B) at least one color and/or effect basecoat, and
(C) at least one clear coat.

The compounds of the general formula (I) can be used advantageously in the color coat or effect basecoat of the coating composition.

Coating compositions can be coated on the article by any of a number of techniques well-known in the art. These include, for example, spray coating, dip coating, roll coating, curtain coating, and the like. For automotive body panels, spray coating is preferred.

Colored coating compositions for the formation of a single layer on a substrate or for the formation of a composite coating are well-known in the art, and do not require explanation in detail herein. Polymers known in the art to be useful in coating compositions include acrylics, vinyls, polyurethanes, polycarbonates, polyesters, alkyds, polysiloxanes, etc. Preferred polymers include acrylics and polyurethanes. In one embodiment, the coating composition may also utilize a carbamate-functional acrylic polymer. Polymers for use in coating compositions are preferably cross-linkable, and thus comprise one or more type of cross-linkable functional groups. Such groups include, for example, hydroxy, isocyanate, amine, epoxy, acrylate, vinyl, silane, and acetoacetate groups. These groups may be masked or blocked in such a way so that they are unblocked and available for the cross-linking reaction under the desired curing conditions, generally elevated temperatures and/or actinic radiation.

The substrates to be coated may be made of any of a wide variety of materials. Examples of suitable materials are wood, glass, leather, plastics, metals, especially reactive utility metals, such as iron, steel, stainless steel, zinc, aluminum, titanium and their alloys with one another and with other metals; minerals, especially fired and unfired clay, ceramic, natural stone and artificial stone; foams; fiber materials, especially glass fibers, ceramic fibers, carbon fibers, textile fibers, polymer fibers or metal fibers, and composite fibers; or fiber reinforced materials, especially plastics reinforced with the abovementioned fibers.

The compounds of the general formula (I) can be used with preference for coating motor vehicle bodies, especially commercial and passenger vehicle bodies, and also parts, especially mounted components, thereof, the inside and outside of buildings and parts thereof, doors, windows, furniture, and hollow glassware, and, in the context of industrial coatings, for coating coils, containers, packaging, small parts, such as nuts, bolts, wheel rims or hubcaps, electrical components, such as wound products (coils, stators, rotors); and components for white goods, such as radiators, domestic appliances, refrigerator casings or washing machine casings.

The compounds of the general formula (I) can be used with preference for preparing inks, for printing inks in printing processes, for flexographic printing, screen printing, packaging printing, security color printing, intaglio printing or offset printing, for print precursors and also for textile printing, for office applications, home applications or graphic applications such as, for example, for paper goods, for ballpoint pens, felt-tippens, fibre-tip pens, paperboard, wood, (wood)stains, metal, stamp pads or inks for impact printing processes (involving impact printing colour ribbons), for preparing colorants, for textile decoration and for industrial marking, for roll coatings or powder coatings or for automotive coatings, for high solids (low solvent), aqueous or metallic coatings or for pigmented formulations or aqueous paints, for mineral oils, greases or waxes, for preparing coloured plastics for coatings, fibres, platters or mould carriers, for preparing non-impact printing material for digital printing, for the thermal wax transfer printing process, the ink jet printing process or for the thermal transfer printing process, or for preparing polymeric colour particles, toners, dry copy toners, liquid copy toners or electrophotographic toners.

The compounds of the formula (I) are suitable as organic semiconductors. They generally can function as n-type semiconductors or p-type semiconductors. In electronic devices that employ a combination of two different semiconductors, e.g. organic solar cells, it depends on the position of the energy levels (ionization potential IP and electron affinity EA) in the corresponding semiconductor material if a compound of the formula (I) acts as n-type semiconductor or as p-type semiconductor. Further, if a compound of the formula (I) acts as n-type semiconductor or as p-type semiconductors depends inter alia on the employed gate dielectric. The compounds of the formula (I) are also suitable as ambipolar semiconductors (i.e. a material which has both, hole transport properties and electron transport properties).

The compounds of the formula (I) have at least one of the following advantages over known organic semiconductor materials:
  high charge transport mobility,
  air stability,
  high on/off ratio,
  suitability to be employed in a solvent-based process.

The compounds of the formula (I) are suitable for organic field-effect transistors. They may be used, for example, for the production of integrated circuits (ICs), for which customary n-channel MOSFETs (metal oxide semiconductor field-effect transistors) have been used to date. These are then CMOS-like semiconductor units, for example for microprocessors, microcontrollers, static RAM and other digital logic circuits. For the production of semiconductor materials, the compounds of the formula (I) can be processed further by one of the following processes: printing (offset, flexographic, gravure, screenprinting, inkjet, electrophotography), evaporation, laser transfer, photolithography, drop-casting. They are especially suitable for use in displays (specifically large-surface area and/or flexible displays), RFID tags, smart labels and sensors.

The compounds of the formula (I) are suitable as electron conductors in organic field-effect transistors, organic solar cells and in organic light-emitting diodes. They are also particularly advantageous as an exciton transport material in excitonic solar cells.

Some of the compounds of the formula (I) are fluorescent. Thus, these compounds are also particularly advantageously suitable as fluorescent colorants, in particular as fluorescent colorants in a display based on fluorescence conversion. Such displays comprise generally a transparent substrate, a fluorescent colorant present on the substrate and a radiation source. Typical radiation sources emit blue (color by blue) or UV light (color by UV). The colorants absorb either the blue or the UV light and are used as green emitters. In these displays, for example, the red light is generated by exciting the red emitter by means of a green emitter which absorbs blue or UV light. Suitable color-by-blue displays are described, for example, in WO 98/28946. Suitable color-by-UV displays are described, for example, by W. A. Crossland, I. D. Sprigle and A. B. Davey in Photoluminescent LCDs (PL-LCD) using phosphors, Cambridge University and Screen Technology Ltd., Cambridge, UK. The compounds of the formula (I) are also particularly suitable in displays which, based on an electrophoretic effect, switch colors on and off via charged pigment colorants. Such electrophoretic displays are described, for example, in US 2004/0130776.

The invention further provides organic field-effect transistors comprising a substrate with at least one gate structure, a source electrode and a drain electrode, and at least one compound of the formula (I) as defined above as a semiconductor.

The invention further provides substrates having a plurality of organic field-effect transistors, wherein at least some of the field-effect transistors comprise at least one compound of the formula (I) as defined above.

The invention also provides semiconductor units which comprise at least one such substrate.

A specific embodiment is a substrate with a pattern (topography) of organic field-effect transistors, each transistor comprising
  an organic semiconductor disposed on the substrate;
  a gate structure for controlling the conductivity of the conductive channel; and
  conductive source and drain electrodes at the two ends of the channel,
the organic semiconductor consisting of at least one compound of the formula (I) or comprising a compound of the formula (I). In addition, the organic field-effect transistor generally comprises a dielectric.

A specific embodiment is a substrate with a pattern (topography) of organic field-effect transistors, each transistor comprising
  an organic semiconductor disposed on a buffer layer on a substrate;
  a gate structure for controlling the conductivity of the conductive channel; and
  conductive source and drain electrodes at the two ends of the channel, the organic semiconductor consisting of at least one compound of the formula (I) or comprising a compound of the formula (I). In addition, the organic field-effect transistor generally comprises a dielectric.

As a buffer layer, any dielectric material is suitable, for example anorganic materials such LIF, $AlO_x$, $SiO_2$ or silicium nitride or organic materials such as polyimides or polyacrylates, e.g. polymethylmethacrylate (PMMA).

A further specific embodiment is a substrate having a pattern of organic field-effect transistors, each transistor forming an integrated circuit or being part of an integrated circuit and at least some of the transistors comprising at least one compound of the formula (I).

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, ceramics, $SiO_2$, especially quartz), semiconductors (e.g. doped Si, doped Ge), metal alloys (for example based on Au, Ag, Cu, etc.), semiconductor alloys, polymers (e.g. polyvinyl chloride, polyolefins, such as polyethylene and polypropylene, polyesters, fluoropolymers, polyamides, polyimides, polyurethanes, polyethersulfones, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop), cyanopullulans (e.g. CYMM), polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_3SiOSiCl_3$, $Cl_3Si—(CH_2)_6—SiCl_3$, $Cl_3Si—(CH_2)_{12}—SiCl_3$, and/or which are crosslinked by atmospheric moisture or by addition of water diluted with solvents (see, for example, Facchetti, Adv. Mater. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facchetti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators, such as $SiO_2$, silicon nitride ($Si_3N_4$), etc., ferroelectric insulators, such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 6, 7, 8, 9, 10 or 11 of the Periodic Table, such as Pd, Au, Ag, Cu, Al, Ni, Cr, etc. Also suitable are conductive polymers, such as PEDOT (=poly (3,4-ethylenedioxythiophene)):PSS (=poly(styrenesulfonate)), polyaniline, surface-modified gold, etc. Preferred electrically conductive materials have a specific resistance of less than $10^{-3}$ ohm x meter, preferably less than $10^{-4}$ ohm x meter, especially less than $10^{-6}$ or $10^{-7}$ ohm x meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation or sputtering, lithographic processes or another structuring process, such as printing techniques.

The semiconductor materials may also be processed with suitable auxiliaries (polymers, surfactants) in disperse phase by printing.

In a first preferred embodiment, the deposition of at least one compound of the general formula (I) (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula (I) are suitable particularly advantageously for use in a PVD process, since they essentially do not decompose and/or form undesired byproducts. The material deposited is obtained in high purity. In a specific embodiment, the deposited material is obtained in the form of crystals or comprises a high crystalline content. In general, for the PVD, at least one compound of the general formula (I) is heated to a temperature above its evaporation temperature and deposited on a substrate by cooling below the crystallization temperature. The temperature of the substrate in the deposition is preferably within a range from about 20 to 250° C., more preferably from 50 to 200° C. It has been found that, surprisingly, elevated substrate temperatures in the deposition of the compounds of the formula (I) can have advantageous effects on the properties of the semiconductor elements achieved.

The resulting semiconductor layers generally have a thickness which is sufficient for forming a semiconductor channel which is in contact with the source/drain electrodes. The deposition can be effected under an inert atmosphere, for example, under nitrogen, argon or helium.

The deposition is effected typically at ambient pressure or under reduced pressure. A suitable pressure range is from about $10^{-7}$ to 1.5 bar.

The compound of the formula (I) is preferably deposited on the substrate in a thickness of from 10 to 1000 nm, more preferably from 15 to 250 nm. In a specific embodiment, the compound of the formula (I) is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

In a second preferred embodiment, the deposition of at least one compound of the general formula (I) (and if appropriate further semiconductor materials) is effected by spin-coating. Surprisingly, it is thus also possible to use the compounds of the formula (I) used in accordance with the invention in a wet processing method to produce semiconductor substrates. The compounds of the formula (I) should thus also be suitable for producing semiconductor elements, especially OFETs or based on OFETs, by a printing process. It is possible for this purpose to use customary printing or coating processes (inkjet, flexographic, offset, gravure; intaglio printing, nanoprinting, slot die). Preferred solvents for the use of compounds of the formula (I) in a printing process are aromatic solvents, such as toluene, xylene, etc. It is also possible to add thickening substances, such as polymers, for example polystyrene, etc., to these "semiconductor inks". In this case, the dielectrics used are the aforementioned compounds.

In a preferred embodiment, the inventive field-effect transistor is a thin-film transistor (TFT). In a customary construction, a thin-film transistor has a gate electrode disposed on the substrate or buffer layer (the buffer layer being part of the substrate), a gate insulation layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula (I) (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compounds of the formula (I). In a suitable embodiment, a portion of the surface or the complete surface of the substrate is coated with at least one compound (C1) in order to enable improved deposition of at least one compound of the general formula (I) (and if appropriate further semiconductive compounds). A further embodiment comprises the deposition of a pattern of compounds of the general formula (C1) on the substrate by a corresponding production process. These include the mask processes known for this purpose and so-called "patterning" processes, as described, for example, in U.S. Ser. No. 11/353,934, which is incorporated here fully by reference.

Suitable compounds of the formula (C1) are capable of a binding interaction both with the substrate and with at least one semiconductor compound of the general formula (I). The term "binding interaction" comprises the formation of a chemical bond (covalent bond), ionic bond, coordinative interaction, van der Waals interactions, e.g. dipole-dipole interactions etc.), and combinations thereof. Suitable compounds of the general formula (C1) are:

silane, phosphonic acids, carboxylic acids, hydroxamic acids, such as alkyltrichlorosilanes, e.g. n-octadecyltrichlorosilane; compounds with trialkoxysilane groups, e.g. alkyltrialkoxysilanes such as n-octadecyltrimethoxysilane, n-octadecyltriethoxysilane, n-octadecyltri(n-propyl)oxysilane, n-octadecyltri(isopropyl)oxysilane; trialkoxyaminoalkylsilanes, such as triethoxyaminopropylsilane and N[(3-triethoxysilyl)propyl]ethylenediamine; trialkoxyalkyl 3-glycidyl ether silanes, such as triethoxypropyl 3-glycidyl ether silane; trialkoxyallylsilanes, such as allyltrimethoxysilane; trialkoxy(isocyanatoalkyl)silanes; trialkoxysilyl(meth)acryloyloxyalkanes and trialkoxysilyl(meth)acrylamidoalkanes, such as 1-triethoxysilyl-3-acryloyl-oxypropane.

amines, phosphines and sulfur-comprising compounds, especially thiols.

The compound (C1) is preferably selected from alkyltrialkoxysilanes, especially n-octadecyltrimethoxysi lane, n-octadecyltriethoxysilane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

Preferred semiconductor architectures are the following:
1. substrate, dielectric, organic semiconductor, preferably gate, dielectric, organic semiconductor, source and drain, known as "Bottom Gate Top Contact";
2. substrate, dielectric, organic semiconductor, preferably substrate, gate, dielectric, source and drain, organic semiconductor, known as "Bottom Gate Bottom Contact";
3. substrate, organic semiconductor, dielectric, preferably substrate, source and drain, organic semiconductor, dielectric, gate, known as "Top Gate Bottom Contact";
4. substrate, organic semiconductor, dielectric, preferably substrate, organic semiconductor, source and drain, dielectric, gate, known as "Top Gate Top Contact";

The layer thicknesses are, for example, from 10 nm to 5 µm in semiconductors, from 50 nm to 10 µm in the dielectric; the electrodes may, for example, be from 20 nm to 10 µm. The OFETs may also be combined to form other components, such as ring oscillators or inverters.

A further aspect of the invention is the provision of electronic components which comprise a plurality of semiconductor components, which may be n-type and/or p-type semiconductors. Examples of such components are field-effect transistors (FETs), bipolar junction transistors (BJTs), tunnel diodes, converters, light-emitting components, biological and chemical detectors or sensors, temperature-dependent detectors, photodetectors, such as polarization-sensitive photodetectors, gates, AND, NAND, NOT, OR, TOR and NOR gates, registers, switches, timer units, static or dynamic stores and other dynamic or sequential, logical or other digital components including programmable switches.

A specific semiconductor element is an inverter. In digital logic, the inverter is a gate which inverts an input signal. The inverter is also referred to as a NOT gate. Real inverter switches have an output current which constitutes the opposite of the input current. Typical values are, for example, (0, +5V) for TTL switches. The performance of a digital inverter reproduces the voltage transfer curve (VTC), i.e. the plot of input current against output current. Ideally, it is a staged function and, the closer the real measured curve approximates to such a stage, the better the inverter is. In a specific embodiment of the invention, the compounds of the formula (I) are used as organic semiconductors in an inverter.

The compounds of the formula (I) are also particularly advantageously suitable for use in organic photovoltaics (OPVs). Preference is given to their use in solar cells which are characterized by diffusion of excited states (exciton diffusion). In this case, one or both of the semiconductor materials utilized is notable for a diffusion of excited states (exciton mobility). Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flow to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. Solar cells consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of the general formula (I) described above are particularly advantageously suitable for use in excitonic solar cells.

Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

The invention provides an organic solar cell which comprises a substrate with at least one cathode and at least one anode, and at least one compound of the general formula (I) as defined above as a photoactive material. The inventive organic solar cell comprises at least one photoactive region. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction. Organic solar cells with photoactive donor-acceptor transitions in the form of a bulk heterojunction are a preferred embodiment of the invention.

Suitable substrates for organic solar cells are, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth)acrylates, polystyrenes, polyvinyl chlorides and mixtures and composites.

Suitable electrodes (cathode, anode) are in principle metals, semiconductors, metal alloys, semiconductor alloys, nanowire thereof and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), poly(3,4-ethylenedioxythiophene) poly(styrenesulfonate) (PEDOT-PSS), etc. Preferred metal alloys are, for example, alloys based on Pt, Au, Ag, Cu, etc. A specific embodiment is Mg/Ag alloys.

The material used for the electrode facing the light (the anode in a normal structure, the cathode in an inverse structure) is preferably a material at least partly transparent to the incident light. This preferably includes electrodes which have glass and/or a transparent polymer as a carrier material. Transparent polymers suitable as carriers are those mentioned above, such as polyethylene terephthalate. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt. Particular preference is given to ITO for contact connection. For electrical contact connection, it is also possible to use a conductive polymer, for example a poly-3,4-alkylenedioxy-thiophene, e.g. poly-3,4-ethyleneoxythiophene poly(styrenesulfonate) (PEDOT).

The electrode facing the light is configured such that it is sufficiently thin to bring about only minimal light absorption but thick enough to enable good charge transport of the extracted charge carriers. The thickness of the electrode layer (without carrier material) is preferably within a range from 20 to 200 nm.

In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof. Preferred mixtures are Mg/Al. The thickness of the electrode layer is preferably within a range from 20 to 300 nm.

The photoactive region comprises or consists of at least one layer which comprises at least one compound of the general formula (I) as defined above. In addition, the photoactive region may have one or more further layer(s). These are, for example, selected from layers with electron-conducting properties (electron transport layer, ETL),
layers which comprise a hole-conducting material (hole transport layer, HTL), which need not absorb any radiation,
exciton- and hole-blocking layers (e.g. EBLs), which must not absorb, and
multiplication layers.

Suitable materials for these layers are described in detail hereinafter. Suitable exciton- and hole-blocking layers are described, for example, in U.S. Pat. No. 6,451,415. Suitable materials for exciton-blocking layers are, for example, bathocuproin (BCP), 4,4',4"-tris[3-methylphenyl-N-phenylamino]triphenylamine (m-MTDATA).

The inventive solar cells comprise at least one photoactive donor-acceptor heterojunction. Optical excitation of an organic material generates excitons. In order that a photocurrent occurs, the electron-hole pair has to be separated, typically at a donor-acceptor interface between two unlike contact materials. At such an interface, the donor material forms a heterojunction with an acceptor material. When the charges are not separated, they can recombine in a process also known as "quenching", either radiatively by the emission of light of a lower energy than the incident light or nonradiatively by generation of heat. Both processes are undesired. According to the invention, at least one compound of the general formula (I) can be used as a charge generator (donor) or as electron acceptor material.

If at least one compound of the general formula (I) is used as a charge generator (donor) it can be combined with an appropriate electron acceptor material (ETM, electron transport material). Radiative excitation is followed by a rapid electron transfer to the ETM. Suitable ETMs are, for example, C60 and other fullerenes, perylene-3,4;9,10-bis (dicarboximides) (PTCDIs), or n-doped layers thereof (as described hereinafter). Preferred ETMs are C60 and other fullerenes or n-doped layers thereof.

In a first embodiment, the heterojunction has a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).).

In a second preferred embodiment, the heterojunction is configured as a bulk (mixed) heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005). Bulk heterojunctions are discussed in detail hereinafter.

The compounds of the formula (I) can be used as a photoactive material in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The compounds of the formula (I) can also be used as a photoactive material in tandem cells. Suitable tandem cells are described, for example, by P. Peumans, A. Yakimov, S. R. Forrest in J. Appl. Phys., 93 (7), 3693-3723 (2003) (see also U.S. Pat. Nos. 4,461,922, 6,198,091 and 6,198,092) and are described in detail hereinafter. The use of compounds of the general formula (I) in tandem cells is a preferred embodiment of the invention.

The compounds of the formula (I) can also be used as a photoactive material in tandem cells which are constructed from two or more than two stacked MiM, pin, Mip or Min structures (see DE 103 13 232.5 and J. Drechsel et al., Thin Solid Films, 451452, 515-517 (2004)).

The layer thickness of the M, n, i and p layers is typically within a range from 10 to 1000 nm, more preferably from 10 to 400 nm. The layers which form the solar cell can be produced by customary processes known to those skilled in the art. These include vapor deposition under reduced pressure or in an inert gas atmosphere, laser ablation or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

In order to improve the efficiency of organic solar cells, it is possible to shorten the mean distance through which the exciton has to diffuse in order to arrive at the next donor-acceptor interface. To this end, it is possible to use mixed layers of donor material and acceptor material which form an interpenetrating network in which internal donor-acceptor heterojunctions are possible. This bulk heterojunction is a specific form of the mixed layer, in which the excitons generated need only travel a very short distance before they arrive at a domain boundary, where they are separated.

In a preferred embodiment, the photoactive donor-acceptor transitions in the form of a bulk heterojunction are produced by a gas phase deposition process (physical vapor deposition, PVD). Suitable processes are described, for example, in US 2005/0227406, to which reference is made here. To this end, a compound of the general formula (I) and a complementary semiconductor material can be subjected to a gas phase deposition in the manner of a cosublimation. PVD processes are performed under high-vacuum conditions and comprise the following steps: evaporation, transport, deposition. The deposition is effected preferably at a pressure within a range from about $10^{-2}$ mbar to $10^{-7}$ mbar, for example from $10^{-5}$ to $10^{-7}$ mbar. The deposition rate is preferably within a range from 0.01 to 100 nm/s. The deposition can be effected in an inert gas atmosphere, for example under nitrogen, helium or argon. The temperature of the substrate during the deposition is preferably within a range from −100 to 300° C., more preferably from −50 to 250° C.

The other layers of the organic solar cell can be produced by known processes. These include vapor deposition under reduced pressure or in an inert gas atmosphere, laser ablation, or solution or dispersion processing methods such as spincoating, knifecoating, casting methods, spray application, dipcoating or printing (e.g. inkjet, flexographic, offset, gravure; intaglio, nanoimprinting). In a specific embodiment, the entire solar cell is produced by a gas phase deposition process.

The photoactive layer (homogeneous layer or mixed layer) can be subjected to a thermal treatment directly after production thereof or after production of further layers which form the solar cell. Such a heat treatment can in many cases further improve the morphology of the photoactive layer. The temperature is preferably within a range from about 60° C. to 300° C. The treatment time is preferably within a range from 1 minute to 3 hours. In addition or alternatively to a thermal treatment, the photoactive layer (mixed layer) can be subjected to a treatment with a solvent-containing gas directly after production thereof or after production of further layers which form the solar cell. In a suitable embodiment, saturated solvent vapors in air are used at ambient temperature. Suitable solvents are toluene, xylene, chloroform, N-methylpyrrolidone, dimethylformamide, ethyl acetate, chlorobenzene, dichloromethane and mixtures thereof. The treatment time is preferably within a range from 1 minute to 3 hours.

In a suitable embodiment, the inventive solar cells are present as an individual cell with flat heterojunction and normal structure. In a specific embodiment, the cell has the following structure:

an at least partly transparent conductive layer (top electrode, anode) (11)
a hole-conducting layer (hole transport layer, HTL) (12)
a layer which comprises a donor material (13)
a layer which comprises an acceptor material (14)
an exciton-blocking and/or electron-conducting layer (15)
a second conductive layer (back electrode, cathode) (16)

The donor material preferably comprises at least one compound of the formula (I) or consists of a compound of the formula (I). The acceptor material preferably comprises at least one fullerene or fullerene derivative, or consists of a fullerene or fullerene derivative. The acceptor material preferably comprises C60 or PCBM ([6,6]-phenyl-C61-butyric acid methyl ester).

The essentially transparent conductive layer (11) (anode) comprises a carrier, such as glass or a polymer (e.g. polyethylene terephthalate) and a conductive material, as described above. Examples include ITO, doped ITO, FTO, ZnO, AZO, etc. The anode material can be subjected to a surface treatment, for example with UV light, ozone, oxygen plasma, $Br_2$, etc. The layer (11) should be sufficiently thin to enable maximum light absorption, but also sufficiently thick to ensure good charge transport. The layer thickness of the transparent conductive layer (11) is preferably within a range from 20 to 200 nm.

Solar cells with normal structure optionally have a hole-conducting layer (HTL). This layer comprises at least one hole-conducting material (hole transport material, HTM). Layer (12) may be an individual layer of essentially homogeneous composition or may comprise two or more than two sublayers.

Hole-conducting materials (HTM) suitable for forming layers with hole-conducting properties (HTL) preferably comprise at least one material with high ionization energy. The ionization energy is preferably at least 5.0 eV, more preferably at least 5.5 eV. The materials may be organic or inorganic materials. Organic materials suitable for use in a layer with hole-conducting properties are preferably selected from poly(3,4-ethylenedioxythiophene) poly(styrenesulfonate) (PEDOT-PSS), Ir-DPBIC (tris-N,N'-diphenylbenzimidazol-2-ylideneiridium(III)), N,N'-diphenyl-N,N'-bis(3-methylphenyl)-1,1'-diphenyl-4,4'-diamine (α-NPD), 2,2',7,7'-tetrakis(N,N-di-p-methoxyphenylamine)-9,9'-spirobifluorene (spiro-MeOTAD), etc. and mixtures thereof. The organic materials may, if desired, be doped with a p-dopant which has a LUMO within the same range as or lower than the HOMO of the hole-conducting material. Suitable dopants are, for example, 2,3,5,6-tetrafluoro-7,7,8,8-tetracyanoquinodimethane ($F_4TCNQ$), $WO_3$, $MoO_3$, etc. Inorganic materials suitable for use in a layer with hole-conducting properties are preferably selected from $WO_3$, $MoO_3$, etc.

If present, the thickness of the layers with hole-conducting properties is preferably within a range from 5 to 200 nm, more preferably 10 to 100 nm.

Layer (13) comprises at least one compound of the general formula (I). The thickness of the layer should be sufficient to absorb a maximum amount of light, but thin enough to enable effective dissipation of the charge. The thickness of the layer (13) is preferably within a range from 5 nm to 1 μm, more preferably from 5 to 100 nm.

Layer (14) comprises at least one acceptor material. The acceptor material preferably comprises at least one fullerene or fullerene derivative. Alternatively or additionally suitable acceptor materials are specified hereinafter. The thickness of the layer should be sufficient to absorb a maximum amount of light, but thin enough to enable effective dissipation of the charge. The thickness of the layer (14) is preferably within a range from 5 nm to 1 μm, more preferably from 5 to 80 nm.

Solar cells with normal structure optionally comprise an exciton-blocking and/or electron-conducting layer (15) (EBL/ETL). Suitable materials for exciton-blocking layers generally have a greater band gap than the materials of layer (13) and/or (14). They are firstly capable of reflecting excitons and secondly enable good electron transport through the layer. The materials for the layer (15) may comprise organic or inorganic materials. Suitable organic materials are preferably selected from 2,9-dimethyl-4,7-diphenyl-1, 10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. Inorganic materials suitable for use in a layer with electron-conducting properties are preferably selected from ZnO, etc. If present, the thickness of the layer (15) is preferably within a range from 5 to 500 nm, more preferably 10 to 100 nm.

Layer 16 is the cathode and preferably comprises at least one compound with low work function, more preferably a metal such as Ag, Al, Mg, Ca, etc. The thickness of the layer (16) is preferably within a range from about 10 nm to 10 μm, e.g. 10 nm to 60 nm.

In a further suitable embodiment, the inventive solar cells are present as an individual cell with a flat heterojunction and inverse structure.

In a specific embodiment, the cell has the following structure:

an at least partly transparent conductive layer (cathode) (11)
an exciton-blocking and/or electron-conducting layer (12)
a layer which comprises an acceptor material (13)
a layer which comprises a donor material (14)
a hole-conducting layer (hole transport layer, HTL) (15)
a second conductive layer (back electrode, anode) (16)

With regard to suitable and preferred materials for the layers (11) to (16), reference is made to the above remarks regarding the corresponding layers in solar cells with normal structure.

In a further preferred embodiment, the inventive solar cells are present as an individual cell with normal structure and have a bulk heterojunction. In a specific embodiment, the cell has the following structure:

an at least partly transparent conductive layer (anode) (21)
a hole-conducting layer (hole transport layer, HTL) (22)
a mixed layer which comprises a donor material and an acceptor material, which form a donor-acceptor heterojunction in the form of a bulk heterojunction (23)
an electron-conducting layer (24)
an exciton-blocking and/or electron-conducting layer (25)
a second conductive layer (back electrode, cathode) (26)

The layer (23) comprises at least one compound of the general formula (I) as a photoactive material, e.g. as a donor material. The layer (23) additionally comprises a complementary semiconductor material, e.g. at least one fullerene or fullerene derivative as an acceptor material. The layer (23) comprises especially C60 or PCBM ([6,6]-phenyl-C61-butyric acid methyl ester) as an acceptor material.

With regard to layer (21), reference is made completely to the above remarks regarding layer (11).

With regard to layer (22), reference is made completely to the above remarks regarding layer (12).

Layer (23) is a mixed layer which comprises at least one compound of the general formula (I) as a semiconductor material. In addition, layer (23) comprises at least one complementary semiconductor material. As described above, the layer (23) can be produced by coevaporation or by solution processing using customary solvents. The mixed layer comprises preferably 10 to 90% by weight, more preferably 20 to 80% by weight, of at least one compound of the general formula (I), based on the total weight of the mixed layer. The mixed layer comprises preferably 10 to 90% by weight, more preferably 20 to 80% by weight, of at least one acceptor material, based on the total weight of the mixed layer. The thickness of the layer (23) should be sufficient to absorb a maximum amount of light, but thin enough to enable effective dissipation of the charge. The thickness of the layer (23) is preferably within a range from 5 nm to 1 µm, more preferably from 5 to 200 nm, especially 5 to 80 nm.

Solar cells with a bulk heterojunction comprise an electron-conducting layer (24) (ETL). This layer comprises at least one electron transport material (ETM). Layer (24) may be a single layer of essentially homogeneous composition or may comprise two or more than two sublayers. Suitable materials for electron-conducting layers generally have a low work function or ionization energy. The ionization energy is preferably not more than 3.5 eV. Suitable organic materials are preferably selected from the aforementioned fullerenes and fullerene derivatives, 2,9-dimethyl-4,7-diphenyl-1,10-phenanthroline (BCP), 4,7-diphenyl-1,10-phenanthroline (Bphen), 1,3-bis[2-(2,2'-bipyridin-6-yl)-1,3,4-oxadiazo-5-yl]benzene (BPY-OXD), etc. The organic materials used in layer (24) may, if desired, be doped with an n-dopant which has a HOMO within the same range as or lower than the LUMO of the electron-conducting material. Suitable dopants are, for example, $Cs_2CO_3$, Pyronin B (PyB), Rhodamine B, cobaltocenes, etc. The thickness of the layer (23) is, if present, preferably within a range from 1 nm to 1 µm, particularly 5 to 60 nm.

With regard to layer (25), reference is made completely to the above remarks regarding layer (15).

With regard to layer (26), reference is made completely to the above remarks regarding layer (16).

Solar cells with a donor-acceptor heterojunction in the form of a bulk heterojunction can be produced by a gas phase deposition process as described above. With regard to deposition rates, substrate temperature during the deposition and thermal aftertreatment, reference is made to the above remarks.

In a further preferred embodiment, the inventive solar cells are present as an individual cell with inverse structure and have a bulk heterojunction.

In a particularly preferred embodiment, the inventive solar cell is a tandem cell.

A tandem cell consists of two or more than two (e.g. 3, 4, 5, etc.) subcells. A single subcell, some of the subcells or all subcells may have photoactive donor-acceptor heterojunctions. Each donor-acceptor heterojunction may be in the form of a flat heterojunction or in the form of a bulk heterojunction. Preferably, at least one of the donor-acceptor heterojunctions is in the form of a bulk heterojunction. According to the invention, the photoactive layer of at least one subcell comprises a compound of the general formula (I). Preferably, the photoactive layer of at least one subcell comprises a compound of the general formula (I) and at least one fullerene or fullerene derivative.

More preferably, the semiconductor mixture used in the photoactive layer of at least one subcell consists of a compound of the general formula (I) and $C_{60}$ or [6,6]-phenyl-C61-butyric acid methyl ester.

The subcells which form the tandem cell may be connected in parallel or in series. The subcells which form the tandem cell are preferably connected in series. There is preferably an additional recombination layer in each case between the individual subcells. The individual subcells have the same polarity, i.e. generally either only cells with normal structure or only cells with inverse structure are combined with one another.

The inventive tandem cell preferably comprises a transparent conductive layer (layer 31). Suitable materials are those specified above for the individual cells. Layers 32 and 34 constitute subcells. "Subcell" refers here to a cell as defined above without cathode and anode. The subcells may, for example, either all have a compound of the general formula (I) used in accordance with the invention in the photoactive layer (preferably in combination with a fullerene or fullerene derivative, especially C60) or have other combinations of semiconductor materials, for example C60 with zinc phthalocyanine, C60 with oligothiophene (such as DCV5T). In addition, individual subcells may also be configured as dye-sensitized solar cells or polymer cells.

In all cases, preference is given to a combination of materials which exploit different regions of the spectrum of the incident light, for example of natural sunlight. For instance, the combination of a compound of the general formula (I) and fullerene or fullerene derivative used in accordance with the invention absorbs in the long-wave region of sunlight. Cells based on at least one perylene compound as described, for example, in International patent application WO2011158211, absorb primarily in the short-wave range. Thus, a tandem cell composed of a combination of these subcells should absorb radiation in the range from about 400 nm to 900 nm. Suitable combination of subcells should thus allow the spectral range utilized to be extended. For optimal performance properties, optical interference should be considered. For instance, subcells which absorb at relatively short wavelengths should be arranged closer to the metal top contact than subcells with longer-wave absorption.

With regard to layer (31), reference is made completely to the above remarks regarding layers (11) and (21).

With regard to layers (32) and (34), reference is made completely to the above remarks regarding layers (12) to (15) for flat heterojunctions and (22) to (25) for bulk heterojunctions.

Layer 33 is a recombination layer. Recombination layers enable the charge carriers from one subcell to recombine with those of an adjacent subcell. Small metal clusters are suitable, such as Ag, Au or combinations of highly n- and p-doped layers. In the case of metal clusters, the layer thickness is preferably within a range from 0.5 to 5 nm. In the case of highly n- and p-doped layers, the layer thickness is preferably within a range from 5 to 40 nm. The recombination layer generally connects the electron-conducting layer of a subcell to the hole-conducting layer of an adjacent subcell. In this way, further cells can be combined to form the tandem cell.

Layer 36 is the top electrode. The material depends on the polarity of the subcells. For subcells with normal structure, preference is given to using metals with a low work function, such as Ag, Al, Mg, Ca, etc. For subcells with inverse structure, preference is given to using metals with a high work function, such as Au or Pt, or PEDOT-PSS.

In the case of subcells connected in series, the overall voltage corresponds to the sum of the individual voltages of all subcells. The overall current, in contrast, is limited by the lowest current of one subcell. For this reason, the thickness of each subcell should be optimized such that all subcells have essentially the same current.

Examples of different kinds of donor-acceptor heterojunctions are a donor-acceptor double layer with a flat heterojunction, or the heterojunction is configured as a hybrid planar-mixed heterojunction or gradient bulk heterojunction or annealed bulk heterojunction.

The production of a hybrid planar-mixed heterojunction is described in Adv. Mater. 17, 66-70 (2005). In this structure, mixed heterojunction layers which were formed by simultaneous evaporation of acceptor and donor material are present between homogeneous donor and acceptor material.

In a specific embodiment of the present invention, the donor-acceptor-heterojunction is in the form of a gradient bulk heterojunction. In the mixed layers composed of donor and acceptor materials, the donor-acceptor ratio changes gradually. The form of the gradient may be stepwise or linear. In the case of a stepwise gradient, the layer 01 consists, for example, of 100% donor material, layer 02 has a donor/acceptor ratio >1, layer 03 has a donor/acceptor ratio=1, layer 04 has a donor/acceptor ratio <1, and layer 05 consists of 100% acceptor material. In the case of a linear gradient, layer 01 consists, for example, of 100% donor material, layer 02 has a decreasing ratio of donor/acceptor, i.e. the proportion of donor material decreases in a linear manner in the direction of layer 03, and layer 03 consists of 100% acceptor material. The different donor-acceptor ratios can be controlled by means of the deposition rate of each and every material. Such structures can promote the percolation path for charges.

In a further specific embodiment of the present invention, the donor-acceptor heterojunction is configured as an annealed bulk heterojunction; see, for example, Nature 425, 158-162, 2003. The process for producing such a solar cell comprises an annealing step before or after the metal deposition. As a result of the annealing, donor and acceptor materials can separate, which leads to more extended percolation paths.

In a further specific embodiment of the present invention, the organic solar cells are produced by organic vapor phase deposition, either with a flat or a controlled heterojunction architecture. Solar cells of this type are described in Materials, 4, 2005, 37.

The organic solar cells of the invention preferably comprise at least one photoactive region which comprises at least one compound of the formula (I), which is in contact with at least one complementary semiconductor. In addition to compounds of the formula (I), the semiconductor materials listed hereinafter are suitable in principle for use in solar cells according to the invention.

Preferred further semiconductors are fullerenes and fullerene derivatives, preferably selected from $C_{60}$, $C_{70}$, $C_{84}$, phenyl-$C_{61}$-butyric acid methyl ester ([60]PCBM), phenyl-$C_{71}$-butyric acid methyl ester ([71]PCBM), phenyl-$C_{84}$-butyric acid methyl ester ([84]PCBM), phenyl-$C_{61}$-butyric acid butyl ester ([60]PCBB), phenyl-$C_{61}$-butyric acid octyl ester ([60]PCBO), thienyl-$C_{61}$-butyric acid methyl ester ([60]ThCBM) and mixtures thereof. Particular preference is given to $C_{60}$, [60]PCBM and mixtures thereof. Preference is given to those fullerenes which are vaporizable, for example C60 or C70. Fullerenes and fullerene derivatives in combination with at least one compound of the formula (I) usually act as acceptors.

Suitable further semiconductors are perylendiimides different from the compounds of formula (I). Suitable are e.g. perylendiimides of the formula

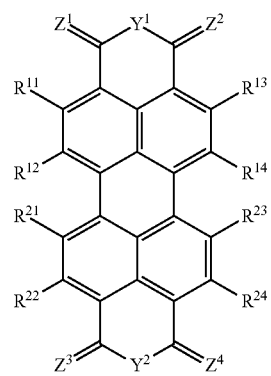

in which
the $R^{11}$, $R^{12}$, $R^{13}$, $R^{14}$, $R^{21}R^{22}$, $R^{23}$ and $R^{24}$ radicals are each independently hydrogen, halogen or groups other than halogen,
$Y^1$ is O or $NR^a$ where $R^a$ is hydrogen or an organyl radical,
$Y^2$ is O or $NR^b$ where $R^b$ is hydrogen or an organyl radical,
$Z^1$, $Z^2$, $Z^3$ and $Z^4$ are each O,
where, in the case that $Y^1$ is $NR^a$, one of the $Z^1$ and $Z^2$ radicals may also be $NR^c$, where the $R^a$ and $R^c$ radicals together are a bridging group having 2 to 5 atoms between the flanking bonds, and
where, in the case that $Y^2$ is $NR^b$, one of the $Z^3$ and $Z^4$ radicals may also be $NR^d$, where the $R^b$ and $R^d$ radicals together are a bridging group having 2 to 5 atoms between the flanking bonds.

Suitable perylendiimides are, for example, described in WO 2007/074137, WO 2007/093643 and WO 2007/116001, to which reference is made here.

Perylendiimides in combination with at least one compound of the formula (I) may act as donors or acceptors, depending inter alia on the substituents of the perylene diimides.

Further suitable semiconductors are thiophene compounds. These are preferably selected from thiophenes, oligothiophenes and substituted derivatives thereof. Suitable oligothiophenes are quaterthiophenes, quinquethiophenes, sexithiophenes, α,ω-di($C_1$-$C_8$)-alkyloligothiophenes, such as α,ω-dihexylquaterthiophenes, α,ω-dihexylquinquethiophenes and α,ω-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially α,ω-alkyl-substituted phenylene-thiophene oligomers.

Further thiophene compounds suitable as semiconductors are preferably selected from compounds like
α,α'-bis(2,2-dicyanovinyl)quinquethiophene (DCV5T),
(3-(4-octylphenyl)-2,2'-bithiophene) (PTOPT),
and acceptor-substituted oligothiophenes as described in WO 2006/092124.

Thiophene compounds in combination with at least one compound of the formula (I) usually act as donors.

Further semiconductors suitable as donors are merocyanines as described in WO 2010/049512.

All aforementioned semiconductors may be doped. The conductivity of semiconductors can be increased by chemical doping techniques using dopants. An organic semiconductor material may be doped with an n-dopant which has a HOMO energy level which is close to or higher than the LUMO energy level of the electron-conducting material. An organic semiconductor material may also be doped with a p-dopant which has a LUMO energy level which is close to or higher than the HOMO energy level of the hole-conducting material. In other words, in the case of n-doping an electron is released from the dopant, which acts as the donor, whereas in the case of p-doping the dopant acts as an acceptor which accepts an electron.

Suitable dopants for the compounds (I) according to the invention and for p-semiconductors in general are, for example, selected from $WO_3$, $MoO_3$, 2,3,5,6-tetrafluoro-7,7,8,8-tetracyanoquinodimethane ($F_4$-TCNQ), 3,6-difluoro-2,5,7,7,8,8-hexacyanoquinodimethane, dichlorodicyanoquinone (DDQ) or tetracyanoquinodimethane (TCNQ). A preferred dopant is 3,6-difluoro-2,5,7,7,8,8-hexacyanoquinodimethane.

Further suitable dopants are, for example, selected from $Cs_2CO_3$, LiF, Pyronin B (PyB), rhodamine derivatives, cobaltocenes, etc. Preferred dopants are Pyronin B and rhodamine derivatives, especially rhodamine B.

The dopants are typically used in an amount of up to 10 mol %, preferably up to 5 mol %, based on the amount of the semiconductor to be doped.

The invention further provides an electroluminescent (EL) arrangement comprising an upper electrode, a lower electrode, wherein at least one of said electrodes is transparent, an electroluminescent layer and optionally an auxiliary layer, wherein the electroluminescent arrangement comprises at least one compound of the formula I as defined above. An EL arrangement is characterized by the fact that it emits light when an electrical voltage is applied with flow of current. Such arrangements have been known for a long time in industry and technology as light-emitting diodes (LEDs). Light is emitted on account of the fact that positive charges (holes) and negative charges (electrons) combine with the emission of light. In the sense of this application the terms electroluminescing arrangement and organic light-emitting diode (OLEDs) are used synonymously. As a rule, EL arrangements are constructed from several layers. At least on of those layers contains one or more organic charge transport compounds. The layer structure is in principle as follows:
1. Carrier, substrate
2. Base electrode (anode)
3. Hole-injecting layer
4. Hole-transporting layer
5. Light-emitting layer
6. Electron-transporting layer
7. Electron-injecting layer
8. Top electrode (cathode)
9. Contacts
10. Covering, encapsulation.

This structure represents the most general case and can be simplified by omitting individual layers, so that one layer performs several tasks. In the simplest case an EL arrangement consists of two electrodes between which an organic layer is arranged, which fulfils all functions, including emission of light. The structure of organic light-emitting diodes and processes for their production are known in principle to those skilled in the art, for example from WO 2005/019373. Suitable materials for the individual layers of OLEDs are disclosed, for example, in WO 00/70655. Reference is made here to the disclosure of these documents. In principle OLEDs according to the invention can be produced by methods known to those skilled in the art. In a first embodiment, an OLED is produced by successive vapor deposition of the individual layers onto a suitable substrate. For vapor deposition, it is possible to use customary techniques such as thermal evaporation, chemical vapor deposition and others. In an alternative embodiment, the organic layers may be coated from solutions or dispersions in suitable solvents, for which coating techniques known to those skilled in the art are employed.

Suitable as substrate 1 are transparent carriers, such as glass or plastics films (for example polyesters, such as polyethylene terephthalate or polyethylene naphthalate, polycarbonate, polyacrylate, polysulphone, polyimide foil). Suitable as transparent and conducting materials are a) metal oxide, for example indium-tin oxide (ITO), tin oxide (NESA), etc. and b) semi-transparent metal films, for example Au, Pt, Ag, Cu, etc.

The compounds of the formula (I) preferably serve as a charge transport material (electron conductor). Thus, at least one compound of the formula I as defined above is preferably used in a hole-injecting layer, hole transporting layer or as part of a transparent electrode.

In the EL applications according to the invention low molecular weight or oligomeric as well as polymeric materials may be used as light-emitting layer 5. The substances are characterized by the fact that they are photoluminescing. Accordingly, suitable substances are for example fluorescent colorants and fluorescent products that are forming oligomers or are incorporated into polymers. Examples of such materials are coumarins, perylenes, anthracenes, phenanthrenes, stilbenes, distyryls, methines or metal complexes such as $Alq_3$ (tris(8-hydroxyquinolinato)aluminium), etc. Suitable polymers include optionally substituted phenylenes, phenylene vinylenes or polymers with fluorescing segments in the polymer side chain or in the polymer backbone. A detailed list is given in EP-A-532 798. Preferably, in order to increase the luminance, electron-injecting or hole-injecting layers (3 and/or 7) can be incorporated into the EL arrangements. A large number of organic compounds that transport charges (holes and/or electrons) are described in the literature. Mainly low molecular weight substances are used, which are for example vacuum evaporated in a high vacuum. A comprehensive survey of the classes of substances and their use is given for example in the following publications: EP-A 387 715, U.S. Pat. Nos. 4,539,507, 4,720,432 and 4,769,292. A preferred material is PEDOT (poly-(3,4-ethylenedioxythiophene)) which can also be employed in the transparent electrode of the OLEDs.

As a result of the inventive use of the compounds (I), it is possible to obtain OLEDs with high efficiency. The inventive OLEDs can be used in all devices in which electroluminescence is useful. Suitable devices are preferably selected from stationary and mobile visual display units. Stationary visual display units are, for example, visual display units of computers, televisions, visual display units in printers, kitchen appliances and advertising panels, illuminations and information panels. Mobile visual display units are, for example, visual display units in cell phones, laptops, digital cameras, vehicles and destination displays on buses and trains. Moreover, the compounds (I) may be used in OLEDs with inverse structure. The compounds (I) in these inverse OLEDs are in turn preferably used in the light-emitting layer. The structure of inverse OLEDs and the materials typically used therein are known to those skilled in the art.

Before they are used as charge transport materials or exciton transport materials, it may be advisable to subject the compounds of the formula (I) to a purification process. Suitable purification processes comprise conventional column techniques and conversion of the compounds of the formula (I) to the gas phase. This includes purification by sublimation or PVD (physical vapor deposition).

The invention is illustrated in detail with reference to the following nonrestrictive examples.

If not stated otherwise, the reactions were performed using standard vacuum-line and Schlenk techniques, work-up and purification of all compounds were performed under air and with reagent-grade solvents. Quinoline was dried with $NaSO_4$, distilled from zinc dust and stored not longer than one month over molecular sieves (3 Å) under argon and protected from light. Column chromatography was done with silica gel (particle size 0.063-0.200 mm) from Macherey-Nagel) and silica coated aluminum sheets with fluorescence indicator from Macherey-Nagel were used for thin layer chromatography. The $^1$H-NMR and $^{13}$C-NMR spectra were recorded on a Bruker AVANCE 300, Bruker AVANCE III 500 and Bruker AVANCE III 700 spectrometer in the listed deuterated solvents. The control of the temperature was realized with a VTU (variable temperature unit) and an accuracy of +/−0.1K, which was monitored with the standard Bruker Topspin 3.1 software. Residual non-deuterated solvent was used as an internal standard. Solution UV-Vis absorption and emission spectra were recorded at room temperature on a Perkin-Elmer Lambda 900 spectrophotometer and J&MTIDAS spectrofluorometer in $CH_2Cl_2$ in a conventional quartz cell (light pass 10 mm). High-resolution electrospray ionization mass spectrometry was performed on a Q-Tof Ultima 3 (micromass/Waters). High resolution MALDI-TOF spectra were recorded on a Waters Synapt G2-Si spectrometer with C60 as reference. Cyclic voltammetry measurements were performed with a Wave-Driver 20 Bipotentiostat/Galvanostat (Pine Instruments Company). High-performance-liquid chromatography was performed on an Agilent 1200 series.

Abbreviations used: DCM stands for dichloromethane; $(CDCl_2)_2$ stands for deuterotetrachloroethane; DMSO stands for dimethyl sulfoxide; EtOH stand for ethanol; THF stands for tetrahydrofuran; eq stands for equivalents.

I. PREPARATION EXAMPLES

Example 1

Benzo[4,5]isoquinolino[2,1-a]quinoline-7,13-dione

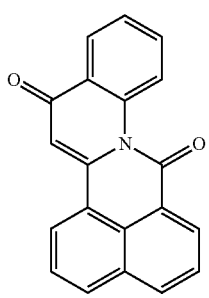 [SMILES: O=c1cc2c3cccc4cccc(c(=O)n2c2ccccc12)c43]

Approach a:

In a flame-dried Schlenk flask 1.0 g (5.05 mmol) of 1,8-naphthalic anhydride, 0.72 g (5.33 mmol) of 2-acetyl aniline and 0.75 g (0.81 eq, 4.09 mmol) zinc acetate were suspended in 10 mL of freshly distilled quinoline. The reaction mixture was degassed by evacuation and purging three times with argon and was heated to 180° C. under argon for 48 h. After cooling to room temperature the reaction mixture was poured into a mixture of methanol and 1M hydrochloric acid. The precipitate was filtered and washed with water and cold methanol. The filter cake was dissolved in DCM and repeatedly precipitated from hexane to give 1.2 g of the title compound as pale yellow powder in 80% yield.

$^1$H NMR (300 MHz, $(CDCl_2)_2$, 298K) δ 7.14 (s, 1H), 7.55 (t, J=7.8 Hz, 1H), 7.90-7.67 (m, 3H), 8.15 (d, J=8.2 Hz, 1H), 8.27 (t, J=6.8 Hz, 2H), 8.34 (d, J=6.3 Hz, 1H), 8.68 (dd, J=12.4, 7.5 Hz, 2H). $^{13}$C NMR (75 MHz, $(CDCl_2)_2$, 298K) δ 178.39, 162.21, 146.48, 138.66, 134.59, 131.86, 131.84, 131.66, 131.26, 127.76, 127.47, 127.41, 126.62, 126.54, 125.97, 125.53, 123.80, 123.46, 123.13, 109.98 ppm. HRMS (ESI$^+$): calcd for $C_{20}H_{12}NO_2$ [M+H]$^+$ 298.0868. found: 298.0855. UV-Vis ($CH_2Cl_2$): $\lambda_{max}$=392 nm (19100 m$^{-1}$ cm$^{-1}$).

Approach b:

1.1b N-(2-bromophenyl)naphthalene monoimide

In a flame-dried 25 ml Schlenk flask 0.5 g (2.52 mmol) of naphthalene monoanhydride, 0.87 g (2 eq; 5.05 mmol) of 2-bromo aniline and 0.23 g (0.5 eq, 1.26 mmol) of zinc acetate were suspended in 5 mL of freshly distilled quinoline. The reaction mixture was degassed by evacuation and purging three times with argon and it was heated to 180° C. under argon for 16 h. After cooling to room temperature the reaction mixture was poured into a mixture of methanol and 2 m hydrochloric acid. The precipitate was filtered and washed with water and methanol. The residue was crystallized from EtOH/DCM to give 0.75 g (2.13 mmol) of the title compound s off-white powder in 84% yield.

$^1$H NMR (300 MHz, $CD_2Cl_2$, 298K) δ 7.41 (t, J=7.9 Hz, 1H), 7.54 (t, J=8.3 Hz, 1H), 7.82 (dd, J=14.9, 6.9 Hz, 2H), 8.34 (d, J=8.2 Hz, 1H), 8.63 (d, J=8.3 Hz, 1H). $^{13}$C NMR (75 MHz, $CD_2Cl_2$, 298K) δ 163.84, 135.99, 134.97, 133.69, 132.31, 131.87, 131.07, 130.74, 128.92, 127.43, 123.50, 122.96 ppm. HRMS (ESI$^+$): calcd for $C_{18}H_{11}NO_2Br$ [M+H]$^+$ 351.9979. found: 351.9973.

1.2b N-(2-acetylphenyl)naphthalene monoimide

In a flame-dried 100 ml Schlenk flask 0.7 g (2 mmol) of N-(2-bromophenyl)naphthalene monoimide were dissolved in 40 mL of dry toluene and thoroughly degassed by purging with argon for 30 min. Then 0.86 g of tributyl(1-ethoxyvinyl)tin (1.2 eq, 2.39 mmol) were added and the system was purged for additional 5 minutes. Under argon atmosphere 0.1 eq tetrakis(triphenylphosphine)palladium (0.23 g; 0.2 mmol) were added and the reaction mixture was heated to 110° C. for 16 hours. After cooling to room temperature the reaction mixture was poured into 100 mL of 2M hydrochloric acid and vigorously stirred for four hours. The reaction mixture was extracted with DCM and the combined organic layers were washed with brine, dried with sodium sulfate and the solvents were evaporated. After column chromatography (silica; DCM/PE) and crystallization from DCM/hexane 0.45 g (1.43 mmol) of the title compound were obtained as colorless crystals in 72% yield.

1.2c Benzo[4,5]isoquinolino[2,1-a]quinoline-7,13-dione

A mixture of N-(2-acetylphenyl)naphthalene monoimide, catalytic amounts of zinc acetate was heated in quinoline at 180° C. for 24 h to give the title compound in a yield of 82%.

Example 2

2-(7-oxobenzo[4,5]isoquinolino[2,1-a]quinolin-13(7H)-ylidene)malononitrile

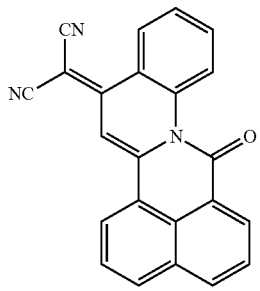 [SMILES: N#CC(C#N)=c1cc2c3cccc4cccc(c(=O)n2c2ccccc12)c43]

In a 25 mL round bottom flask equipped with a reflux condenser 0.1 g (0.34 mmol) of benzo[4,5]isoquinolino[2,1-a]quinoline-7,13-dione were dissolved in a mixture of 10 mL of acetic anhydride and 5 mL of acetic acid and 45 mg (2 eq, 0.68 mmol) of malononitrile were added. The reaction mixture was heated to reflux and stirred for 48 hours. The solvents were evaporated under reduced pressure and the residue was purified by column chromatography (silica, DCM) to attain 36 mg (0.104 mmol) of the title compound in 31% yield.

$^1$H NMR (700 MHz, (CDCl$_2$)$_2$, 298K) δ 7.61 (t, J=7.7 Hz, 1H), 7.63 (s, 1H), 7.82-7.75 (m, 2H), 7.87 (t, J=7.7 Hz, 1H), 8.20 (d, J=8.1 Hz, 1H), 8.31 (d, J=8.1 Hz, 1H), 8.37 (d, J=7.5 Hz, 1H), 8.62 (d, J=8.6 Hz, 1H), 8.70 (d, J=7.1 Hz, 1H), 8.77 (d, J=8.2 Hz, 1H) ppm. $^{13}$C NMR (176 MHz, (CDCl$_2$)$_2$, 298K) δ 161.15, 153.21, 142.84, 135.21, 135.09, 132.42, 132.21, 131.77, 131.73, 127.63, 127.48, 127.19, 126.62, 126.31, 125.28, 124.03, 122.53, 122.15, 116.86, 116.11, 107.50 ppm. HRMS (ESI$^+$): calcd for C$_{23}$H$_{12}$N$_3$O [M+H]$^+$ 346.0980. found: 346.0991. UV-Vis (CH$_2$Cl$_2$): $\lambda_{max}$=463 nm (27100 m$^{-1}$ cm$^{-1}$).

Example 3

8,9,14,15-tetra-tert-octyl-phenoxy-benzo[5',10']anthra[2',1',9':4,5,6]-isoquinolino[2,1-a]quinoline-6,18-dione In a flame-dried 25 ml Schlenk flask 50 mg (0.044 mmol) of tetra-tert-octyl-phenoxy perylene mono anhydride, 10 mg (0.074 mmol) of 2-acetyl aniline and 4 mg (0.022 mmol) zinc acetate were suspended in 2.5 mL of freshly distilled quinoline. The reaction mixture was degassed by evacuation and purging three times with argon and it was heated to 180° C. under argon for 70 h. After cooling to room temperature the reaction mixture was poured into methanol and the precipitate was filtered and washed methanol. The residue was purified by column chromatography (silica, DCM) to attain 25 mg (0.02 mmol) of the title compound in 46% yield.

$^1$H NMR (300 MHz, CD$_2$Cl$_2$, 298K) δ 0.72-0.81 (m, 36H), 1.31-1.40 (m, 24H), 1.74 (s, 8H), 6.73 (s, 1H), 6.81-6.89 (m, 8H), 7.12 (d, J=8.9 Hz, 2H), 7.24-7.32 (m, 8H), 7.47 (t, J=7.9 Hz, 1H), 7.64 (t, J=7.9 Hz, 1H), 7.70-7.80 (m, 2H), 7.83 (s, 1H), 8.13 (s, 1H), 8.23 (d, J=9.6 Hz, 1H), 8.67 (d, J=8.6 Hz, 1H) ppm. $^{13}$C NMR (75 MHz, CD$_2$Cl$_2$, 298K) δ 154.79, 154.72, 153.96, 153.90, 153.84, 146.46, 146.40, 146.31, 146.23, 146.15, 131.62, 130.30, 129.91, 128.04, 127.92, 127.73, 126.47, 125.54, 124.90, 123.95, 123.71, 121.92, 119.63, 119.41, 117.64, 117.44, 116.18, 115.04, 109.83, 57.32, 57.21, 38.55, 32.68, 32.61, 31.99, 31.82, 31.73, 30.07 ppm. HRMS (ESI$^+$): calcd for C$_{86}$H$_{96}$NO$_6$ [M+H]$^+$ 1238.7238. found: 1238.7255. UV-Vis (CH$_2$Cl$_2$): $\lambda_{max}$=573 nm (23300 m$^{-1}$ cm$^{-1}$).

Example 4

8,9,20,21-tetra-tert-octyl-phenoxy-anthra[2',1',9':4,5,6;10',5',6':4,5,6]diisoquinolino[2,1-a]quinoline-6,11,17,24-tetrone

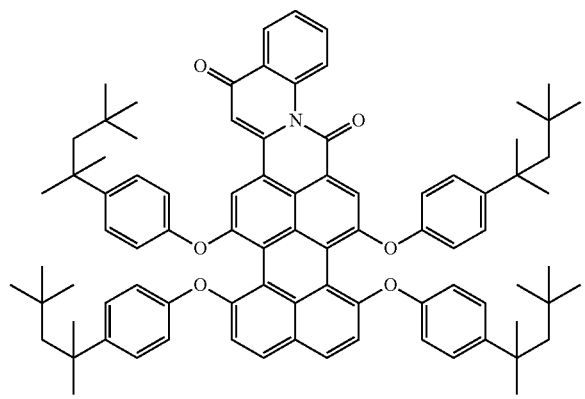 [SMILES: CC(C)(C)CC(C)(C)c1ccc(Oc2ccc3ccc(Oc4ccc(C(C)(C)CC(C)(C)C)cc4)c4c5c(Oc6ccc(C(C)(C)CC(C)(C)C)cc6)cc6c7c(cc(Oc8ccc(C(C)(C)CC(C)(C)C)cc8)c(c2c34)c57)c(=O)n2c3ccccc3c(=O)cc62)cc1]

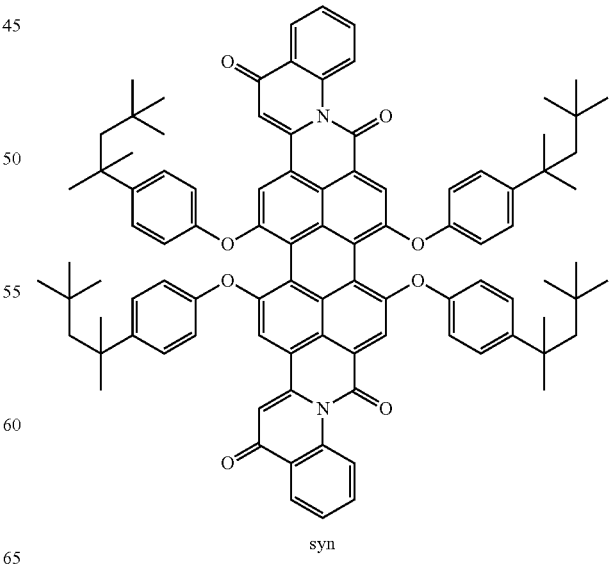

syn

-continued

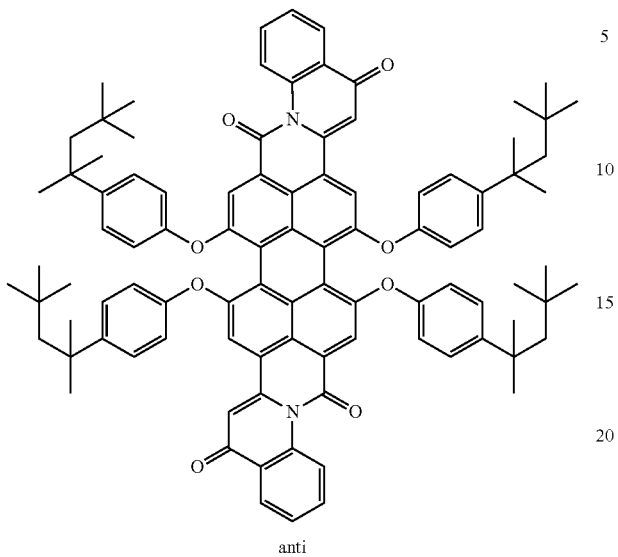

anti

In a flame dried 25 ml Schlenk flask 363 mg (0.3 mmol) of 1,6,7,12-tetra-tert-octyl-phenoxy perylene tetracarboxylic acid bis anhydride, 134 mg (0.99 mmol) of 2-acetyl aniline, 50 mg zinc acetate (0.27 mmol) and 15 ml of freshly distilled quinoline were added and the solution was degassed three times. It was heated to 200° C. under argon for 48 h. After cooling to room temperature the reaction mixture was added to methanol, the precipitate was filtered and washed with methanol. The crude product was dissolved in DCM and again precipitated from methanol. The resulting precipitate was filtered and purified by column chromatography on silica with DCM as eluent. After crystallization from isopropanol the product was obtained as blue powder in 24% yield as mixture of its syn- and anti-isomers (99 mg; 0.07 mmol).

$^1$H NMR (300 MHz, CD$_2$Cl$_2$, 298K) δ 0.84 (dd, J=18.2 Hz, 36H), 1.41 (dd, J=15.0 Hz, 24H), 1.79 (dd, J=15.7 Hz, 8H), 6.59 (m, 4H), 6.88 (br, 4H), 7.15 (d, J=8.34 Hz, 2H), 7.35 (m, 12H), 7.52 (br, 2H), 7.95 (d, J=22.5 Hz, 2H), 8.03 (br, 2H), 8.49 (br, 2H) ppm. $^{13}$C NMR (75 MHz, CD$_2$Cl$_2$, 298K) δ 177.61, 161.14, 156.90, 153.46, 152.80, 147.51, 147.25, 147.09, 146.84, 145.38, 145.31, 138.61, 131.74, 128.16, 127.90, 126.06, 125.37, 124.03, 123.73, 123.33, 123.01, 120.59, 119.26, 118.95, 115.01, 57.51, 57.41, 38.83, 38.76, 38.71, 38.65, 32.81, 32.72, 32.67, 32.25, 32.10, 31.94, 31.67. ppm. HRMS (ESI$^+$): calcd for C$_{96}$H$_{99}$N$_2$O$_8$ [M+H]$^+$ 1407.7401. found: 1407.7355. UV-Vis (CH$_2$Cl$_2$): $\lambda_{max}$=633 nm (62800 m$^{-1}$ cm$^{-1}$).

Fluorescence: $\lambda_{em}$=664 nm (0=65% vs Rhodamine 800)

Example 5 anthra[2',1',9':4,5,6;10',5',6':4,5,6]diisoquinolino[2,1-a]quinoline-6,12,18,24-tetrone

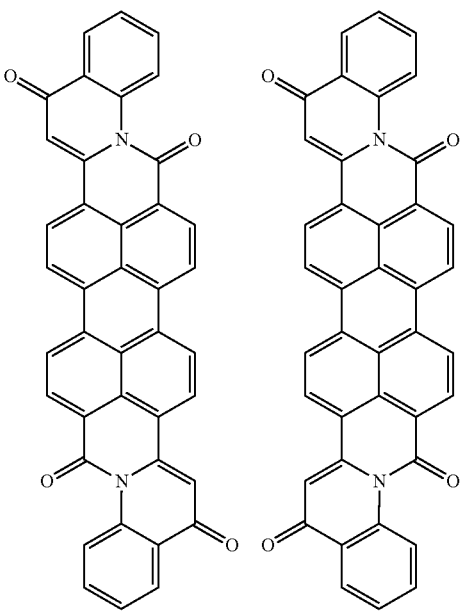

In a flame dried 25 ml Schlenk flask 300 mg (0.76 mmol) of perylene tetracarboxylic acid bisanhydride, 228 mg (1.68 mmol) of 2-acetyl aniline, 14 mg zinc acetate (0.076 mmol) and 7.5 ml of freshly distilled quinoline were added. The suspension was degassed three times. It was heated to 200° C. under argon for 70 h. After cooling to room temperature the reaction mixture was added to methanol. The resulting precipitate was filtered and suspended in 1M NaOH solution to remove remaining anhydrides. After filtration the solid was washed successively with methanol, DCM and THF. The filter cake was continuously washed with DCM by a Soxhlett extractor to leave the product as purple powder with golden shine in 53% yield as mixture of its syn- and anti-isomers (240 mg; 0.41 mmol).

$^1$H NMR (700 MHz, (TFA/CDCl$_2$)$_2$, 298K) δ 7.47 (t, 2H), 7.77 (t, 2H), 7.92 (s, 2H), 8.19 (d, 2H), 8.49 (dd, 4H), 8.58 (dd, 4H), 8.76 (d, 2H). MALDI-TOF: m/z (%): calcd for 590.59. found: 589.73 (100) [M]$^+$. UV-Vis (trifluoroacetic acid): $\lambda_{max}$=630 nm. UV-Vis (solid state): $\lambda_{max}$=578 nm.

Example 6

8,9,20,21-tetra-phenoxy-anthra[2',1',9':4,5,6;10',5',6':4,5,6]diisoquinolino[2,1-a]quinoline-6,11,17,24-tetrone In a flame dried 25 ml Schlenk flask 350 mg (0.46 mmol) of 1,6,7,12-tetra-phenoxy perylene tetracarboxylic acid bisanhydride, 134 mg (2.2 eq; 0.99 mmol) of 2-acetyl aniline, 83 mg zinc acetate (1 eq, 0.51 mmol) and 15 ml freshly distilled quinoline were added and the solution was degassed three times. It was heated to 200° C. under argon for 24 h. After cooling to room temperature the reaction mixture was added to methanol, the precipitate was filtered and washed with methanol. The crude product was dissolved in DCM and again precipitated from methanol. After crystallization from isopropanol the product was obtained as blue powder in 25% yield as mixture of its syn- and anti-isomers (110 mg; 0.115 mmol).

$^1$H NMR (500 MHz, C$_2$D$_2$Cl$_4$, 393K) δ 8.81 (bs, 2H), 8.35 (bs, 4H), 7.97 (bs, 2H), 7.71 (bs, 2H), 7.53 (bs, 2H), 7.37 (bs, 8H), 7.21 (bs, 4H), 7.08 (bs, 8H), 6.87 (bs, 2H) ppm. $^{13}$C NMR (126 MHz, C$_2$D$_2$Cl$_4$) δ 131.87, 131.12, 130.15, 129.99, 126.49, 125.72, 124.78, 124.03, 123.49, 120.13, 120.01, 119.97, 119.77, 119.72, 117.05, 115.55, 115.41, 112.79, 110.84, 110.00, 79.98 ppm. MALDI-TOF: M/z=958.76 (ber. 958.98; 100%); FD (8 kV): M/z=960.3 (ber. 958.98; 100%); 480.6 (45%); UV-Vis (CH$_2$Cl$_2$): $\lambda_{max}$=607 nm (61400 m$^{-1}$ cm$^{-1}$);

Fluorescence (THF): $\lambda_{em\ (606\ nm)}$=654 nm

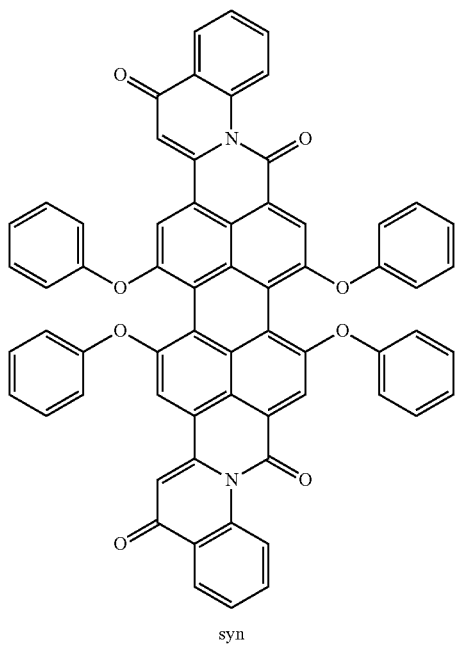

syn

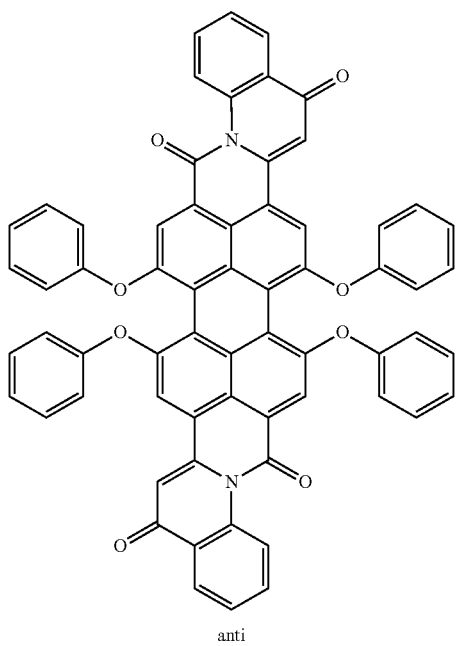

anti

Example 7

8,9,20,21-tetra-(4-sulfophenoxy)-anthra[2',1',9':4,5,6;10',5',6':4,5,6]diisoquinolino[2,1-a]quinoline-6,11,17,24-tetrone

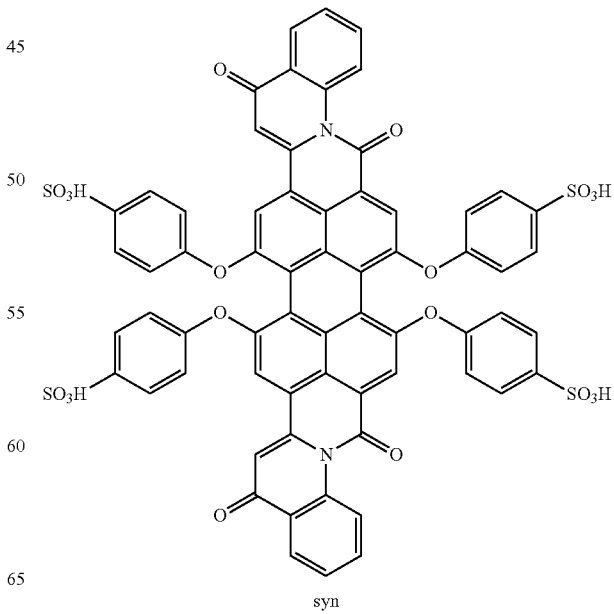

syn

87

-continued

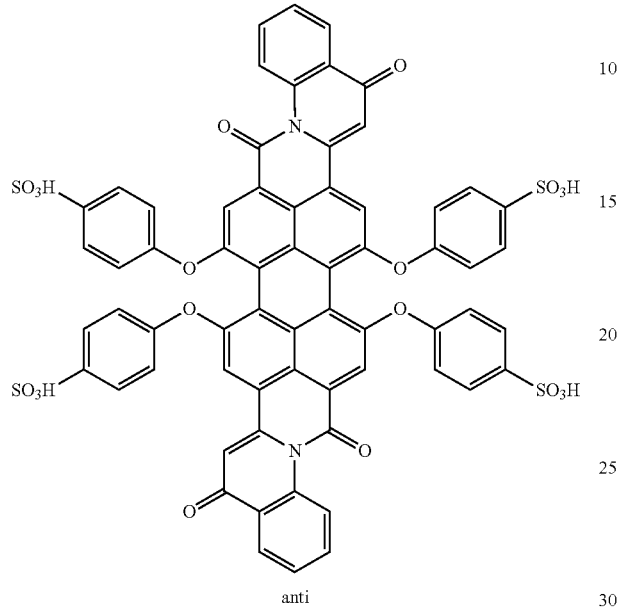

anti

In a 25 ml round bottom flask 20 mg (0.02 mmol) of 8,9,20,21-tetra-phenoxy-anthra[2',1',9':4,5,6;10',5',6':4,5,6]diisoquinolino[2,1-a]quinoline-6,11,17,24-tetrone were dissolved in 5 ml of concentrated sulfuric acid and stirred for 20 h at room temperature. Ice water was added and the solution was dialyzed (MWCO 500) in distilled water four times. The solution was freeze dried, re-dissolved in a small portion of water, precipitated from methanol and filtered to obtain 19 mg of the sulfonated product as blue powder in 71% yield (0.014 mmol).

$^1$H NMR (500 MHz, DMSO-d$_6$) δ 9.21 (m, 2H), 8.60 (m, 6H), 8.14 (m, 10H), 7.98 (t, 2H), 7.44 (m, 10H). MALDI-TOF: M/z=1281.81 (ber. 1278.06; 100%); UV-Vis (DMSO): $\lambda_{max}$=615 nm (59800 m$^{-1}$ cm$^{-1}$).

Fluorescence (DMSO): $\lambda_{em\ (578\ nm)}$=671 nm.

88

Example 8

4-Oxoquinoline-1,6,9,13-tetra-phenoxy-terrylene-3,4,11,12-tetracarboxidiimide

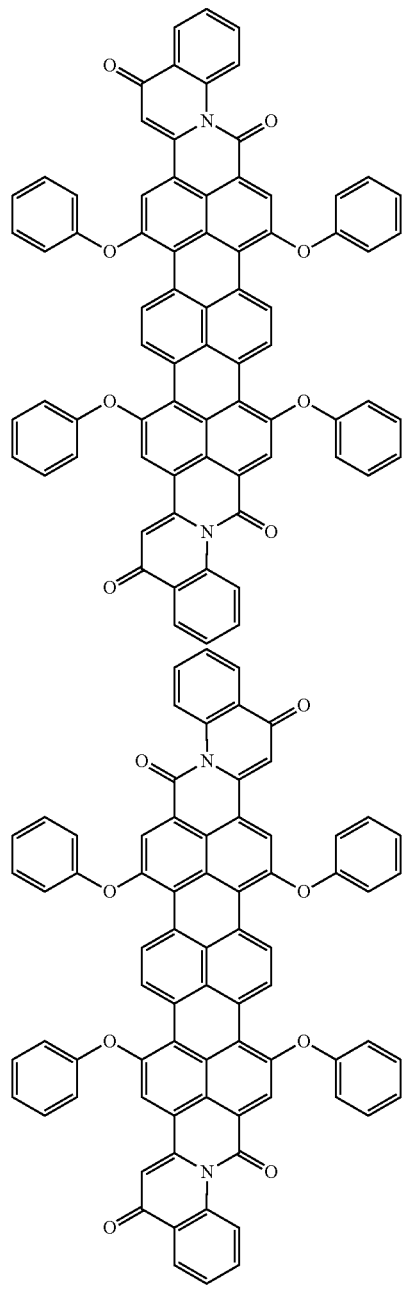

In a flame dried 25 ml Schlenk flask 23 mg (0.026 mmol) of 1,6,9,14-tetraphenoxy-terrylene-3,4,11,12-tetracarboxylic acid bis anhydride, 10 mg (2.8 eq; 0.073 mmol) of 2-acetyl aniline, 5 mg zinc acetate (1 eq, 0.026 mmol) and 1 ml freshly distilled quinoline were added and the solution was degassed three times. It was heated to 200° C. under argon for 24 h. After cooling to room temperature the reaction mixture was added to methanol, the precipitate was filtered and washed with methanol, acetone, THF and DCM. The product was dissolved in hot tetrachloroethane and precipitated from methanol. The product was obtained as green powder in 21% yield as mixture of its syn- and anti-isomers (6 mg; 0.005 mmol).

$^1$H NMR (500 MHz, Cl$_2$HCCHCl$_2$, 413K) δ 9.36 (s, 4H), 8.76 (s, 2H), 8.24 (s, 4H), 8.16 (s, 2H), 7.85 (s, 2H), 7.56 (t, 2H), 7.35 (m, 10H), 7.13 (m, 10H), 6.73 (s, 2H). MALDI-TOF: M/z=1083.27 (ber. 1083.12; 100%); UV-Vis (Cl$_2$HCCHCl$_2$): λ$_{max}$=727 nm; Fluorescence (Cl$_2$HCCHCl$_2$): λ$_{em\ (720\ nm)}$=772 nm.

II. USE EXAMPLES

A) Production of the Colored Sample Sheets

A.1) PMMA 1000.00 g of polymethyl methacrylate (PPMA 6N clear, available from Röhm GmbH, Germany) were predried at a maximum temperature of 90° C. for 4 hours and then mixed with 0.5 g of a compound of formula I in a Turbula Fuchs mixer for 20 min. The homogenous mixture was extruded on a Twin Screw 25 mm extruder from Collin, Germany, six heating zones (cold, 150° C., 195° C., 200° C., 200° C., 200° C., 200° C.) at a maximum temperature of 200° C. The extrudate was granulated in a granulator (Scheer, Stuttgart). The granulate was dried at a maximum temperature of 90° C. for 4 hours and then processed to colored sample sheets (30 mm×55 mm×1.5 mmm) using a Boy Injection Molding Machine (Boy 30 A from Dr. Boy GmbH, Neustadt, Germany) or a Klöckner Ferromatik FM 40 (from Klöckner, Germany). The mouldings were obtained were packed up in an oxygen free plastic bag with a vacuum pack machine after drying. The colored sample sheets were then subjected to colorimetry.

A.2) Soft PVC

Premix:

0.08 g of compound of formula I was mixed for 30 minutes at room temperature with a mixer with 14.0 g of a base mixture and then slowly stirred with 26.0 g of polyvinyl chloride (PVC) (EVI POL® SH 7060, EVC GmbH). The base mixture consists of plastiziser (12.9 g Palatinol® 10P (di-2-propylheptylphthalate, BASF), 0.6 g Drapex® 39 (epoxidised soya bean oil, Witco Vinyl Additives GmbH) and 0.5 g Mark BZ 561 (barium/zinc stabilizer, Chemtura GmbH).

Production of Rolled Sheets: The mixture of PVC and compound of formula (I)/base mixture obtained above was rolled in a 2-roll mill (Colin model W110P, Ebersberg, Germany) at a roll temperature of 160° C. (each roll) in accordance with the following: first cold-rolling 20 times (followed by hot-rolling for 6 minutes (rolled sheet turned every minute, roll nip 0.35 mm). This gave a milled sheet of thickness 0.33-0.35 mm.

B) Testing by Colorimetry

Color measurements on the samples were performed according to DIN 53236 (January 1983), method A. All color measurements in remission/transmission are effected using a Minolta CM 3610d spectrophotometer (d/8 geometry, including the gloss, illuminant D65, observer 10°) and B&W Leneta cards. All "angle-depending" measurements are effected using a Datacolor FX 10 and B&W Leneta cards. The CIELAB colour system according to DIN 6174 was used to evaluate the results.

The results are shown in table 2.

TABLE 2

| Sample | L* | a* | b* | C* | h° |
|---|---|---|---|---|---|
| compound of example 4* | 55.48 | −22.91 | −18.2 | 29.26 | 218.46 |
| compound of example 5# | 36.84 | 10.05 | −21.22 | 23.48 | 295.34 |

*0.2% by weight in soft-PVC prepared as described under A.2
0.02% by weight in PMMA prepared as described under A.1

III. METHOD FOR DETERMINING THE TRANSISTOR CHARACTERISTICS

Fabrication Procedure:

Highly doped silicon wafers coated with a 30 nm layer of Al$_2$O$_3$ prepared by atomic layer deposition (ALD) were thoroughly cleaned by treatment with isopropanol dried at 100° C. at ambient air on a hotplate for 10 min. The surface of the Al$_2$O$_3$ layer is treated by a brief exposure to an oxygen plasma. The substrate is then immersed into a 2-propanol solution of an alkyl phosphonic acid (0.34 mg/ml solution of C$_{10}$H$_{21}$PO(OH)$_2$), which results in the formation of a self-assembled monolayer (SAM) on the surface. The highly doped silicon is used as substrate and back gate electrode, the alkyl phosphonic acid treated Al$_2$O$_3$ acts as the gate dielectric. A 30 nm thick film of the organic semiconductor of a compound of formula (I) is deposited on the substrate at a pressure of 7×10$^{-7}$ mbar and with an evaporation rate between 0.1 and 0.5 Å/s while the substrate was held at a defined temperature. Gold source-drain contacts were defined with a shadow mask. The channel width (w) is 500 and channel length (l) is 50 μm.

The electrical characteristics of the transistors are measured on a home-build probe station using an Agilent 4156C semiconductor parameter analyzer. All measurements are performed in air at room temperature in the dark. The probe needles are brought into contact with the source and drain contacts of the transistors by putting them down carefully on top of the gold contacts. The gate electrode is contacted by breaking the gate dielectric at a certain position of the chip and pressing a probe needle onto the broken position.

The invention claimed is:

1. A compound of formula (I):

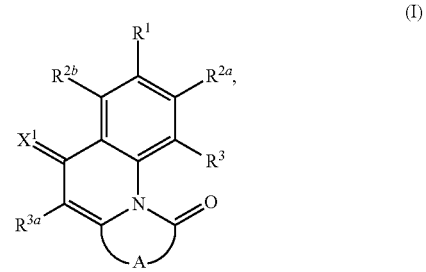

wherein:

R$^1$, R$^{2a}$ and R$^{2b}$ are independently of one another selected from the group consisting of hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, diaklaminocarbonyl, sulfo, sulfonate, sulfoamino, sulfamoyl, akisulfonyl, arylsulfonyl, amidino, NE$^1$E$^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloakythio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^3$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^{3a}$ is hydrogen, in each case unsubstituted or substituted alkyl or aryl;

$X^1$ is O or $C(CN)_2$;

A is a diradical selected from diradicals of the general formulae, (A.2), (A.3), (A.4), (A.5), and (A.6):

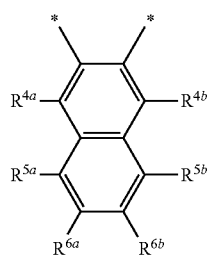

(A.2)

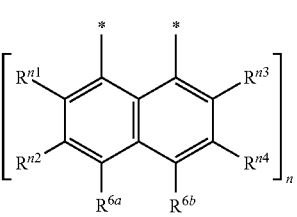

(A.3)

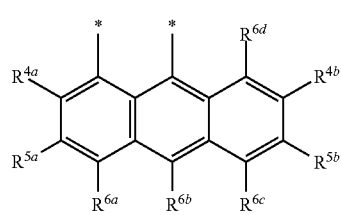

(A.4)

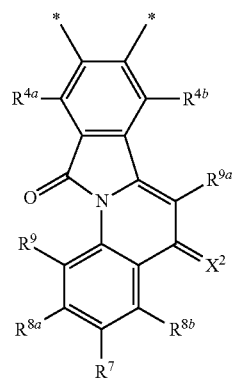

(A.5)

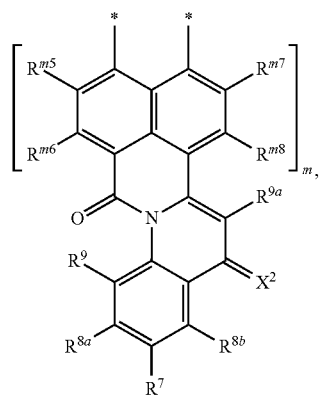

(A.6)

wherein:
* in each case denotes the point of attachments to the quinoline skeleton and the carbonyl carbon atom;
n is 1, 2, 3 or 4;
m is 1, 2, 3 or 4;
$R^{4a}$, $R^{4b}$, $R^{5a}$, $R^{5b}$, $R^{6a}$, $R^{6b}$, $R^{6c}$, $R^{6d}$, at each occurrence, $R^{n1}$, $R^{n2}$, $R^{n3}$, $R^{n4}$, $R^{m5}$, $R^{m6}$, $R^{m7}$ and $R^{m8}$, are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl) amino, aryl, aryloxy, arylthio, (monoaryl)amino, (diaryl)amino, hetaryl, hetaryloxy, hetarylthio, (monohetaryl)amino and (dihetaryl)amino;

$R^7$, $R^{8a}$, $R^{8b}$ are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^9$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, diaklaminocarbonyl, sulfo, sulfonate, sulfoamino, sulfamoyl, akisulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$R^{9a}$ is hydrogen, in each case unsubstituted or substituted alkyl or aryl; and $X^2$ is O or $C(CN)_2$;

wherein:

$E^1$ and $E^2$, at each occurrence, are each independently selected from hydrogen, alkyl, cycloalkyl, heterocycloalkyl, aryl and hetaryl.

2. The compound according to claim 1, wherein $R^1$ is hydrogen, chlorine, bromine, $C_1$-$C_{30}$-alkyl or $C_1$-$C_{30}$-haloalkyl.

3. The compound according to claim 1, wherein $R^{2a}$, $R^{2b}$, $R^3$ and $R^{3a}$ are hydrogen.

4. The compound according to claim 1, which corresponds to the formula (I-A):

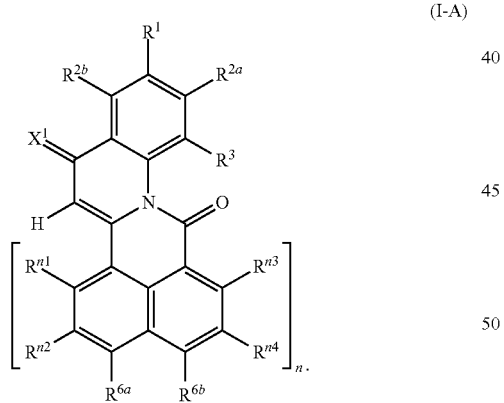

(I-A)

5. The compound according to claim 4, wherein $R^{n1}$, $R^{n2}$, $R^{n3}$, $R^{n4}$, $R^{6a}$, $R^{6b}$, are independently of one another, selected from the group consisting of hydrogen, $C_1$-$C_{30}$-alkoxy, $C_1$-$C_{30}$-alkylsulfanyl, aryloxy and arylthio where the two last mentioned radicals are unsubstituted or carry 1, 2 or 3 substituents selected from the group consisting of $SO_3H$, $C_1$-$C_{10}$-alkoxy and $C_1$-$C_{10}$-alkyl which is unsubstituted or substituted by COOH.

6. The compound according to claim 4, wherein n is 1 or 2.

7. The compound according to claim 4, wherein n is 2, and 2 or 4 of the $R^{12}$, $R^{14}$, $R^{21}$ and $R^{23}$ radicals are each phenyloxy which is unsubstituted or substituted by 1, 2 or 3 substituents selected from the group consisting of $SO_3H$, $C_1$-$C_{10}$-alkoxy and $C_1$-$C_{10}$-alkyl which is unsubstituted or substituted by COOH and the remaining radicals $R^{6a}$, $R^{6b}$, $R^{11}$, $R^{12}$, $R^{13}$, $R^{14}$, $R^{21}$, $R^{22}$, $R^{23}$ and $R^{24}$ are each hydrogen.

8. The compound according to claim 1, which is selected from the group consisting of compounds of formulae (I-B) and (I-C)

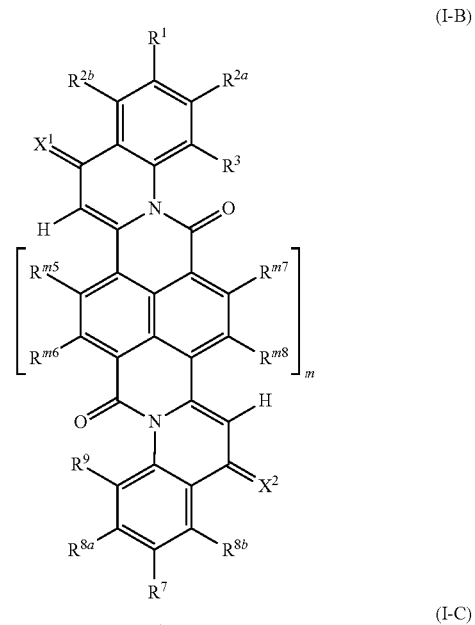

(I-B)

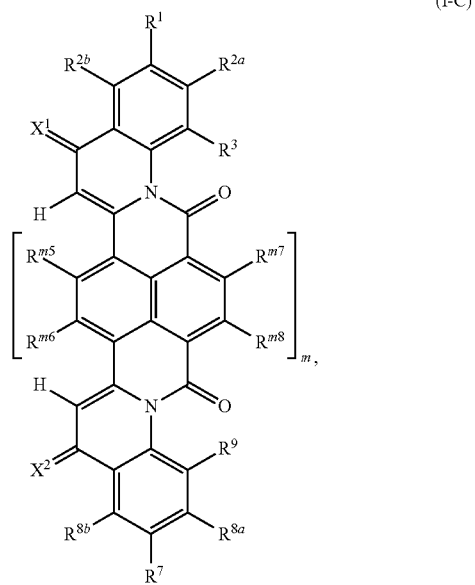

(I-C)

and mixtures thereof.

9. The compound according to claim 8, wherein $R^{m5}$, $R^{m6}$, $R^{m7}$ and $R^{m8}$ are, independently of one another, selected from the group consisting of hydrogen, $C_1$-$C_{30}$-alkoxy, $C_1$-$C_{30}$-alkylsulfanyl, aryloxy and arylthio where the two last mentioned radicals are unsubstituted or carry 1, 2 or 3 substituents selected from the group consisting of $SO_3H$, $C_1$-$C_{10}$-alkoxy and $C_1$-$C_{10}$-alkyl, which is unsubstituted or substituted by COOH.

10. The compound according to claim 8, wherein m is 1 or 2.

11. The compound according to claim 8, wherein m is 2, and 2 or 4 of the radicals $R^{15}$, $R^{16}$, $R^{17}$, $R^{18}$, $R^{25}$, $R^{26}$, $R^{27}$ and $R^{28}$ are selected from the group consisting of phenyloxy which is unsubstituted or substituted by 1, 2 or 3 substituents selected from the group consisting of $SO_3H$, $C_1$-$C_{10}$-alkoxy and $C_1$-$C_{10}$-alkyl which is unsubstituted or substituted by COOH and the remaining radicals $R^{15}$, $R^{16}$, $R^{17}$, $R^{18}$, $R^{25}$, $R^{26}$, $R^{27}$ and $R^{28}$ are each hydrogen.

12. The compound according to claim 8, wherein $R^{2a}$, $R^{2b}$, $R^3$, $R^{8a}$, $R^{8b}$ and $R^9$ are each hydrogen.

13. The compound according to claim 8, wherein $R^1$ and $R^7$ are, independently of one another, selected from the group consisting of hydrogen, chlorine, bromine, $C_1$-$C_{30}$-alkyl and $C_1$-$C_{30}$-haloalkyl.

14. A process for preparing a compound of the formula (I-A), or mixtures thereof:

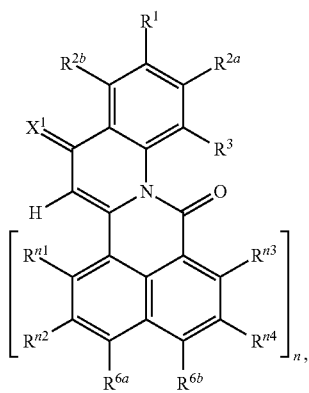
(I-A)

the process comprising:
(i) reacting a monoanhydride of the formula (II):

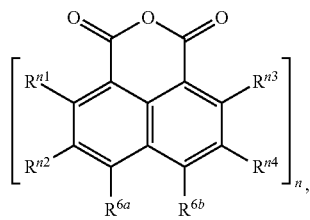
(II)

with a 2-acetyl aniline compound of the formula (III):

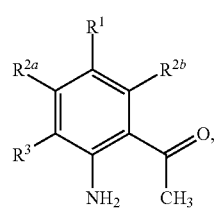
(III)

to obtain a compound of formula (I-Aa):

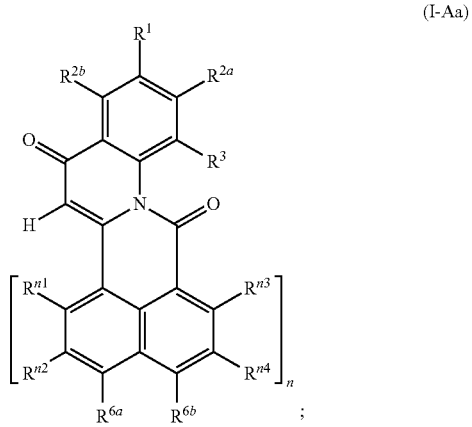
(I-Aa)

and
(ii) optionally reacting the compound of the formula (I-Aa) with malononitrile to obtain a compound of formula (I-Ab):

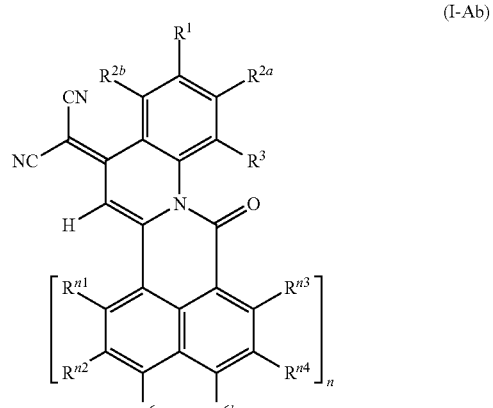
(I-Ab)

wherein:
$R^1$, $R^{2a}$ and $R^{2b}$ are independently of one another selected from the group consisting of hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino, $R^3$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$X^1$ is O or $C(CN)_2$;

n is 1, 2, 3 or 4; and $R^{n1}$, $R^{n2}$, $R^{n3}$, $R^{n4}$, are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$, in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino.

15. A process for preparing a compound of the formula (I-A), or mixtures thereof:

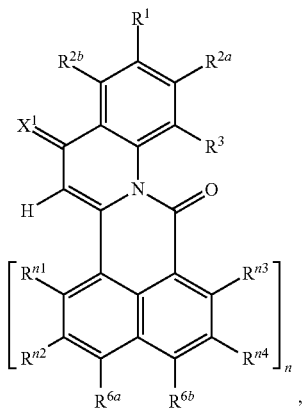

(I-A)

the process comprising:

(iii) reacting a monoanhydride of the formula (II):

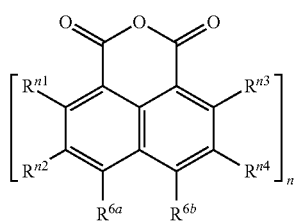

(II)

with a 2-bromoaniline of the formula (IV):

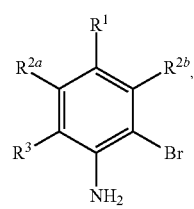

(IV)

to obtain a compound of formula (V):

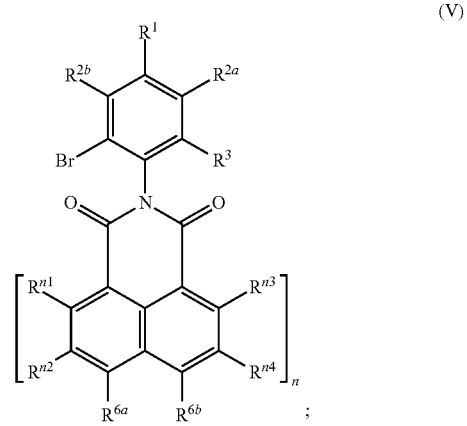

(V)

(iv) reacting the compound of formula (V) with tributyl (1-ethoxy-1-ethenyl)-stannane in the presence of a Pd catalyst to obtain a compound of formula (VI):

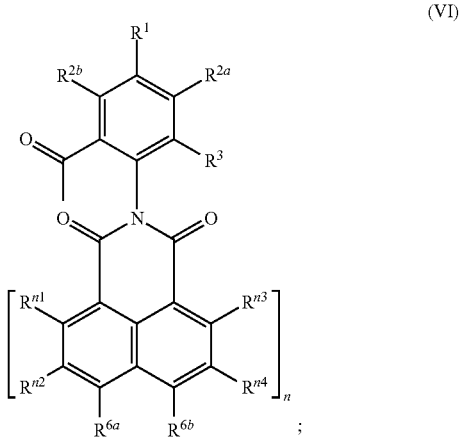

(VI)

(v) subjecting the compound of the formula (VI) to a condensation reaction to obtain a compound of the formula (I-Aa):

(I-Aa)

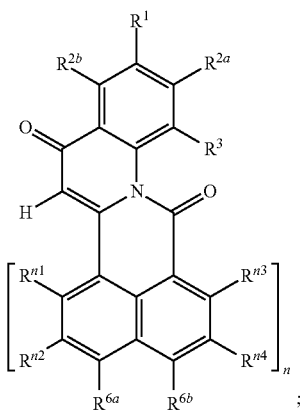

and
(vi) optionally, reacting the compound of the formula (I-Aa) with malononitrile to obtain a compound (I-Ab):

(I-Ab)

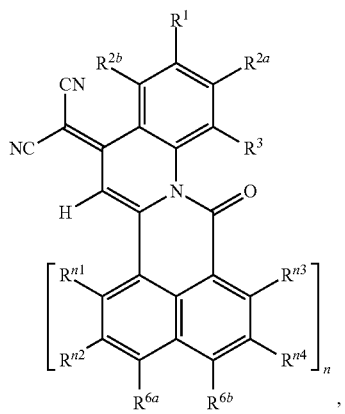

wherein:
$R^1$, $R^{2a}$ and $R^{2b}$ are independently of one another selected from the group consisting of hydrogen, F, Cl, Br, I, CN, hydroxy, mercapto, nitro, cyanato, thiocyanato, formyl, acyl, carboxy, carboxylate, alkylcarbonyloxy, carbamoyl, alkyl aminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, (monoaryl)amino, (diaryl)amino, hetaryl, hetaryloxy, hetarylthio, (monohetaryl)amino and (dihetaryl)amino;
$R^3$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;

$X^1$ is O or $C(CN)_2$;
n is 1, 2, 3 or 4; and
$R^{n1}$, $R^{n2}$, $R^{n3}$, $R^{n4}$, are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkyl aminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino.

16. A process for preparing compounds of the formulae (I-B) and (I-C):

(I-B)

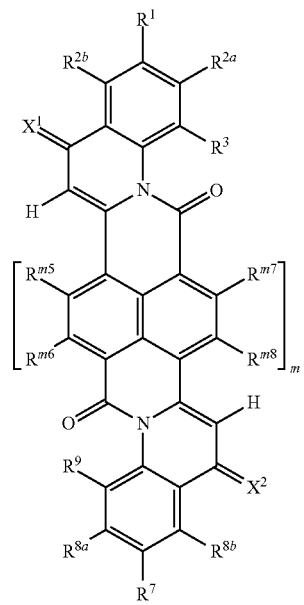

(I-C)

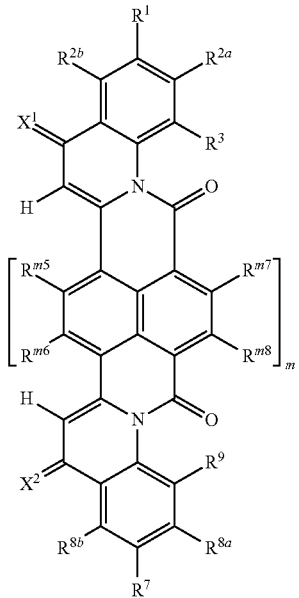

the process comprising:
(vii) reacting a dianhydride compound of the formula (VII):

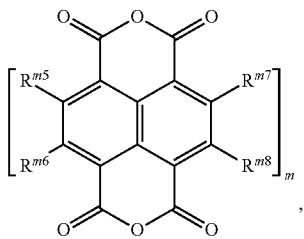
(VII)

with a 2-acetyl aniline compound of the formula (III) and optionally a different 2-acetyl aniline compound of the formula (IIIa):

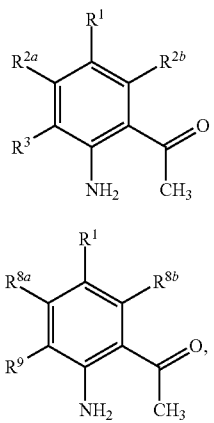
(III)

(IIIa)

to give a mixture of compounds of formulae (I-Ba) and (I-Ca):

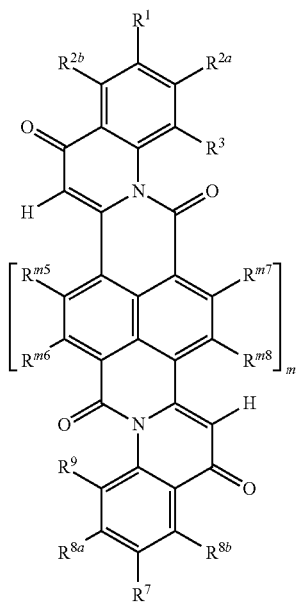
(I-Ba)

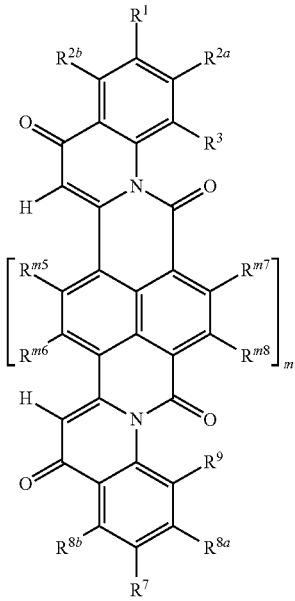
(I-Ca)

(viia) optionally separating the mixtures of compounds of formulae (I-Ba) and (I-Ca);

(viii) optionally reacting the compounds) obtained in step (vii) or (viia) with malononitrile to obtain the compound of formulae (I-Bb) or (I-Cb):

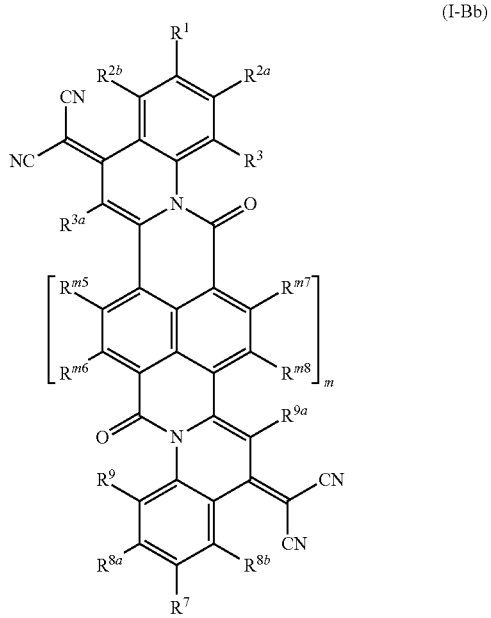
(I-Bb)

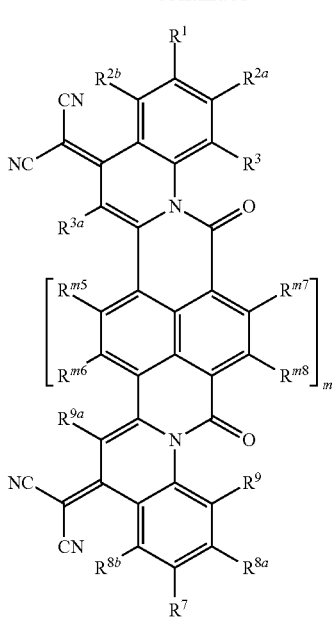

(I-Cb)

or mixtures thereof; and
(viiia) optionally separating the mixtures of compounds of formulae (I-Bb) and (I-Cb),
wherein:
$R^1$, $R^{2a}$ and $R^{2b}$ are independently of one another selected from the group consisting of hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, diaklaminocarbonyl, sulfo, sulfonate, sulfoamino, sulfamoyl, akisulfonyl, arylsulfonyl, amidino, $NE^1E^2$,
in each case unsubstituted or substituted alkyl, alkoxy, alkylthio, (monoalkyl)amino, dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;
$R^3$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;
$X^1$ is O or $C(CN)_2$;
m is 1, 2, 3 or 4;
$R^{m5}$, $R^{m6}$, $R^{m7}$ and $R^{m8}$ are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl, alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;
$R^7$, $R^{8a}$, $R^{8b}$ are independently of one another selected from hydrogen, F, Cl, Br, I, CN, hydroxy, mercapto, nitro, cyanato, thiocyanato, formyl, acyl, carboxy, carboxylate, alkylcarbonyloxy, carbamoyl, alkylaminocarbonyl, dialkylaminocarbonyl, sulfo, sulfonate, sulfoamino, sulfamoyl alkylsulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino;
$R^9$ is hydrogen, F, Cl, Br, I, CN, hydroxy, mercapto, nitro, cyanato, thiocyanato, carboxy, carboxylate, alkylcarbonyloxy, carbamoyl, alkylaminocarbonyl, dialkylaminocarbonyl, sulfo, sulfonate, sulfoamino, sulfamoyl, akisulfonyl, arylsulfonyl, amidino, $NE^1E^2$,
in each case unsubstituted or substituted alkyl, alkoxy, alkylthio, (monoalkyl)amino, (dialkyl)amino, cycloalkyl, cycloalkoxy, cycloalkylthio, (monocycloalkyl)amino, (dicycloalkyl)amino, heterocycloalkyl, heterocycloalkoxy, heterocycloalkylthio, (monoheterocycloalkyl)amino, (diheterocycloalkyl)amino, aryl, aryloxy, arylthio, (monoaryl)amino, (diaryl)amino, hetaryl, hetaryloxy, hetarylthio, (monohetaryl)amino and (dihetaryl)amino; and
$X^2$ is O or $C(CN)_2$.

17. A composition comprising the compound of claim 1, wherein the composition is adapted to function as a composition suitable for:
a fluorescent colorant:
data storage;
a UV absorber;
an optical label;
a fluorescent label for biomolecules;
laser welding of polymer materials;
an ink;
a surface coating; or
a coloring polymer composition.
18. A composition, comprising at least one compound of claim 1 and at least polymer.
19. The composition according to claim 18, wherein the thermoplastic polymer is selected from the group consisting of:
homo- and copolymers which comprise at least one copolymerized monomer selected from the group consisting of $C_2$-$C_{10}$-monoolefins, 1,3-butadiene, 2-chloro-1,3-butadiene, vinyl alcohol and its $C_2$-$C_{10}$-alkyl esters, vinyl chloride, vinylidene chloride, vinylidene fluoride, tetrafluoroethylene, glycidyl acrylate, glycidyl methacrylate, acrylates and methacrylates of $C_1$-$C_{10}$-alcohols, vinylaromatics, (meth)acrylonitrile, maleic anhydride, and α,β-ethylenically unsaturated mono- and dicarboxylic acids;
homo- and copolymers of vinyl acetals;
polyvinyl esters;
polycarbonates;
polyesters;
polyethers;
polyether ketones;
thermoplastic polyurethanes;
polysulfides;
polysulfones;
polyether sulfones;
cellulose alkyl esters;
and mixtures thereof.

20. An organic field-effect transistor, comprising a substrate having at least one gate structure, a source electrode and a drain electrode and at least one compound of claim 1 as a semiconductor material.

21. A substrate, comprising a plurality of organic field-effect transistors, at least some of the field-effect transistors comprising at least one compound of claim 1.

22. A semiconductor unit, comprising at least one substrate of claim 21.

23. An electroluminescent arrangement, comprising an upper electrode, a lower electrode, wherein at least one of said electrodes is transparent, an electroluminescent layer and optionally an auxiliary layer, wherein the electroluminescent arrangement comprises at least one compound of claim 1.

24. The electroluminescent arrangement of claim 23, comprising at least one compound of the formula (I) in a hole-injecting layer or as part of a transparent electrode.

25. The electroluminescent arrangement of claim 23 in form of an organic light-emitting diode (OLED).

26. An organic solar cell, comprising at least one compound of claim 1.

* * * * *

UNITED STATES PATENT AND TRADEMARK OFFICE
CERTIFICATE OF CORRECTION

PATENT NO. : 10,522,767 B2                             Page 1 of 1
APPLICATION NO. : 15/526866
DATED : December 31, 2019
INVENTOR(S) : Thomas Gessner et al.

It is certified that error appears in the above-identified patent and that said Letters Patent is hereby corrected as shown below:

In the Specification

In Column 24, Lines 2-18 delete " 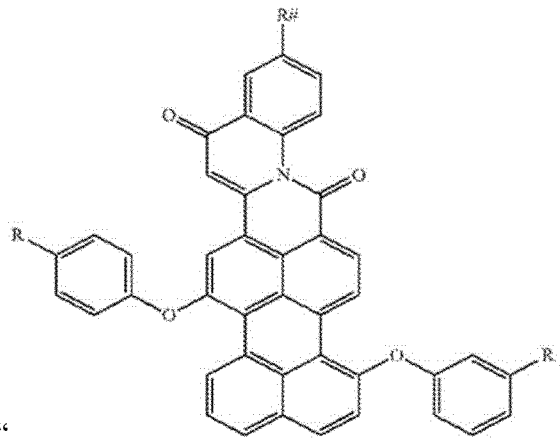 " and insert

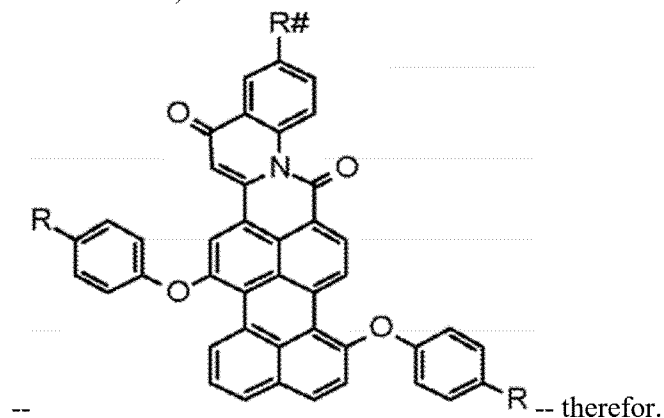 -- therefor.

Signed and Sealed this
Thirteenth Day of October, 2020

Andrei Iancu
*Director of the United States Patent and Trademark Office*